United States Patent
Zeitani

(10) Patent No.: US 10,583,008 B2
(45) Date of Patent: Mar. 10, 2020

(54) DEVICES AND IMPLANTATION METHODS FOR TREATING MITRAL VALVE CONDITIONS

(71) Applicant: Innercore Medical Ltd., Tel Aviv (IL)

(72) Inventor: Jacob Zeitani, Rome (IT)

(73) Assignee: Innercore Medical Ltd., Tel Aviv (IL)

( * ) Notice: Subject to any disclaimer, the term of this patent is extended or adjusted under 35 U.S.C. 154(b) by 0 days.

(21) Appl. No.: 16/143,512

(22) Filed: Sep. 27, 2018

(65) Prior Publication Data

US 2019/0029826 A1 Jan. 31, 2019

Related U.S. Application Data

(63) Continuation-in-part of application No. PCT/IL2017/051078, filed on Sep. 26, 2017, and a (Continued)

(30) Foreign Application Priority Data

Jan. 10, 2013 (IT) .............................. RM2013A0016

(51) Int. Cl.
*A61F 2/24* (2006.01)
*A61B 17/00* (2006.01)

(52) U.S. Cl.
CPC .......... *A61F 2/2445* (2013.01); *A61F 2/2409* (2013.01); *A61F 2/2442* (2013.01);
(Continued)

(58) Field of Classification Search
CPC .... A61F 2/2442; A61F 2/2445; A61F 2/2448; A61F 2/2454; A61F 2/2457
See application file for complete search history.

(56) References Cited

U.S. PATENT DOCUMENTS

| 2003/0083742 A1 | 5/2003 | Spence et al. |
| 2003/0199975 A1 | 10/2003 | Gabbay |

(Continued)

FOREIGN PATENT DOCUMENTS

WO  WO 2012/094406  7/2012

OTHER PUBLICATIONS

U.S. Final Office Action for U.S. Appl. No. 14/759,349, dated Mar. 30, 2017.

(Continued)

*Primary Examiner* — Leslie Lopez
(74) *Attorney, Agent, or Firm* — Pearl Cohen Zedek Latzer Baratz LLP

(57) ABSTRACT

Mitral valve implants and devices, kits and methods are provided for mitral valve repair. Devices comprise a body attachable onto the mitral valve annulus and a bridge connected to the body by two legs which are configured to support and position the bridge within a left ventricle (LV) of the patient when the device body is implanted, so that the legs and the bridge avoid contact with the LV walls, papillary muscles and chordae during operation of the heart. The bridge may be used to anchor valve leaflet tissue, provide support for leaflet re-modelling, possibly using external tissue, and/or anchor artificial chords used to modify and repair the operation of the mitral valve. Related medical procedures as well as kits and related utensils are also provided.

27 Claims, 34 Drawing Sheets

Related U.S. Application Data continuation-in-part of application No. 14/759,349, filed as application No. PCT/IB2014/058175 on Jan. 10, 2014, now abandoned.

(60) Provisional application No. 62/399,523, filed on Sep. 26, 2016.

(52) U.S. Cl.
CPC ... *A61B 2017/00243* (2013.01); *A61F 2/2454* (2013.01); *A61F 2/2457* (2013.01); *A61F 2/2466* (2013.01); *A61F 2210/0014* (2013.01); *A61F 2220/0008* (2013.01); *A61F 2250/006* (2013.01)

(56) References Cited

U.S. PATENT DOCUMENTS

| | | |
|---|---|---|
| 2004/0127982 A1 | 7/2004 | Machold et al. |
| 2005/0038509 A1 | 2/2005 | Ashe |
| 2006/0259135 A1 | 11/2006 | Navia et al. |
| 2007/0050020 A1 | 3/2007 | Spence |
| 2009/0306622 A1 | 12/2009 | Machold et al. |
| 2010/0262233 A1* | 10/2010 | He ................ A61F 2/2445 623/2.36 |
| 2010/0280606 A1* | 11/2010 | Naor ............... A61F 2/2418 623/2.18 |
| 2012/0179247 A1 | 7/2012 | Navia |
| 2015/0094803 A1* | 4/2015 | Navia .............. A61F 2/2445 623/2.36 |
| 2015/0335427 A1 | 11/2015 | Zeitani |

OTHER PUBLICATIONS

Siew Yen Ho; Anatomy of the mitral valve; Heart 2002;88(Suppl IV):iv5-iv10.
Alexandra A. Degandt et al; Mitral Valve Basal Chordae: Comparative Anatomy and Terminology; 2007 by The Society of Thoracic Surgeons; Published by Elsevier Inc.
International Preliminary Report on Patentability for Application No. PCT/IB2014/058175 dated Jul. 14, 2015.
Search Report for Italian Application No. RM2013A000016, dated Oct. 21, 2013.
International Search Report for Application No. PCT/IB2014/058175 dated Apr. 1, 2014.
U.S. Office Action for U.S. Appl. No. 14/759,349, dated Sep. 30, 2016.
U.S. Office Action for U.S. Appl. No. 14/759,349, dated Mar. 30, 2017.
U.S. Office Action for U.S. Appl. No. 14/759,349, dated Sep. 8, 2017.
U.S. Final Office Action for U.S. Appl. No. 14/759,349, dated Mar. 28, 2018.
International Search Report for Application No. PCT/IL2017/051078 dated Dec. 24, 2017.
Search Report dated Dec. 30, 2019 for PCT Application No. PCT/IL2019/051046.

* cited by examiner

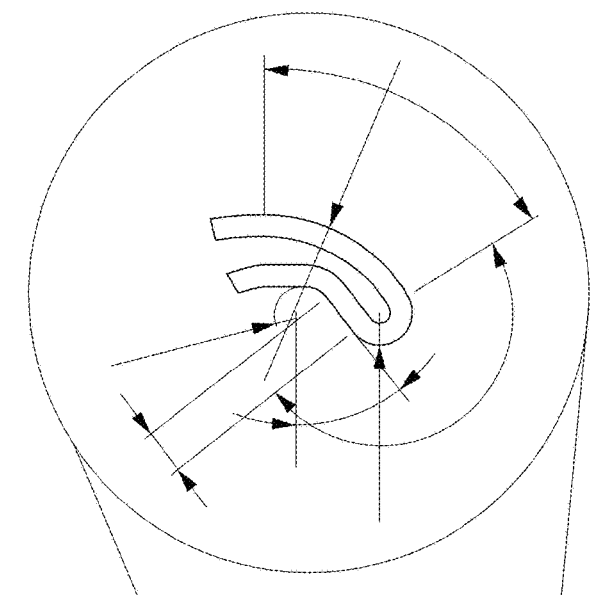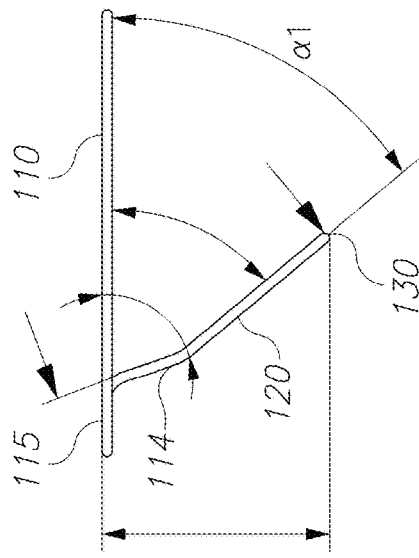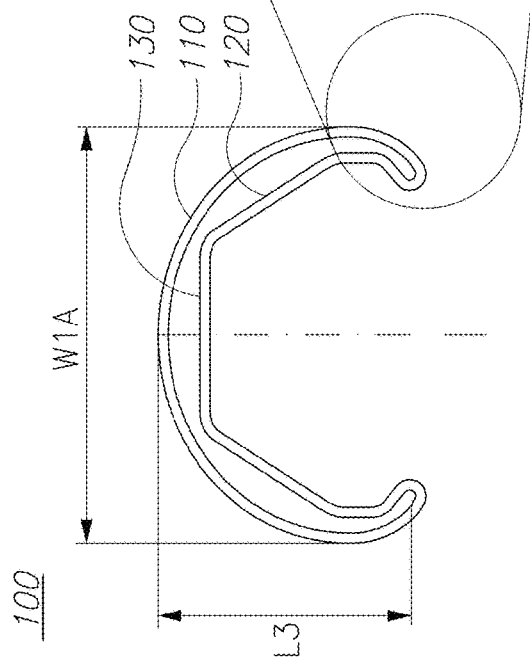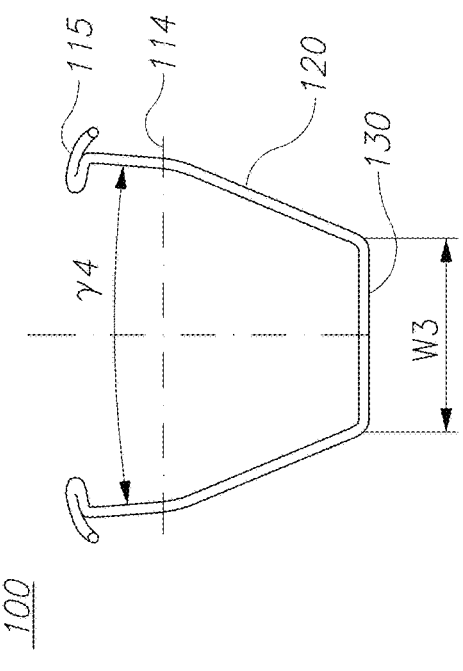
Figure 3A
Figure 3C
Figure 3B

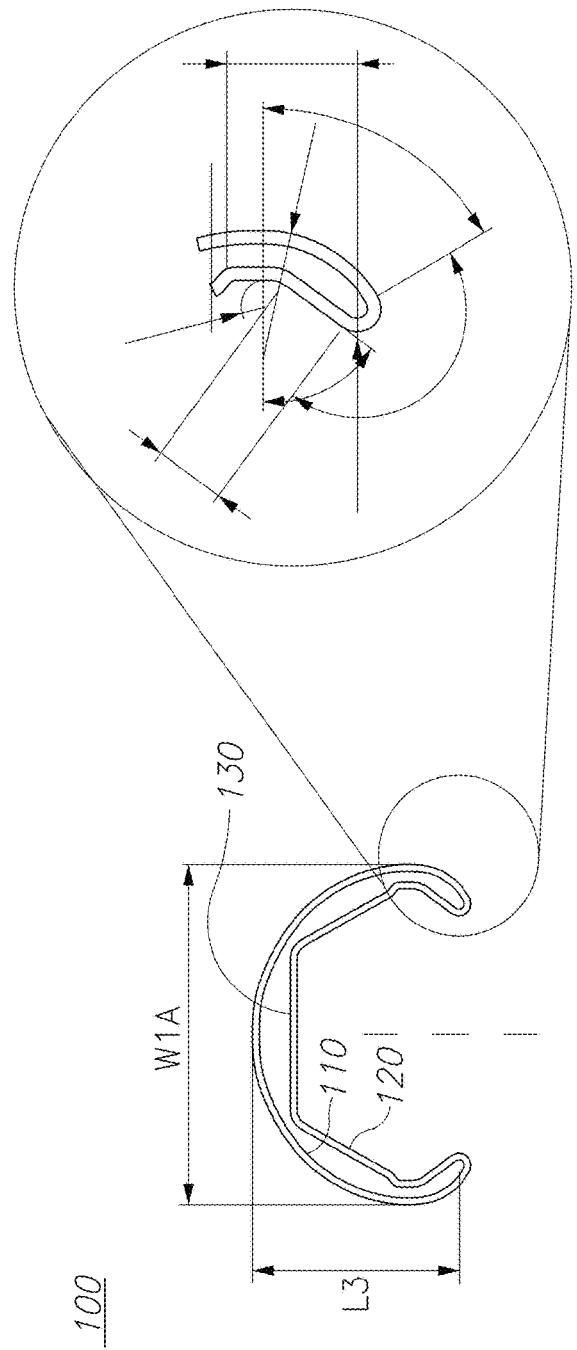
Figure 3D
Figure 3E
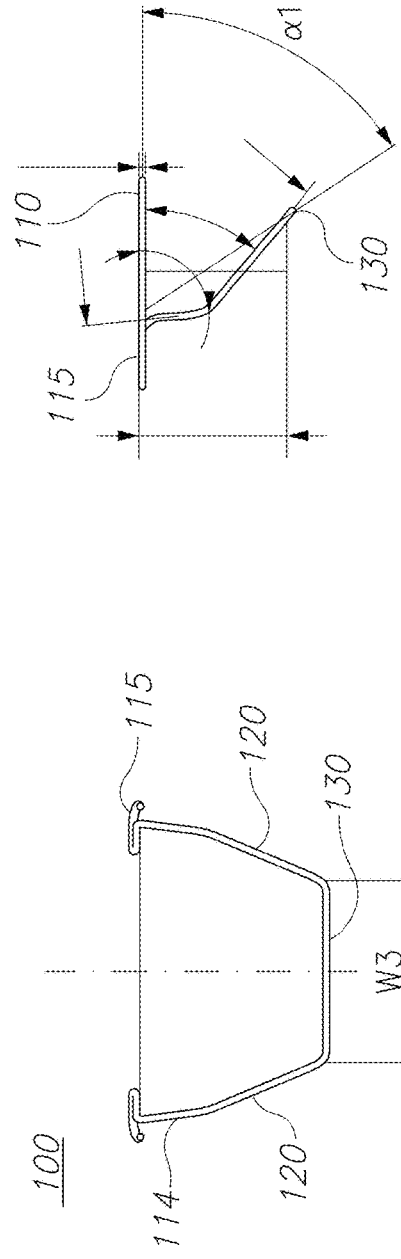
Figure 3F

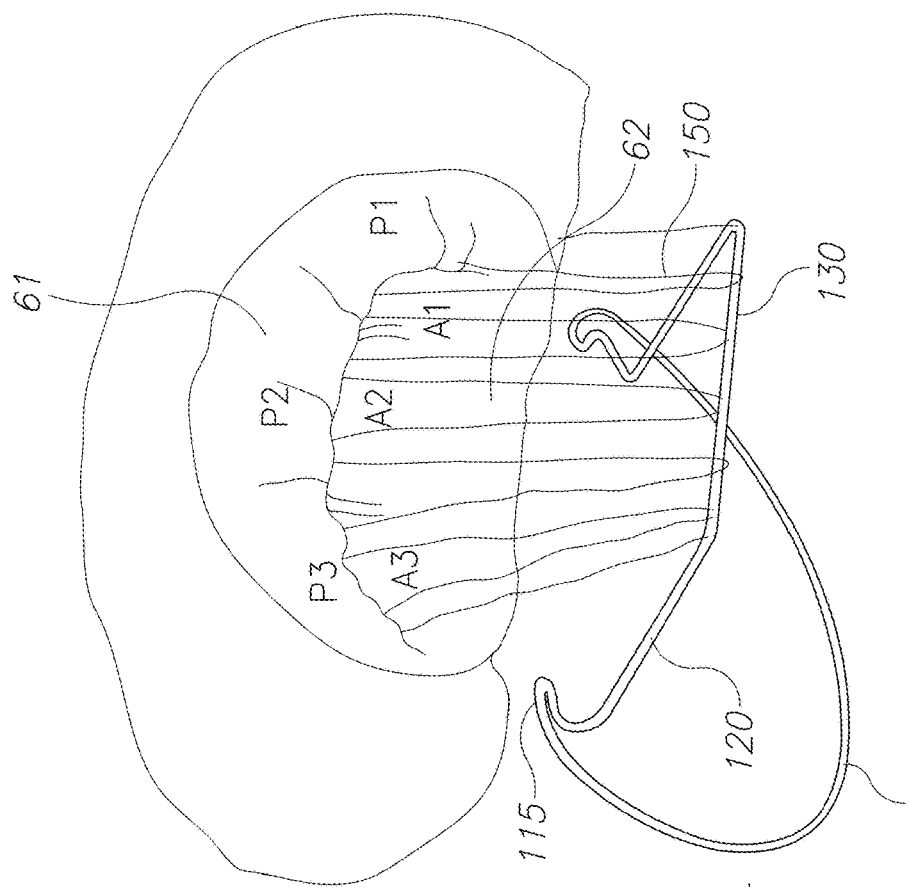
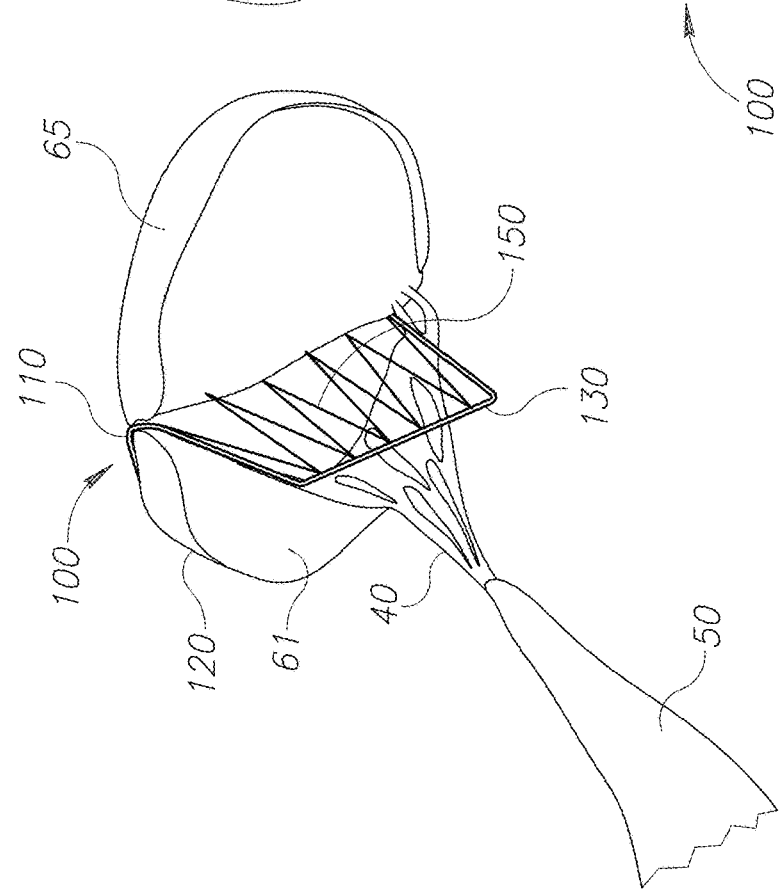
Figure 6C
Figure 6D

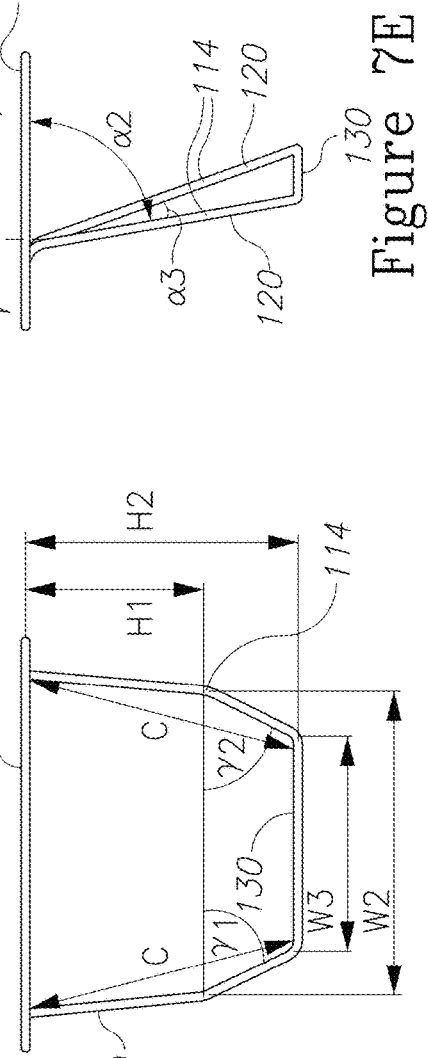
Figure 7C
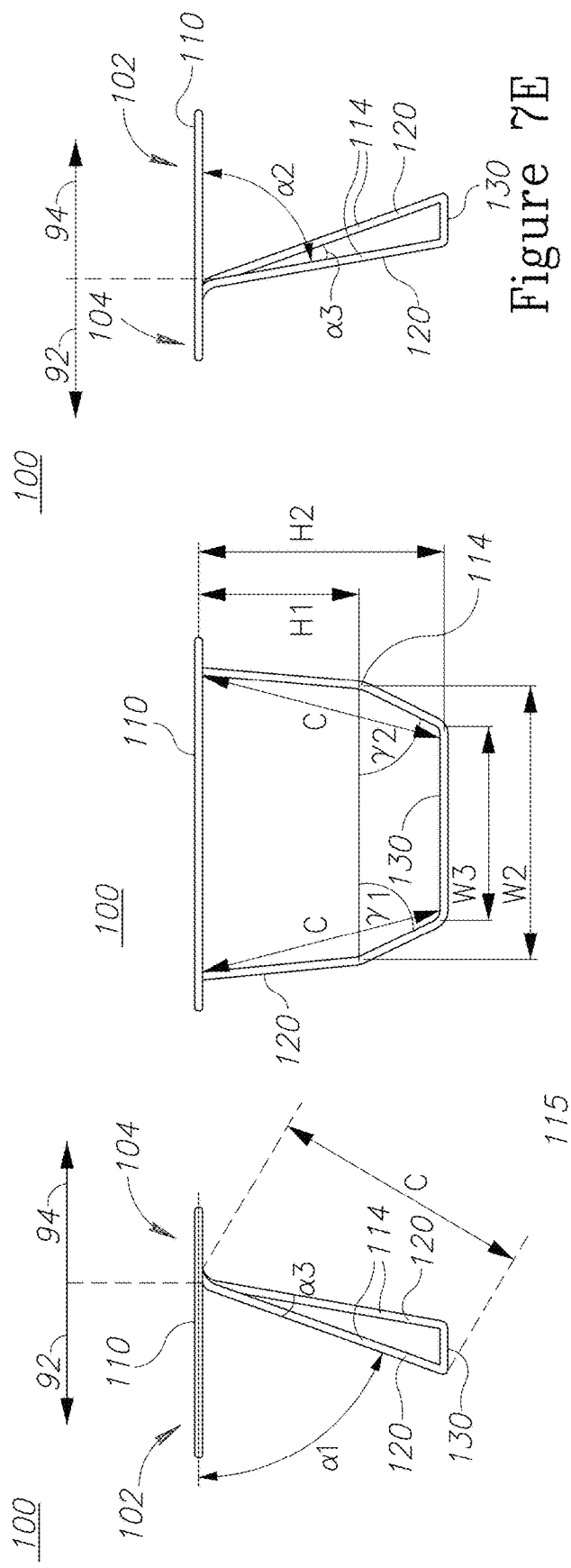
Figure 7D
Figure 7E
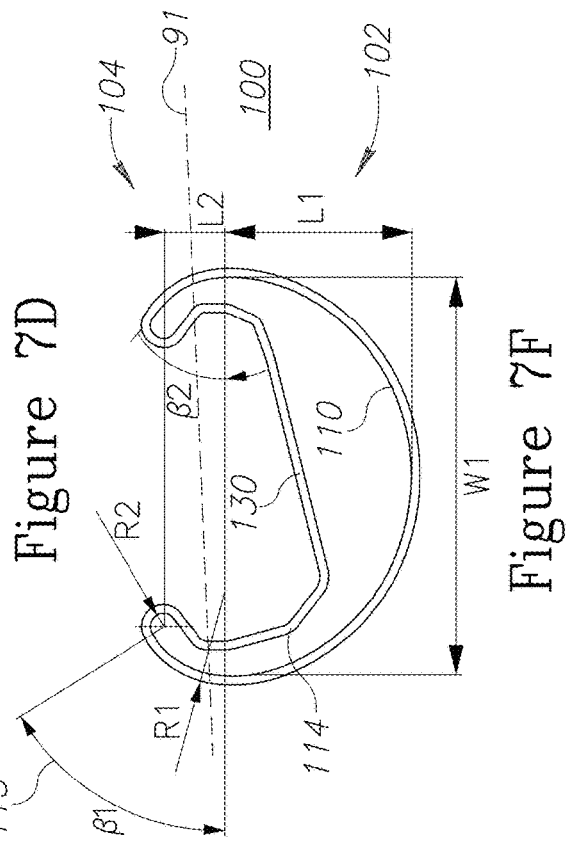
Figure 7F

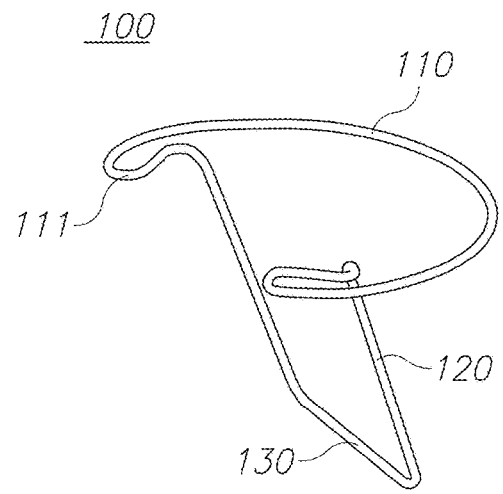
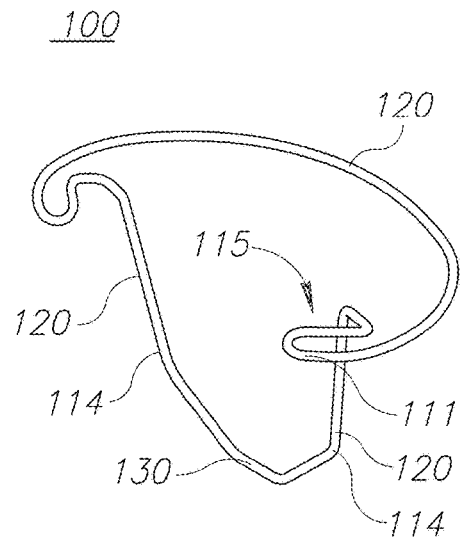
Figure 7G    Figure 7H
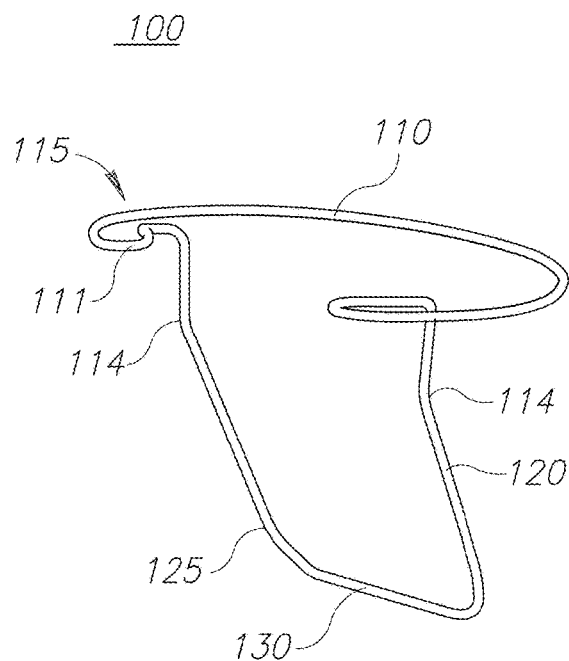
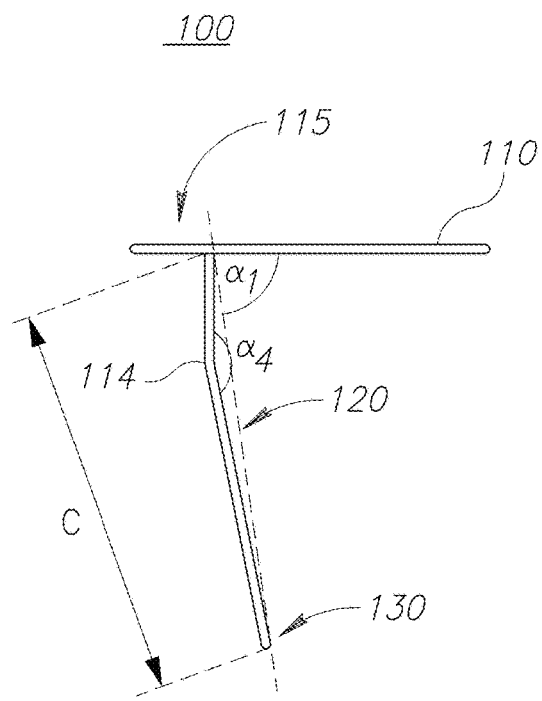
Figure 7I    Figure 7J

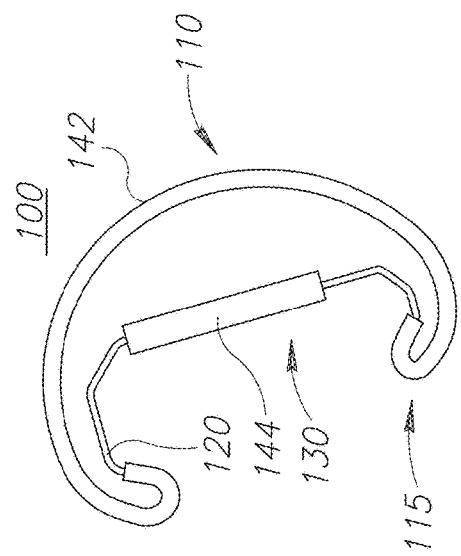
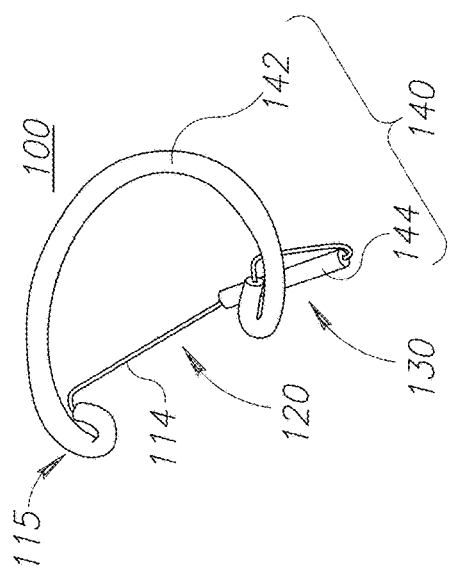
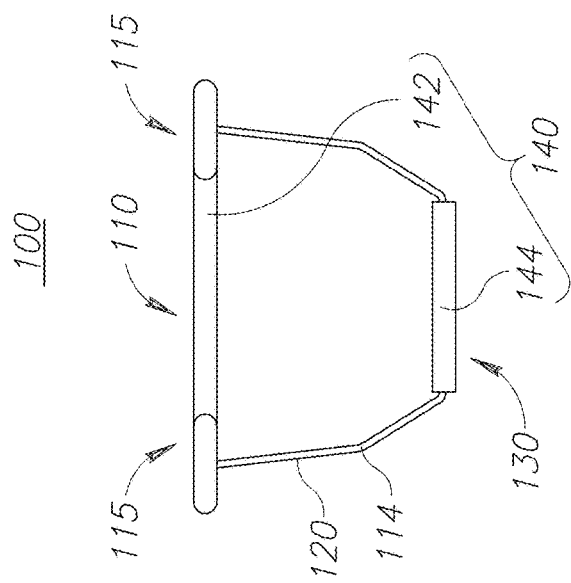

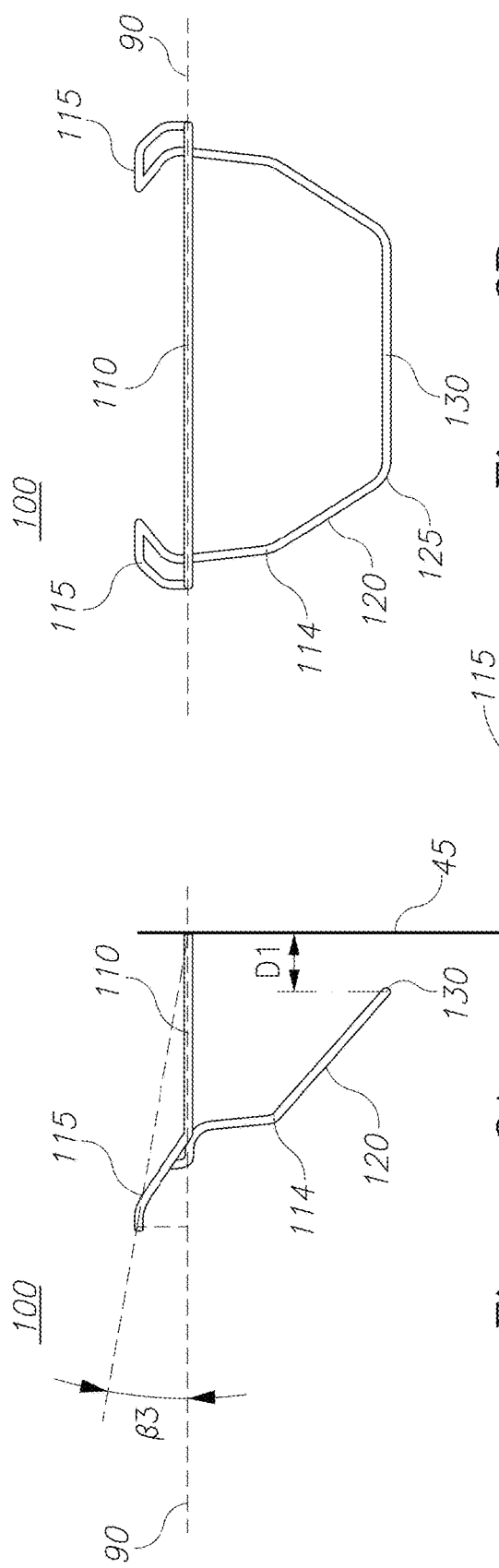
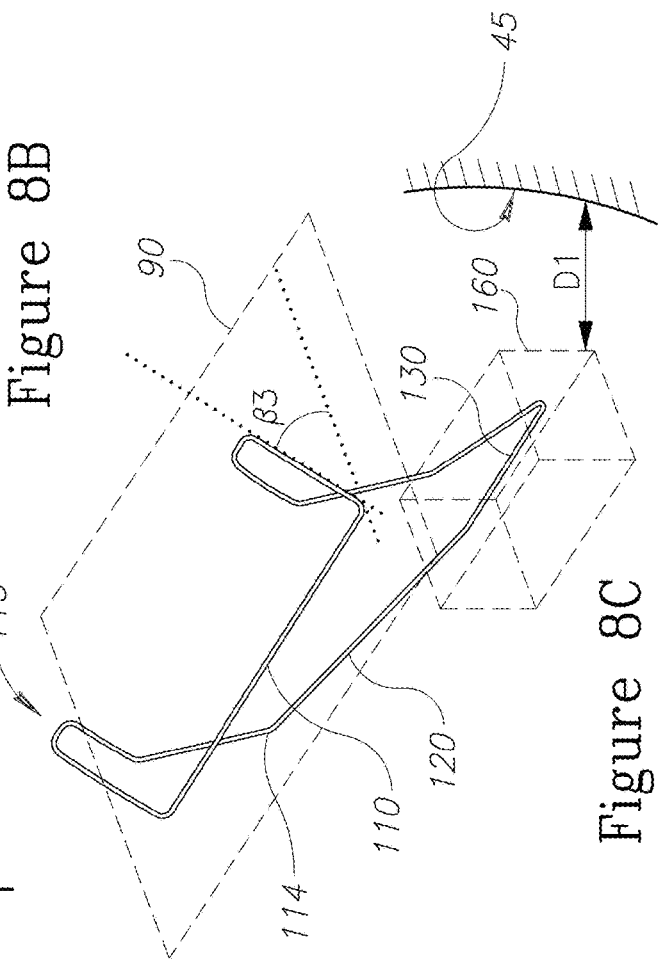
Figure 8A
Figure 8B
Figure 8C

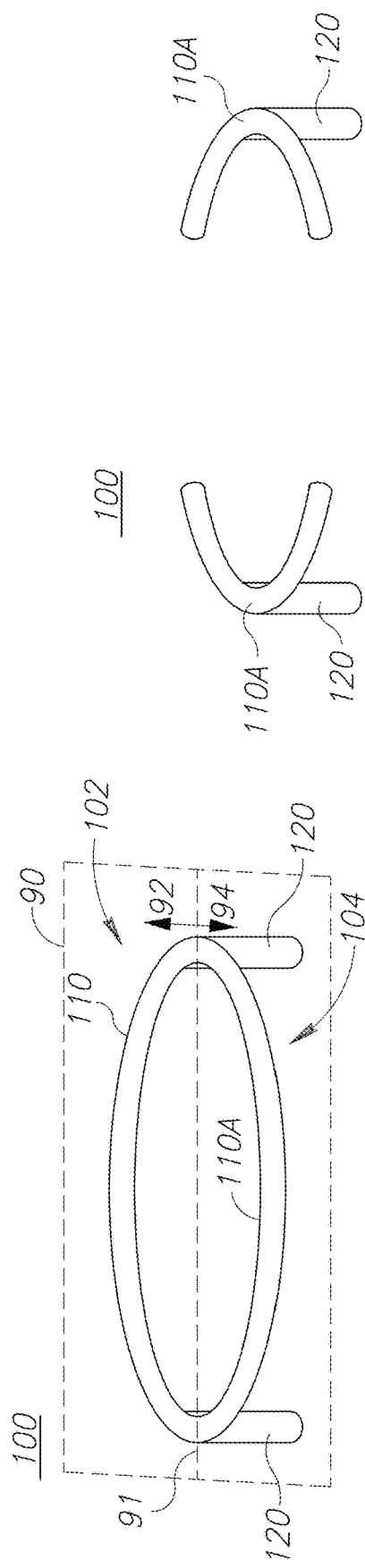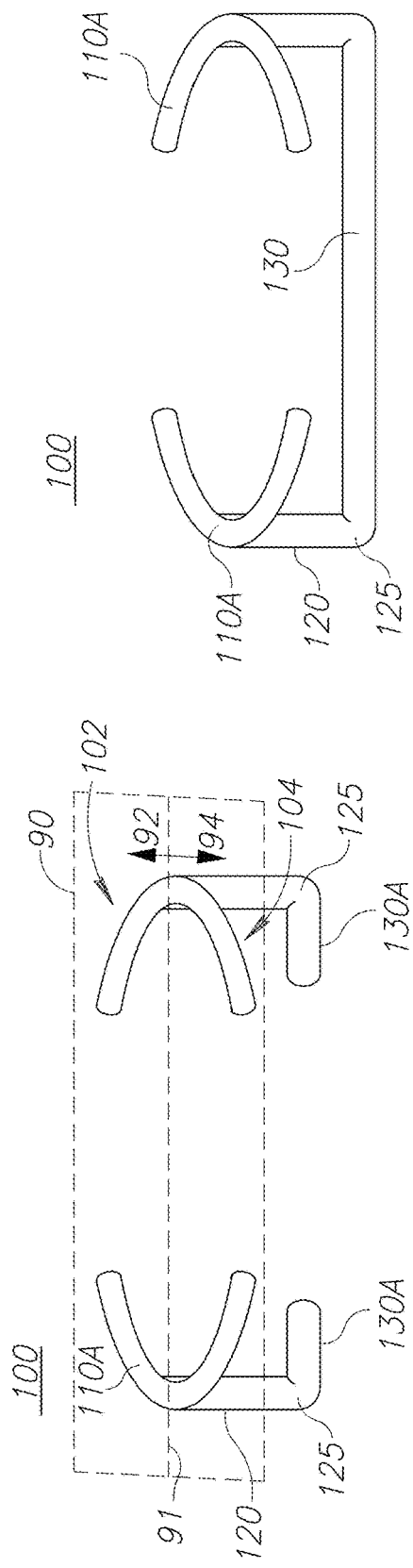

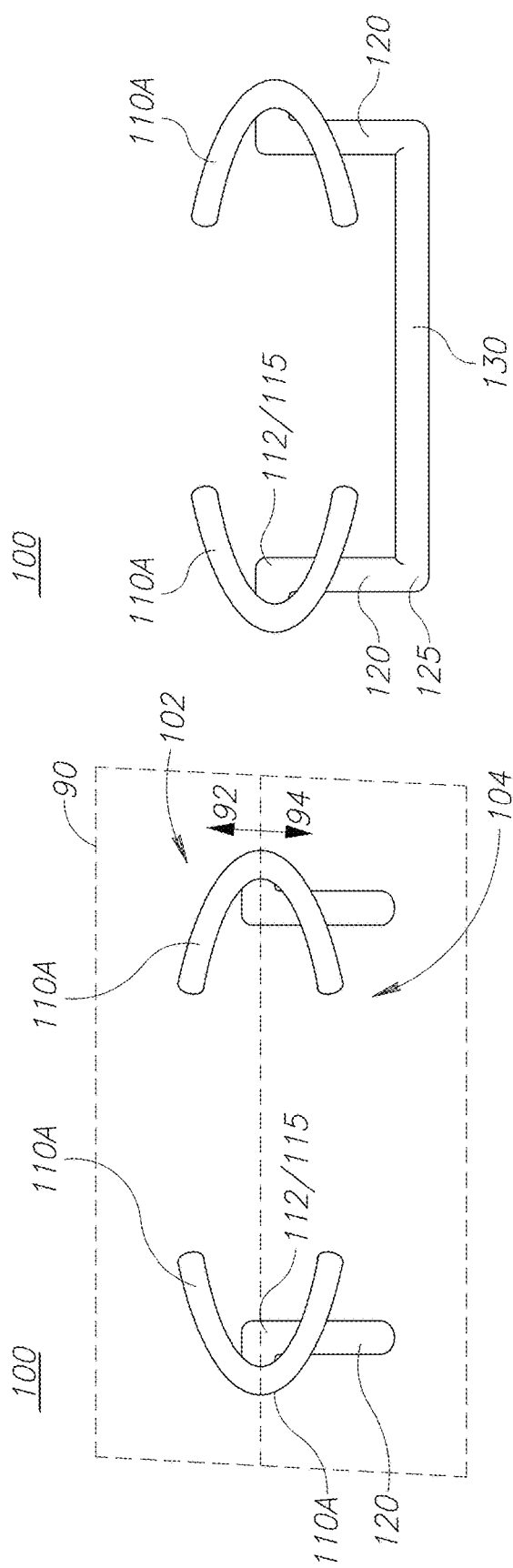
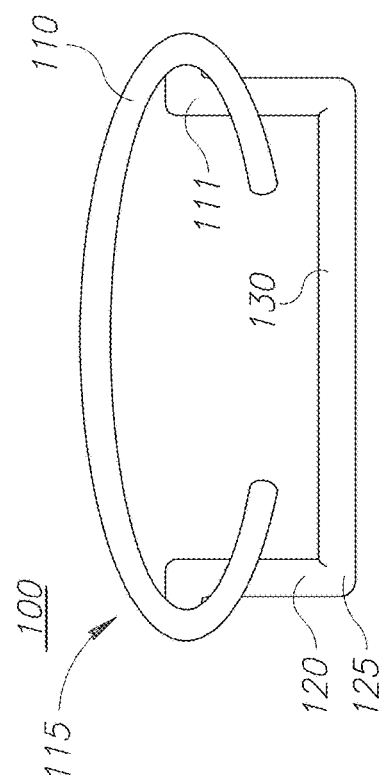
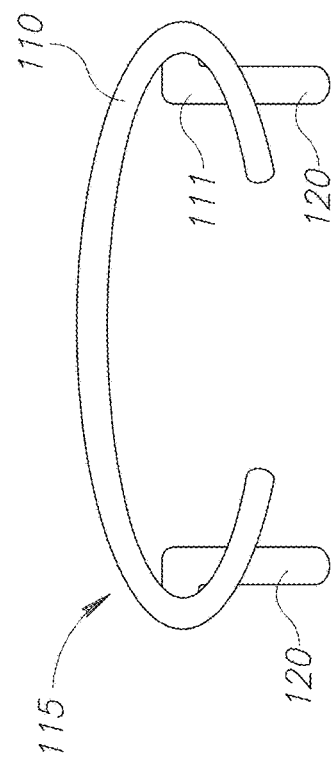
Figure 9E
Figure 9F
Figure 9G
Figure 9H

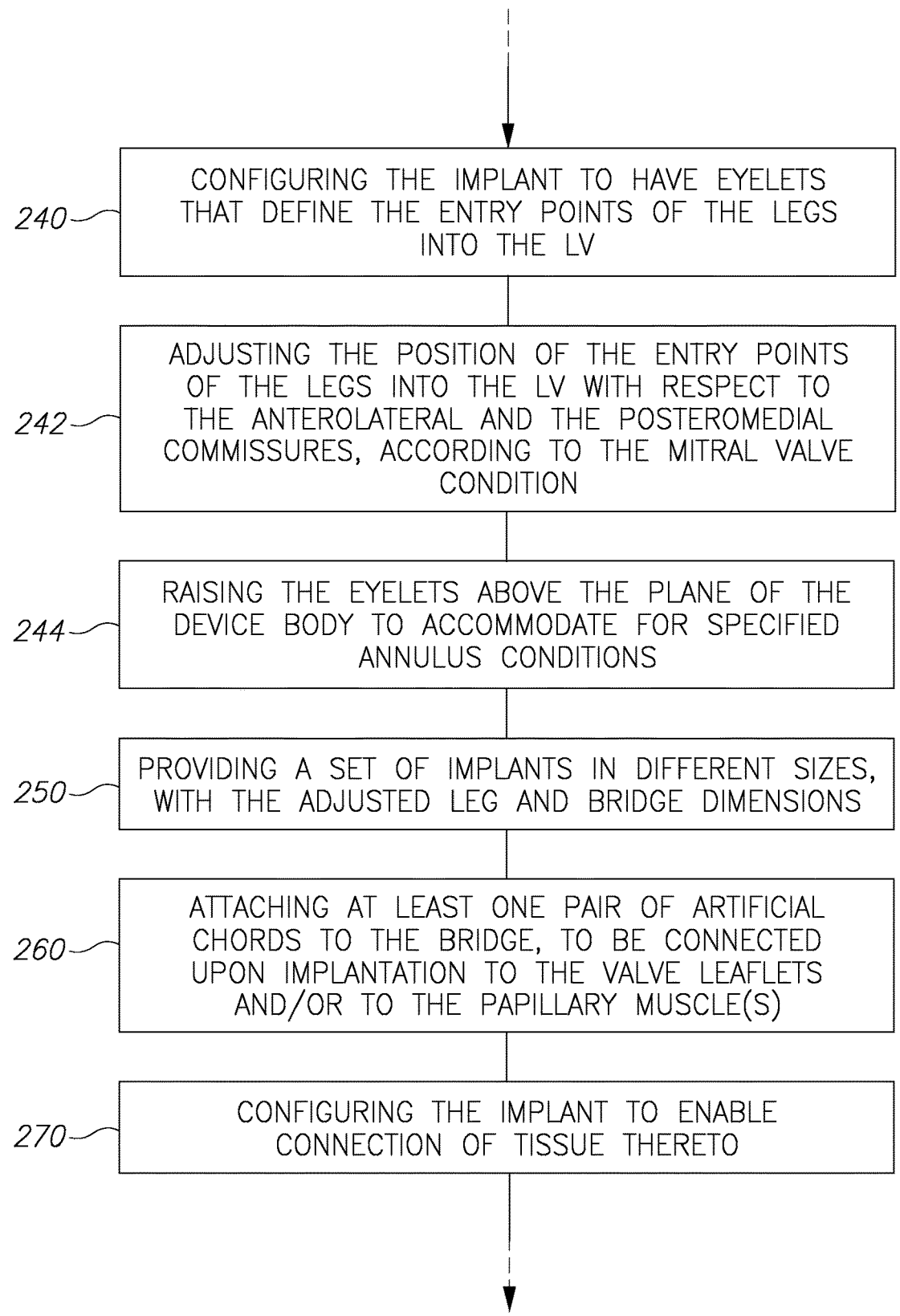
Figure 12 (cont. 1)

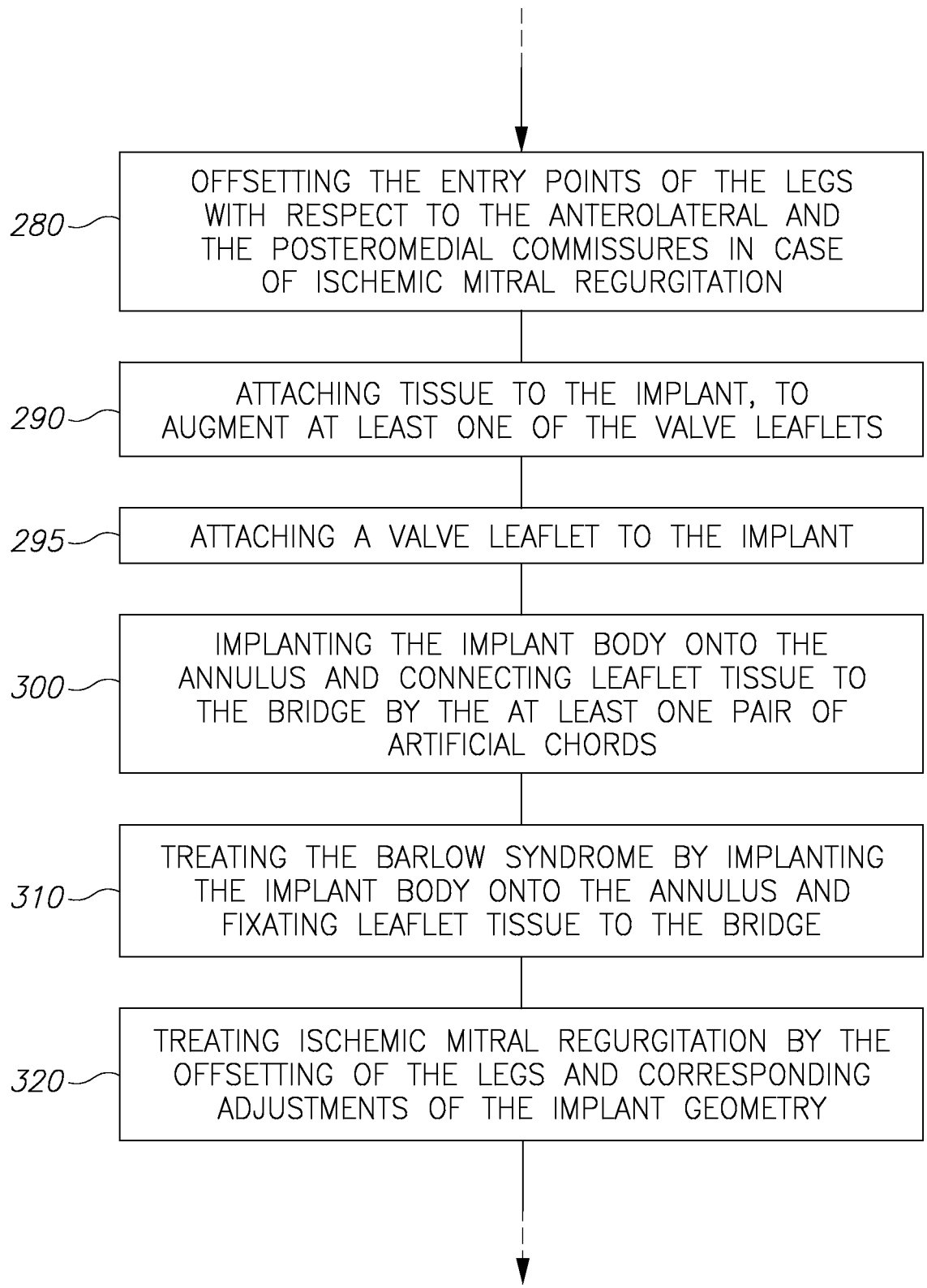
Figure 12 (cont. 2)

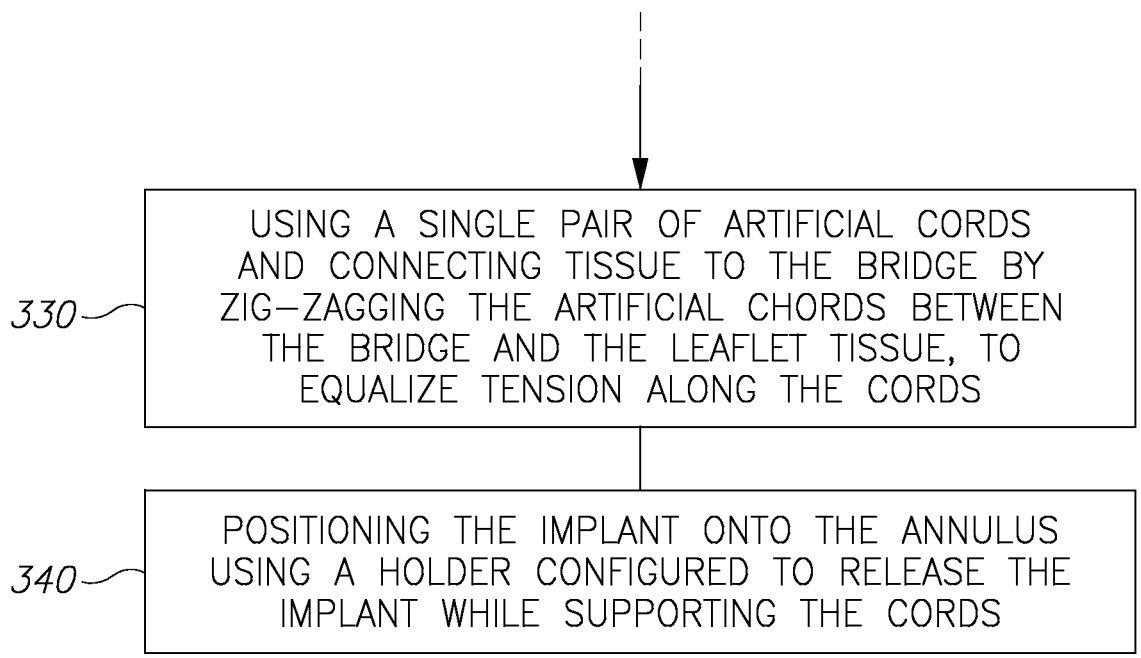
Figure 12 (cont. 3)

DEVICES AND IMPLANTATION METHODS FOR TREATING MITRAL VALVE CONDITIONS

CROSS REFERENCE TO RELATED APPLICATIONS

This application is a continuation in part of U.S. patent application Ser. No. 14/759,349 filed on Jul. 6, 2015, which is a national phase of PCT Application No. PCT/IB2014/058175 field on Jan. 10, 2014, published on Jul. 17, 2014, under publication No. WO 2014/108859, which claims priority of Italian Patent Application No. RM2013A000016 filed on Jan. 10, 2013; this application is also a continuation in part of PCT Application No. PCT/IL2017/051078, filed Sep. 26, 2017, published on Mar. 29, 2018, under publication WO 2018/055629, which claims the benefit of U.S. Provisional Patent Application No. 62/399,523 filed on Sep. 26, 2016; all of which are incorporated herein by reference in their entirety.

BACKGROUND OF THE INVENTION

1. Technical Field

The present invention relates to the field of mitral valve treatment, and more particularly, to devices and methods for treating mitral valve conditions

2. Discussion of Related Art

The substitution of the mitral valve and the mitral repair are "open heart" operations executed by heart surgeons in order to treat a stenosis (narrowing) or an insufficiency (loss) of the mitral valve. This is the inlet valve for the left part of the human heart which, as is known, is substantially composed of four chambers: two pumping chambers, i.e. the ventricles, and two filling chambers, i.e. the atria. From the right ventricle, blood is thrust into the pulmonary circulation, from which it exits enriched with oxygen, while the left ventricle pumps blood into the systemic circulation, up to the periphery. The blood is correctly driven, from the ventricles to the circulation and from the atria to the ventricles, by means of systems that prevent the existence of flows in retrograde direction. These systems, known as heart valves, are the structures that regulate the flow of blood inside the heart. These are appendages of essentially fibrous tissue, covered with endocardium, which control the passage of blood through the orifices that connect atria with ventricles and the ventricles with aorta or pulmonary artery. The opening and closing of the valves is entirely tied with the intracardiac pressure variations. Indeed, there are no nerve controls of the activity of the valves, which are thus simply thrust by the blood flow itself. The main task of the heart valves is that of preventing, ensuring an effective and passive resistance, the reflux of blood towards the atria during the ventricular contraction or towards the ventricles during the diastolic phase. There are four cardiac valves, in particular: the tricuspid valve, the bicuspid or mitral valve, the aortic valve with three semi-lunar cusps and the pulmonary valve with three semi-lunar cusps. Of particular interest for the present invention is the mitral valve. The valve has a diameter of over 30 mm, it regulates the blood flow between the left atrium and the left ventricle, has an orifice of 4-6 cm and has a slightly oval form, analogous to the tricuspid valve, it too of nearly oval form.

Unlike the latter, the mitral valve has two cusps or flaps. A larger one is arranged forward and medially, which corresponds to the front and left wall of the septum, which guards the aortic orifice and is termed front aortic cusp. The other, smaller cusp is placed in the back and laterally, corresponds with the rear wall of the left ventricle and is called rear cusp.

In general, the incorrect functioning of the heart valves, which is defined valvular heart disease, is substantially manifested in two forms. One form, stenosis, is represented by an incomplete opening of the valve, involving the passage of blood into a smaller-than-normal orifice; another form, insufficiency, is represented by an incomplete closure, involving the reflux of blood through the valve, which must instead be closed. Very often, stenosis and insufficiency coexist, to a different extent in the same valve, achieving the so-called steno-insufficiency. It is further observed that valvular heart diseases can be congenital or acquired. The latter can be of degenerative, infective, ischemic, traumatic or secondary origin, with conspicuous dilation of the ventricle. The course of valvular heart diseases is in most cases slowly evolutional, with a very long phase (years) completely without symptoms.

The diseases of the valves of the right part of the heart, i.e. of the tricuspid and pulmonary valves where a lower pressure operating condition is in force, are rare and generally due to congenital problems.

The diseases involving the mitral valve and aorta are instead much more frequent. Of course, the consequences of valve disease depend on the type of irregularity and the severity thereof. In any case, the most extreme consequence of each valvular heart disease is cardiac decompensation.

Even if difficult to generalize, it can be stated that each valvular heart disease passes through two phases: a first compensation phase, during which the heart implements a series of mechanisms in order to confront the problem, and a second which evolves towards cardiac insufficiency, when the adaptation mechanisms are no longer sufficient to maintain a suitable heart rate.

The resolutive treatment of valvular heart diseases is usually of surgical type: medical treatment has the objective of slowing the progression and/or controlling the symptoms in congenital and acquired valvular heart diseases, e.g. acquired following the prolonged assumption of diuretics and vasodilators, or of contributing to the clinical stabilization of acute valvular heart diseases. In most cases, the dysfunctions of the mitral valve are associated with degenerations due to an excessive weakness of the structure of the leaflets or of the tendinous cords, which can cause the elongation of the latter and in some cases also the breakage.

For example, a common pathological form of the mitral valve, which is encountered in many patients, is represented by the dilation of the left ventricle, generally involving an increase of the distance between the papillary muscles and the mitral annulus. This pathology consequently causes an increase of the tension of the tendinous cords and a lowering of the circular crown, of the valve, below the plane where the crown would lie in normal conditions. Conventionally and for the purpose of facilitating the comprehension of the invention described hereinbelow, this plane is arranged perpendicular to the direction of the blood flow. The lowering of the circular crown below the plane perpendicular to the direction of the blood flow, and the tension of the tendinous cords, cause the lacking or correct superimposition of the leaflets, i.e. of the mitral cusps, during the systolic phase.

FIGS. 1D and 1E respectively show left ventricle (LV) 75 of a human heart 70 in which the mitral valve 60 functions correctly, and left ventricle 75 of human heart 70 in which mitral valve 60 functions incorrectly caused by an insufficiency due to the excessive dilation of LV 75 in question. FIGS. 1D and 1E further illustrate the presence of the papillary muscles 50A and 50B, of the tendinous cords 40, of the mitral cusps 61, 62 as well as of a hypothetical plane 90 coplanar with native mitral annulus 65, wherein mitral annulus 65 does not have damages. Also indicated is the direction 71 of the blood flow, perpendicular (or substantially perpendicular) to plane 90.

The various pathologies verifiable in subjects affected by valvular heart diseases almost always require that the operation pertaining to the valve repair or substitution is accompanied by an operation to be executed on the tendinous cords, with the intention of restoring a more physiological tension of the cords themselves. More in detail, the degenerative valve disease can be caused by a lengthening or by a breakage of the tendinous cords, i.e. of the support apparatus of the "normal" valve, or by a more general weakening of the valve itself (myxomatous degeneration), in which all the components of the valve are enlarged or elongated. The type of repair depends on the specific problem and can consist of the removal of broken valve segments, in shortening elongated cords, in implanting synthetic cords in place of those broken or elongated and still other actions. Almost always, a "ring" is implanted, of circa 3 cm size, which surrounds the annulus of the valve in order to consolidate the repair. When the mitral valve is overly damaged, to the point where repair cannot take place, it is substituted with an artificial valve such as a mechanical or biological valve known in the literature.

Currently, the state of the art attests that various devices have been achieved and developed for modifying the size of the mitral orifice, restoring a more physiological valvular activity. In any case, it is deemed that the devices currently in use and the operation methods associated therewith can be considerably improved, e.g. for the purpose of reducing the stresses associated with the implant of conventional rings, and in order to be able to induce a repair even in cases where the implant of conventional rings has been made impossible, for example due to partial or total calcifications of the mitral annulus, which make it difficult to implant the annular device, by means of suture, on the damaged mitral apparatus.

Mitral regurgitation (MR)—also referred to as mitral insufficiency or mitral incompetence—is a common disorder caused by insufficient closure (coaptation) of the mitral valve leaflets when the left ventricle contracts. This leads to abnormal leaking of blood backwards from the left ventricle, through the mitral valve and into the left atrium.

In the western world, MR is most commonly due to degenerative disease caused by morphological or functional changes to the leaflets, the valve annulus (which forms a ring around the valve leaflets), the papillary muscles and/or the chordae tendineae (which connect the valve leaflets to the papillary muscles). Morphological changes are classified under Degenerative Mitral Regurgitation (DMR) while functional changes are classified under functional mitral regurgitation (FMR).

Treatment of mitral valve regurgitation includes medication such as diuretics beta blockers, heart rhythm regulators and/or surgery for augmenting or replacing mitral valve function.

Mitral valve augmentation is typically effected via implantation of a ring-like device at the valve annulus. The procedure, termed annuloplasty, reshapes the mitral valve annulus to reestablish the physiological configuration and improve leaflet coaptation.

Mitral valve repair can be achieved by ring implantation alone, however, cases involving leaflets with sever anomalies and/or chordate elongation or damage to papillary muscles oftentimes require additional repair procedures.

One such procedure utilizes artificial chords which are sutured between the papillary muscles in the left ventricle (LV) and the free margin of the valve leaflet in order to recover the coaptation line. However, left ventricle remodeling in the postoperative period might negatively affect early results and lead to recurrence of mitral regurgitation. In addition to LV remodeling, suturing of artificial chord to the papillary muscle can be difficult to perform since the surgeon has limited access through the valve, making surgery more complex and time consuming and since it is oftentimes difficult to determine the correct length of artificial chords needed. In addition, the papillary muscle might be damaged by the procedure risking rupture of suturing site.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides a device comprising a body configured to be attached and implanted onto an annulus of a patient's mitral valve, and a bridge connected to the body by two legs which are configured to support and position the bridge within a left ventricle (LV) of the patient when the device body is implanted, wherein the legs are configured to position the bridge within a specified space in the LV which is free of chordae and papillae during heart functioning, the specified space defined by a depth between 10 mm and 30 mm below the device body, a width W between 15 mm and 30 mm with respect to a median plane of the device, and a length L between −5 mm and +15 mm with respect to a posterior edge of the device body.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 3A-3M are schematic illustrations of devices, adjusted to different body diameter sizes and to LV morphology, according to some embodiments of the invention.

FIGS. 6C and 6D are highly schematic illustrations of using a single pair of artificial chords, attached to the bridge, to anchor leaflet region(s), according to some embodiments of the invention.

FIGS. 7C-7F are high-level schematic illustrations of a device for implantation on the mitral valve, with non-limiting examples for dimensions and angles of various device portions, according to some embodiments of the invention.

FIGS. 7G-7J are high-level schematic illustrations of devices used in experiments, according to some embodiments of the invention.

FIGS. 7K-7Q are high-level schematic illustrations of devices for implantation on the mitral valve, having covers over at least some of its elements, according to some embodiments of the invention.

FIGS. 8A-8C are high-level schematic illustrations of devices with eyelets raised above the body and its plane, according to some embodiments of the invention.

FIGS. 9A-9H are high-level schematic illustrations of devices, according to some embodiments of the invention.

DETAILED DESCRIPTION OF THE INVENTION

Figure 1A:
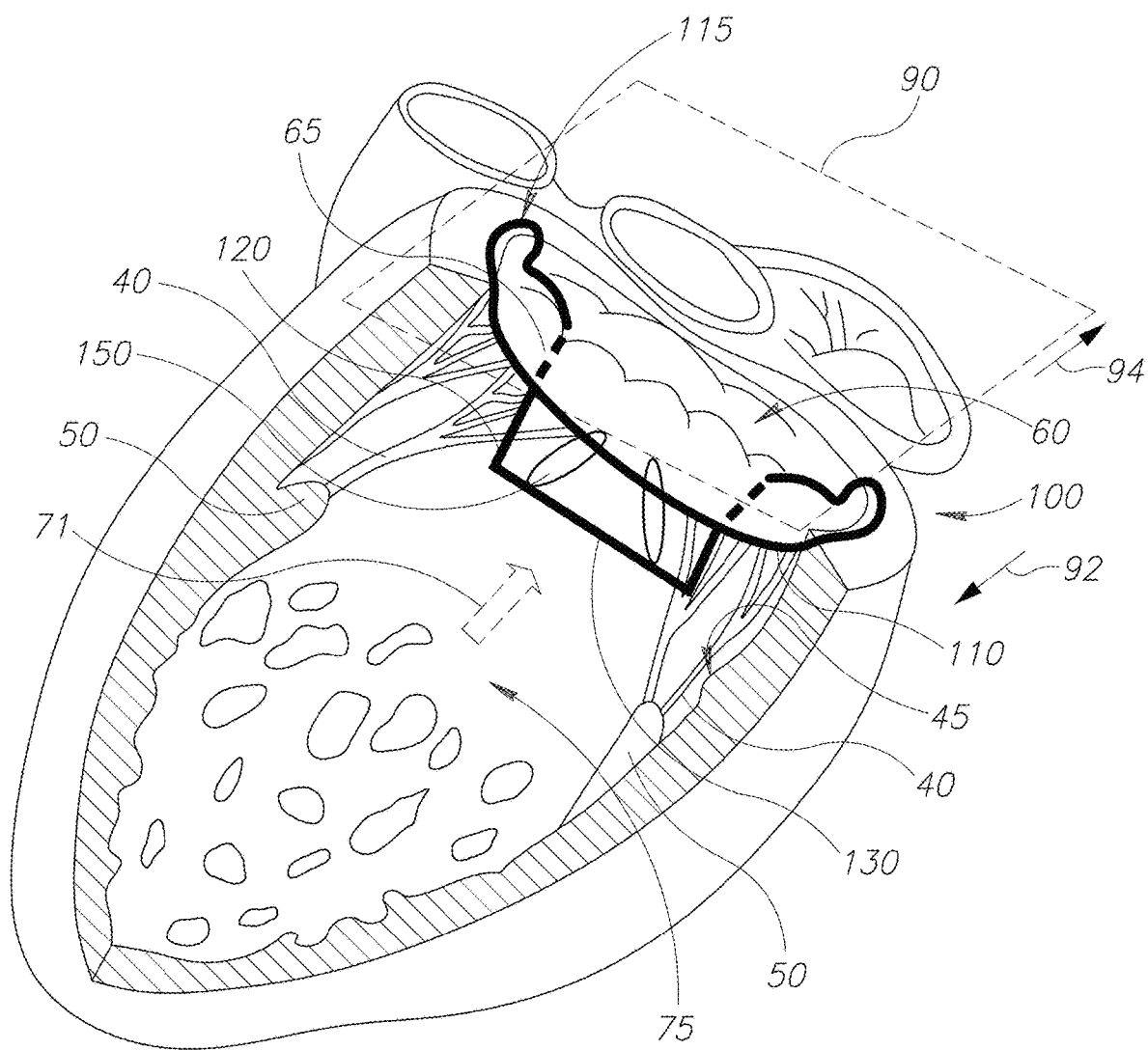
FIGS. 1A-1C are high-level schematic illustrations of the left ventricle and mitral valve anatomy and positions of devices implanted on the mitral valve, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting. As used herein the term "about" refers to ±10%.

Disclosed embodiments relate to devices and methods of correcting mitral valve insufficiency as well as valvular heart diseases causing stenosis and/or insufficiency, such as by restoring valve leaflet coaptation by plastic surgery and/or by repairing mitral valve regurgitation.

Mitral valve implants, devices, kits and methods are provided for mitral valve repair. Devices used as mitral valve implants comprise a body attachable onto the mitral valve annulus and a bridge connected to the body by two legs which are configured to support and position the bridge within a left ventricle (LV) of the patient when the device (implant) body is implanted, so that the legs and the bridge avoid contact with the LV walls, papillary muscles and chordae during operation of the heart. For example, the legs may be mechanically configured to position the bridge within a specified space in the LV which is free of chordae and papillae during heart functioning, the specified space defined by a depth between 10 mm and 30 mm below the device body, a width between 15 mm and 30 mm with respect to a median plane of the device, and a length between −5 mm and +15 mm with respect to a posterior edge of the device body.

The bridge may be used to anchor valve leaflet tissue, provide support for leaflet re-modelling, possibly using external tissue, and/or anchor artificial chords used to modify and repair the operation of the mitral valve. Related medical procedures as well as kits and related utensils are also provided.

In certain embodiments, annuloplasty devices for mitral valve repair are provided. Devices may include a ring-like body having a semi rigid/rigid posterior portion adapted to be implanted on a posterior aspect of the mitral valve annulus and an anterior portion connected to opposing legs. The legs are configured for crossing through opposing regions of a commissure of the valve when the posterior portion of the ring-like body is implanted on the posterior aspect of the mitral valve annulus. The legs are characterized in that each leg extends away from, and is angled medially and posteriorly with respect to, the ring-like body, and the legs are interconnected via a bridge, or a bar.

In certain embodiments, provided annuloplasty devices for plastic surgery of the mitral valve may be implanted in subjects affected by valvular heart diseases causing stenosis and/or insufficiency. Devices may include at least one curved body, to be implanted coplanar with the native mitral annulus, characterized in that the curved body has at least two portions extended in different planes with respect to that in which the curved body lies, adapted to assist the heart surgeon in the operations of repair of the mitral apparatus of a patient affected by stenosis and/or insufficiency, the curved body having at least two descending portions to be inserted inside the mitral orifice, adapted to provide a grip for the anchoring of a prolapsed leaflet and/or of a biological tissue biocompatible with the human organism and/or of tendinous elements, when the device is applied to the damaged mitral apparatus of a patient.

Mitral valve insufficiency can be effectively treated via, for example, implantation of annuloplasty rings which may restore leaflet coaptation via annulus reshaping. However, ring implantation alone is oftentimes less effective in the long term since both leaflets and the sub-valvular apparatus can contribute to insufficiency (e.g., myxomatous leaflets chordate elongation/rupture, altered left ventricle sphericity index). In addition, left ventricle geometry and volume might change in the post-operative period (e.g., the ventricle anatomy is restored to the non-pathological state or changes of the distance between the two papillary muscles) resulting in modification of the optimal chordae length leading to prolapse or tethering of the leaflets when the ventricle contracts. Certain embodiments minimize the negative effects of ventricular remodeling in the post-operative period, to facilitate chordae implantation and in the same time to guaranty correct length or to allow direct leaflet fixation. In particular, in patients with the myxomatous valves (Barlow disease), the posterior leaflet may be directly attached to the bridge or the bar, reducing the risk of SAM (systolic anterior motion, a known surgical risk in such patients).

Certain embodiments of disclosed annuloplasty devices may be configured according to any of the following guidelines: One or both leaflets and sub-valvular apparatus dysfunction may be addressed in order to provide short and long term results; the leaflet(s) may be anchored directly or via artificial chords to a fixed ventricle-positioned structure which is a part of the device allowing accurate assessment of artificial chord length; artificial chords may be attached to the device prior to implantation reducing ischemic time during the operation, with the ease of repair and artificial chords implantation possibly reducing ischemia when the heart is not perfused; the devices may be configured to minimize interference with leaflets and chordae and minimizes contact with the LV (left ventricle) wall; the devices may be configured to accommodate for any post-operative changes to the ventricle; the devices may be configured to be amenable to minimally invasive surgery; the devices may be configured to simplify the identification and avoidance of the papillary muscles to simplify the access and make artificial chordae implantation simpler; and the devices may be configured to enable direct implantation of artificial chordae to the papillary muscles without causing rapture and associated severe mitral regurgitation.

As is illustrated below, experimentation may be used and expanded to achieve designs that enable leaflet anchoring to the device directly or via artificial chords while minimizing or completely avoiding contact with the chordae tendineae and other heart structure (e.g., leaflets papillary muscle and myocardium).

Certain embodiments comprise an annuloplasty device for mitral valve repair. The device may include a ring-like body (open or closed with complete or partial metal core) having a posterior portion adapted to be implanted on a posterior aspect of the mitral valve annulus and an anterior portion terminating with opposing legs configured for crossing through opposing regions of a commissure of the valve. The ends of the opposing legs may be interconnected via a bridge portion. Thus, when positioned at the mitral valve, the ring like body may lie parallel to the annulus plane and the opposing legs may be at an angle thereto with the bridge positioned in the left ventricle directly below the valve opening.

According to certain embodiments, an annuloplasty device is provided for mitral valve repair, which comprises a ring-like body having a posterior portion adapted to be implanted on a posterior aspect of the mitral valve annulus and an anterior portion connected to opposing legs being configured for crossing through opposing regions of a commissure of the valve when the posterior portion of the ring-like body is implanted on the posterior aspect of the mitral valve annulus, each of the opposing legs extends away from, and is angled medially and posteriorly with respect to, the ring-like body.

In some embodiments, a posterior angle of a first leg of the opposing legs is greater than the angle of a second leg. In some embodiments, the anterior portion is open with each end transitioning to a leg of the opposing legs. In some embodiments, the distal ends of the opposing leg are interconnected via a bridge. In some embodiments, the posterior angle of the first leg is greater by 5-20° than the angle of the second leg. In some embodiments, each end of the anterior portion transitions to the leg through a series of inward, backward and downward bends. In some embodiments, a first leg of the opposing legs crosses through a postero-medial commissure and a second leg crosses through an antero-lateral commissure. In some embodiments, the posterior portion of the ring-like body is curved at a radius of 10-20 mm. In some embodiments, the distance from the posterior end of the ring-like body to the commissures ranges between 3 to 9 mm. In some embodiments, the inward bend has a radius of curvature of 0.5-1.5 mm.

In some embodiments, the device further comprising a cuff covering the ring. In some embodiments, the device further comprises a cuff covering the bridge. In some embodiments, the device further comprises a cuff covering at least a portion of the legs. In some embodiments, the cuff includes a first polymeric layer and a second fabric layer. In some embodiments, the first polymeric layer is made of silicone. In some embodiments, the polymer is covered with a fabric (e.g., polyester). In some embodiments, the polymer is covered with a fabric (e.g., PTFE, polytetrafluoroethylene or expanded PTFE). In some embodiments, the ring-like body is fabricated from a wire having a diameter of 0.5-1.5 mm. In some embodiments, the wire is composed of stainless steel, nitinol or a cobalt chromium alloy.

In some embodiments, the distance between the bridge and the ring-like body is 5-30 mm. In some embodiments, each of the opposing legs is bent at a middle portion thereof. In some embodiments, the length of each of the opposing legs is in a range of 15-35 mm. In some embodiments, the bridge length is proportional to the ring size, and may be 15-35 mm.

According to certain embodiments, an annuloplasty device is provided for mitral valve repair, which comprises a ring-like body having a posterior portion adapted to be implanted on a posterior aspect of the mitral valve annulus and an anterior portion connected to opposing legs being configured for crossing through opposing regions of a commissure of the valve when the posterior portion of the ring-like body is implanted on the posterior aspect of the mitral valve annulus, wherein a length and a medial and posterior angle of the legs is selected so as to enable a bridge interconnecting the legs to reside within a rectangular volume defined by: 25×15×9 mm when the rectangular volume is positioned 5 mm below, with a 2-5 mm (preferably 5 mm) posterior offset to, the ring-like body.

According to certain embodiments, a method of treating mitral valve insufficiency is provided, and comprises at least some of the following stages: providing an annuloplasty device having a posterior C-shaped portion and an anterior portion terminating with opposing legs interconnected via a bridge; and anchoring the posterior C-shaped portion of the device on a posterior aspect of the mitral valve annulus such that the opposing legs cross through opposing regions of a commissure of the valve and extend away from, and angle medially and posteriorly with respect to, the posterior portion. In some embodiments, the ring-like body is configured to span, once implanted, the antero-lateral and postero-medial trigones and then curve backwards to the commissures with the legs crossing at the commissures. The vertical distance from the curve end to the descending legs may range between 3-8 mm.

In some embodiments, the method further comprises suturing the bridge to at least one leaflet of the mitral valve. In some embodiments, the method further comprises attaching the bridge directly to the at least one leaflet of the mitral valve using a running suture. In some embodiments, the method further comprises attaching the bridge to the at least one leaflet of the mitral valve using artificial chords. In some embodiments, the method further comprises attaching the bridge to the inferior left ventricle wall using a trans-wall suture.

According to certain embodiments, an annuloplasty device is provided for mitral valve repair, which comprises a ring-like body having a posterior portion adapted to be implanted on a posterior aspect of the mitral valve annulus and a pair of opposing legs being configured for crossing through opposing regions of a commissure of the valve when the posterior portion of the ring-like body is implanted on the posterior aspect of the mitral valve annulus, each of the opposing legs extending away from the ring-like body and angled medially and posteriorly with respect to, the ring-like body. In some embodiments, each of the opposing legs extends directly from the ring-like body.

Certain embodiments comprise versatile devices for plastic surgery of the mitral valve, which allow operating with success on the damaged mitral apparatus even in the cases in which a formidable calcification of the mitral annulus has been found, deep in the myocardium (e.g., avoiding valve substitution with the associated risk of perforating the myocardium). The devices may be configured to reduce the probability of damaging heart tissue during implantation as well as thereafter, during the operation of the heart. Certain embodiments enable repairing the damaged mitral apparatus without necessarily having to operate on the ventricular bottom, possibly at the height of papillary muscles and/or on the tendinous cords (which are hard to achieve with current technology).

Figure 1B:
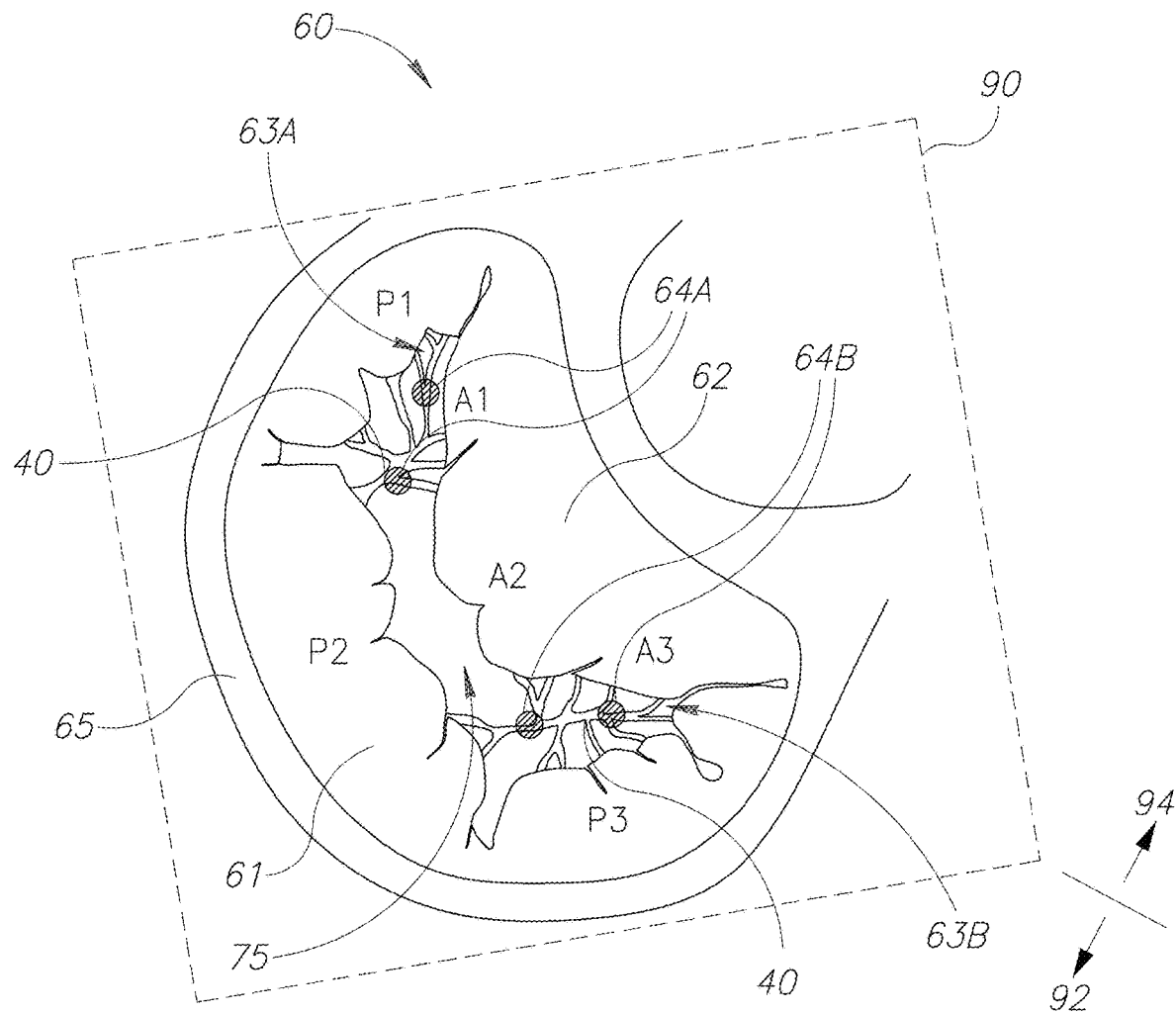
Figure 1C:
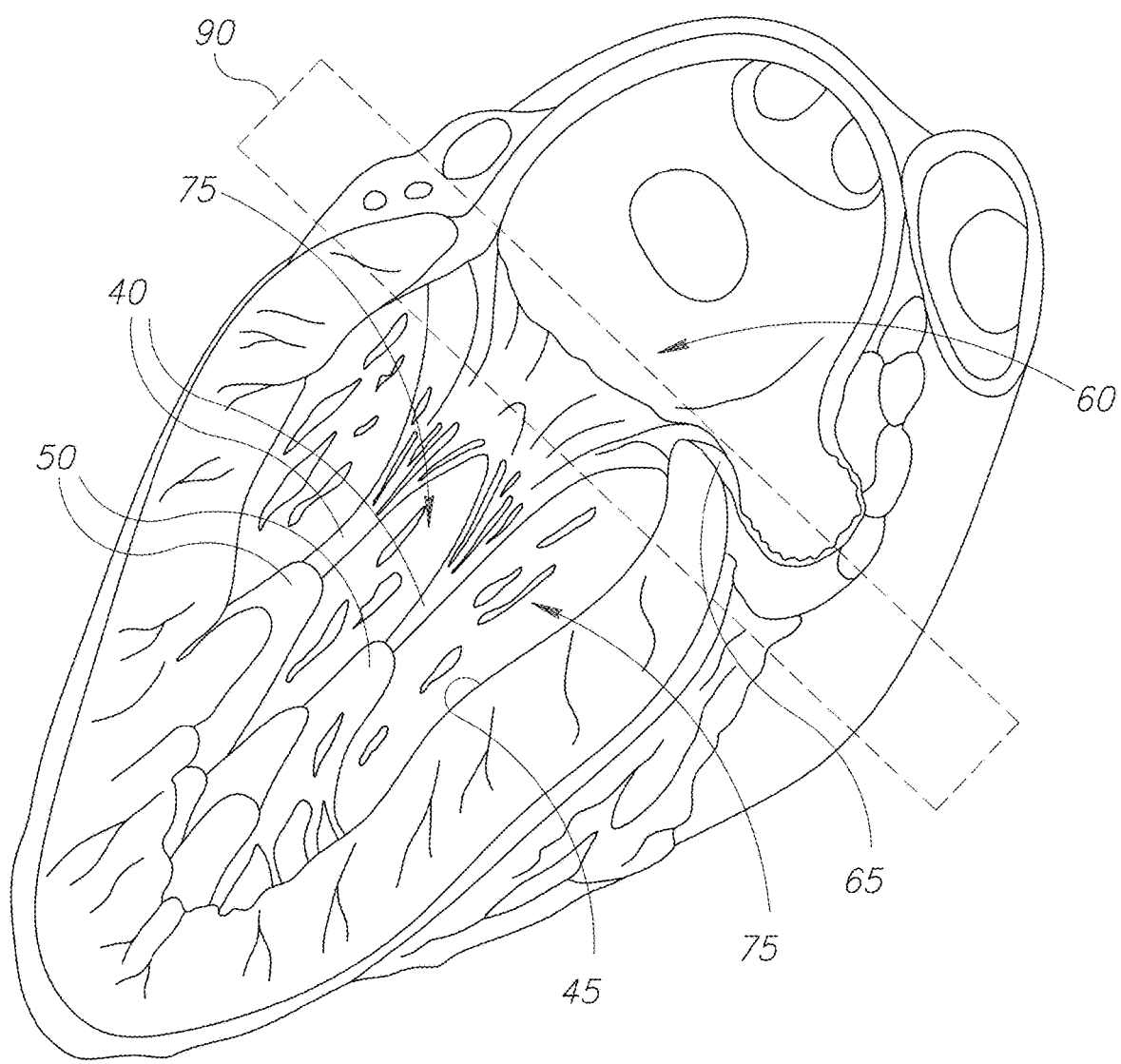
Figure 1E:
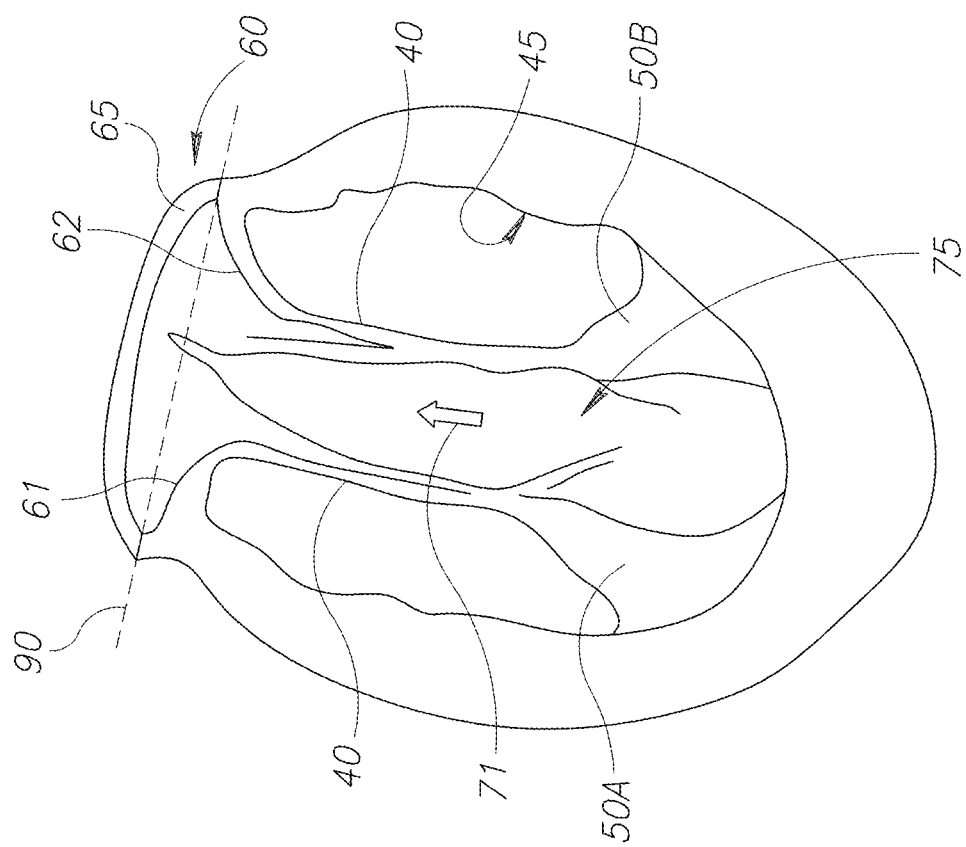
FIGS. 1D and 1E respectively show the left ventricle (LV) of a human heart in which the mitral valve functions correctly, and the left ventricle of a human heart in which the mitral valve functions incorrectly caused by an insufficiency due to the excessive dilation of LV in question.
Figure 1D:
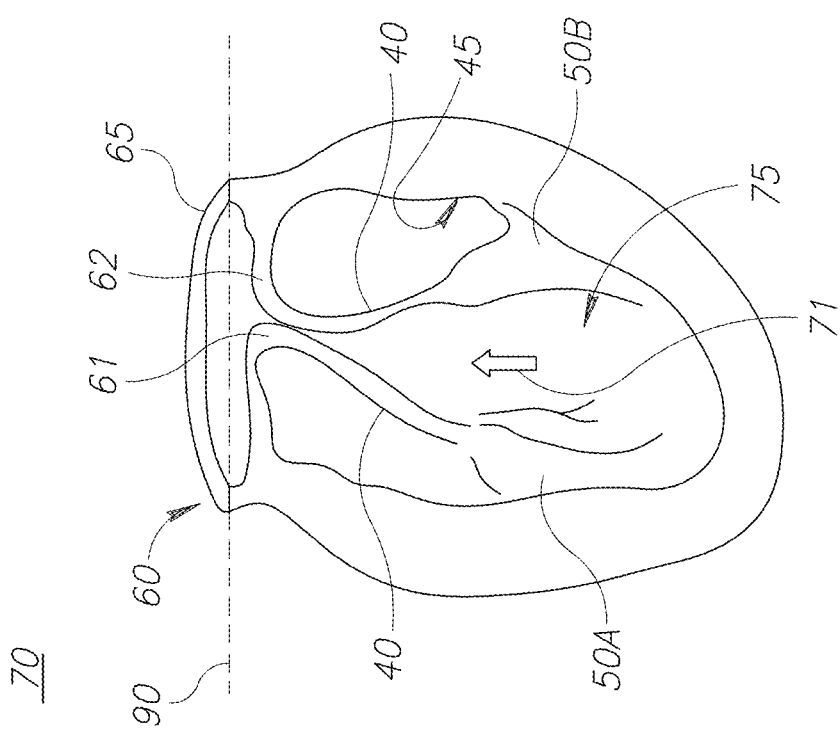

FIGS. 1A-1C are high-level schematic illustrations of the left ventricle and mitral valve anatomy and positions of device 100 implanted on the mitral valve, according to some embodiments of the invention. FIG. 1A illustrates schematically positioning of device 100 within a longitudinal cross-section of the heart, while FIGS. 1B and 1C illustrates a top and longitudinal cross section views, respectively, of the mitral valve with device (implant) body 110 positioned thereupon. FIGS. 1D and 1E illustrate schematically heart conditions in which device 100 may be applied, according to some embodiments of the invention.

Device 100 may be positioning at the mitral valve, e.g., as illustrated schematically in the non-limiting examples of FIGS. 1A and 1C. Ring-like body 110 may be positioned at the atrial side of the valve while legs 120 and bridge 130 may be positioned at the ventricular side of the valve. Ring-like body 110 may be anchored to the posterior aspect of the mitral valve annulus (e.g., by suturing cuff 142, which is described below with respect to FIGS. 7K-7Q, to annulus tissue) to secure device 100 in position. Artificial chords 150 may be attached between bridge 130 and posterior and/or anterior leaflets (e.g., sutured to cuff 144, which is described below with respect to FIGS. 7K-7Q, and leaflets). Artificial chords 150 may be surgical sutures (e.g., ePTFE or polypropylene). Devices 100 may be applied to hearts with a left ventricle that functions pathologically due to an excessive dilation of the ventricle itself.

In various embodiments, devices 100 may be configured with respect to the range of variability in heart and mitral valve morphology, as provided e.g., in Ho 2012 (Anatomy of the mitral valve, Heart 2002:88(Suppl IV): iv5-iv10). Devices 100 may either be pre-configured with respect to specific patient heart anatomy, and/or be configured to be adjusted to specific patient heart anatomy during the medical implantation procedure.

In the following description, initial experimental results are presented, in which devices 100 were implanted in porcine and ovine hearts. While porcine and ovine hearts are quite similar to human hearts and are considered adequate models thereto (see, e.g., Degandt et al., 2007, Mitral valve basal chordae: comparative anatomy, The Annals of Thoracic Surgery 84:1250-5), it is emphasized that devices 100 may be configured with respect to the range of variability in heart and mitral valve morphology of human patients, according to the disclosed principles, and are not limited to device structures disclosed herein as being used in the experiments in porcine and ovine hearts.

Several prototypes were constructed and tested ex-vivo on a porcine heart (about 500 gm) mounted on a mock loop passive beating heart test platform. The heart was inflated with water and the anatomy was measured using common approaches. The valve was measured using a mitral valve sizer, the prototypes were placed on the valve annulus and the LV (left ventricle) was filled with water.

In various configurations of experimental devices, models of device 100 were prepared with inwards angles $\gamma 1$, $\gamma 2$ of legs 120 of 15° and 30° (see, e.g., FIG. 7D and the related description), leg lengths of 15, 17.5 and 20 mm, and backwards (posterior) angles $\alpha 1$ of legs 120 to annular plane 90 of between 90° and 60° (see, e.g., FIG. 7C and the related description). Additional examples for devices 100 are provided, e.g., in FIGS. 2A-2D and 3A-3L below.

Several insights were gained from these ex-vivo experiments. The length of legs 120, and distance between bridge 130 and ring-like body 110 and/or plane 90 should be selected such that coaptation is above bridge 130 and legs 120 do not touch the papillary muscle. A distance of 20 mm between bridge 130 and plane 90 was found to be optimal in these experiments. Clearly, the distance may be adapted according to the human heart morphology, possibly with reference to specific patients. Legs 120 may angle backward α1 (to posterior to ring-like body 110) such that they angle towards the heart wall in order to enable free movement of the anterior leaflet. An inward angle of 10° (α1=80°) was found to be effective in some of the experiments. Clearly, the angles may be adapted according to the human heart morphology, possibly with reference to specific patients.

Figure 2A:
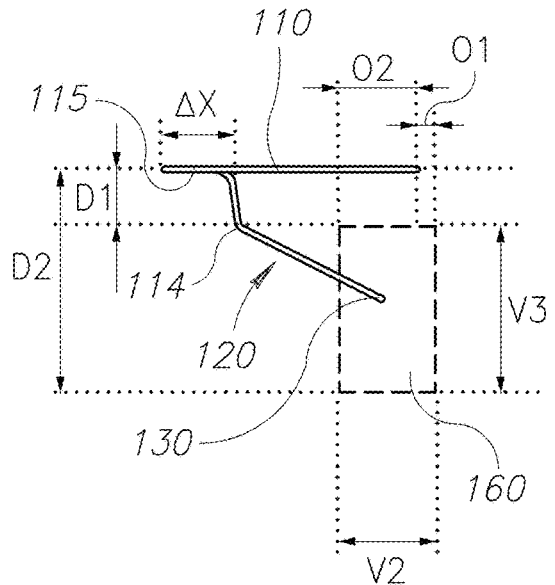
FIGS. 2A-2D are high-level schematic illustrations of devices with respect to the position of the bridge, according to some embodiments of the invention.
Figure 2B:
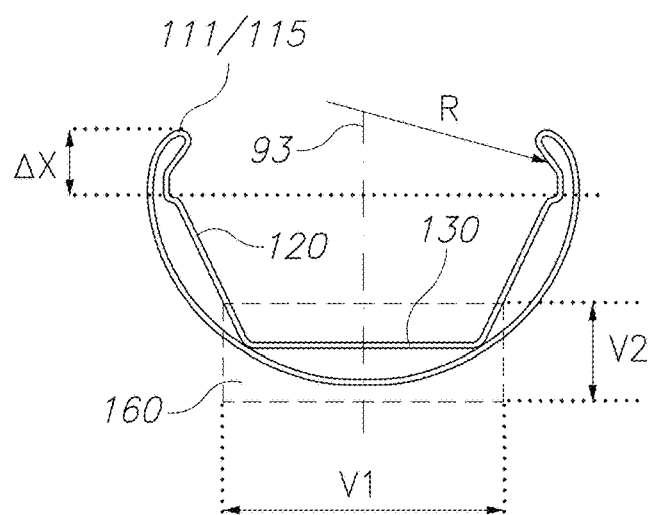
Figure 2C:
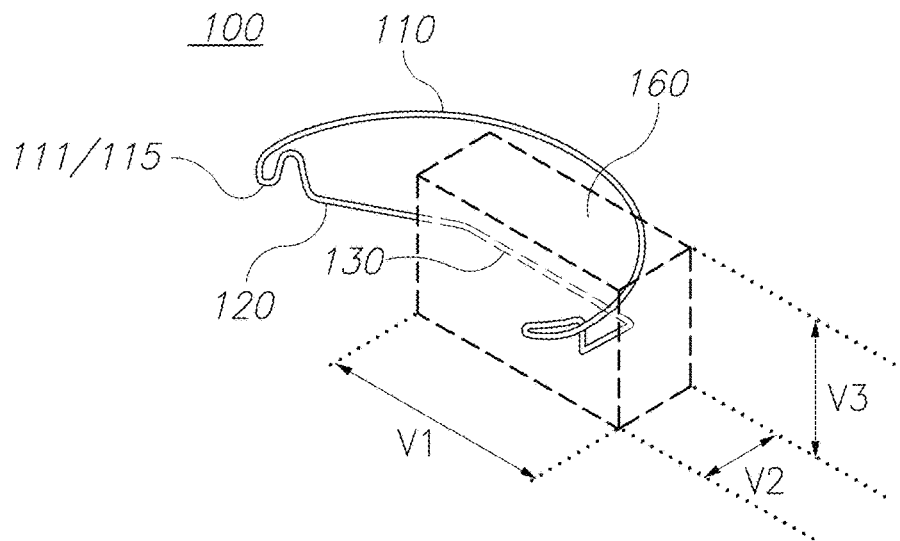
Figure 2D:
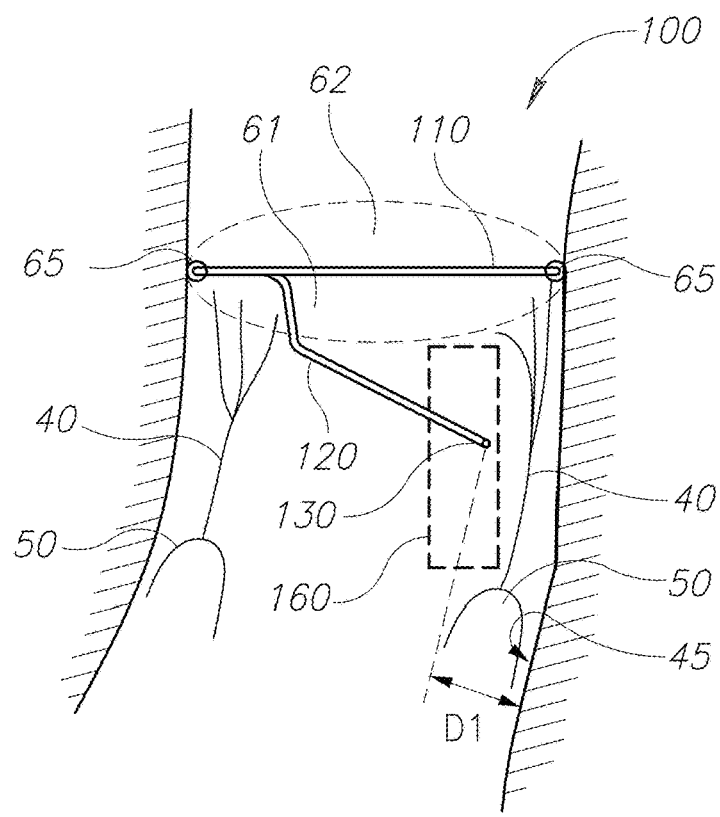

FIGS. 2A-2D are high-level schematic illustrations of device 100 with respect to the position of bridge 130, according to some embodiments of the invention. FIGS. 2A and 2D are side views, FIG. 2B is a top view and FIG. 2C is a perspective view. Experiments have emphasized the importance of the position of bridge 130 with respect to ring-like body 110 and/or plane 90. Since mitral valve anatomies vary between patients, some variability in the position of bridge 130 is expected. By modeling of the mitral valve, the present inventor has been able to determine the variability needed in bridge position that can provide the aforementioned functionality of devices 100 in a wide range of patient anatomies. As is shown in FIGS. 2A-2D, the position of bridge 130 may be determined by positioning device 100 with respect to a virtual rectangular space (VRS) 160, denoted schematically as having the dimensions V1 (width), V2 (length) and V3 (height). Clearly, future designs may comprise a more refines definition of VRS 160, possibly not rectangular and further adapted to left ventricle morphology. In a non-limiting example, VRS 160 may have V3=25 mm, V1=35 mm and V2=20 mm, and may be positioned at depth D below plane 90, e.g., with D1=5 mm below the plane of ring-like body 110, reaching a lower boundary of D2=D1+V3, and with a posterior offset O1 with respect to an edge of body 110, e.g., O=2 to 5 mm, positioning the anterior edge of VRS 160 at O2=V2−O1 from the posterior edge of body 110 (e.g., O2=7 mm), for example, as illustrated schematically in FIG. 2A. The position of bridge 130 is associated with the length and angles of legs 120, as defined herein. Backward angle(s) α1, α2 of legs 120 may be derived from the length of legs 120 and their vertical distance from annulus 65 and/or from e.g., the anterior end of ring-like body 110. FIG. 2D illustrates schematically the definition of specified space 160 (VRS) as the spatial region in which bridge 130 is allowed, avoiding contact with LV wall 45, papillary muscles 50 and chordae 40 during operation of the heart and contraction and expansion of LV 70.

Advantageously, with respect to prior art such as U.S. Patent Application Publications Nos. 20040127982 and 20120179247, disclosed devices 100 have legs 120 entering LV 70 through the commissures or adjusted positions, have some flexibility which participate in heart operation, provide bridge 130 as anchoring structure for artificial chords and is configured to avoid prior art detrimental contact to LV wall 45, papillary muscles 50 and/or chordae 40 during heart operation.

Certain embodiments comprise device 100 comprising body 110 configured to be attached and implanted onto annulus 65 of a patient's mitral valve 60, and a bridge 130 connected to body 110 by two legs 120 which are configured to support and position bridge 130 within left ventricle (LV) 75 of the patient when device body 110 is implanted. Legs 120 are mechanically configured to position bridge 130 within a specified space 160 (such as VRS 160) in LV 75 which is free of chordae 40 and papillae 50 during heart functioning. For example, specified space 160 may be defined by a depth between 10 mm and 35 mm below device body 110, a width between 15 mm and 30 mm with respect to a median plane 93 of device 100, and a length between −5 mm and +15 mm with respect to a posterior edge of device body 110. In certain embodiments, the depth below device body 110 may be between D1 and D2, as illustrated e.g., in FIG. 2A; the width with respect to median plane 93 of device 100 may be V1, as illustrated e.g., in FIGS. 2B and 2C; and the length with respect to a posterior edge of device body 110 may be V2, as illustrated e.g., in FIG. 2B, with −5 mm relating to a more posterior position of bridge 130 with respect to the posterior edge of device body 110.

In certain embodiments, device body 110 and/or legs 120 and/or bridge 130 may be made of one bended material loop including corresponding bends. In certain embodiments, at least one of body 110, legs 120 and bridge 130 may be covered by at least one of ePTFE, dacron and pericardial tissue. In certain embodiments, legs 120 may be angled towards the posterior direction with respect to a longitudinal plane going through connection points (e.g., the posterior edges of eyelets 115) of legs 120 to body 110 (see e.g., backward angle α1). For example, legs 120 may be configured to divert bridge 130 at a posterior angle of 30-80° with respect to annular plane 90 (and/or the body plane), e.g., possibly at a posterior angle of 40-60°, or 50° with respect to annular plane 90 (and/or the body plane. For example, legs 120 may comprise one or more bend(s) 114 in posterior direction 92 to achieve backward angle α1, by bend(s) 114 alone or in addition to a tilt of legs 120.

In certain embodiments, legs 120 may be connected to body 110 at points configured to introduce legs 120 into LV 75 through the anterolateral and the posteromedial commissures (63A and 63B, respectively, in FIG. 1B, corresponding to the anterolateral and the posteromedial papillary muscles 50A and 50B, respectively). Corresponding entry points 64A, 64B, corresponding to commissures 63A, 63B are illustrated schematically in FIG. 1B, with two alternative embodiments indicated for each entry point 64A, 64B, one at the respective commissure and the other at some distance from the respective commissure, as explained below. Intermediate entry points provide additional embodiments and may depend on the condition of the mitral valve and the treated condition as well as relate to the structure of device 100. In certain embodiments, legs 120 may be connected to body 110 at points configured to offset at least one of the entry points of the legs into the LV with respect to the anterolateral and the posteromedial commissures by 2-8 mm in the posterior direction.

In certain embodiments, legs 120 may be connected to body 110 by two eyelets 115 configured to be attached to annulus 65. Eyelets 115 and body 110 may be in one plane (e.g., annular plane 90) or eyelets 115 may be raised above plane 90 of device body 110 to tilt device 110 by specified angle β3 (see, e.g., FIG. 8A) between 5-20° with respect to plane 90 and/or with respect to annulus 65.

In certain embodiments, device 100 may further comprise at least one pair of artificial chords 150 attached to bridge 130 and configured to fixate leaflet tissue to bridge 130 (see, e.g., FIGS. 1A, 6C, 6D, 6F). In certain embodiments, bridge 130 may be configured to enable attachment of leaflet tissue thereto.

Certain embodiments comprise kit(s) 180 (see e.g., FIG. 3J-3N and related description) comprising one or more device(s) 100, at least one pair of artificial chords 150 attached to bridge 130 of device 100; and in a temporary way to a holder 170 (see e.g., FIG. 5 and related description) that may be configured to support device 100 during the implantation onto annulus 65. Holder 170 may have a holder body 172 configured to be releasably attached to device 100 and a handle 174 connected to holder body 172 in a direction opposite to bridge 130 with respect to device body 110. Holder body 172 may comprise a slit 173 through which artificial chords 150, which are connected to bridge 130, are passed; and handle 174 may comprise a support 175 to which artificial chords 150, that are passed through slit 173, are temporarily attached during the implantation. Once device 100 is positioned correctly in the heart cavities, support 175 retaining chords 150 may be removed from holder 174 to simplify suturing chords 150 to corresponding heart tissue. Following the attachment procedure, once device 100 is correctly positioned and attached to annulus 65 and chords 150 are properly applied, holder 170 may be detached and removed from device body 110.

In certain embodiments, kit(s) 180 may comprise a plurality of devices 100 and associated cords 150, with device bodies 110 having different diameters, while in all devices 110, bridge 130 is set within specified space 160 with respect to the corresponding device body 110.

Certain embodiments comprise medical procedures (see method 200 and FIG. 12 below) of treating the Barlow syndrome by implanting body 110 of device 100 onto annulus 65 and fixating leaflet tissue to bridge 130. Certain embodiments of medical procedures comprise implanting body 110 of device 100 onto annulus 65A and connecting leaflet tissue by at least one pair of artificial chords 150 to bridge 130.

Certain embodiments of medical procedures comprise connecting legs 120 to device body 110 at points configured to offset at least one of the entry points of legs 120 into LV 75 with respect to the anterolateral and the posteromedial commissures by 2-8 mm in the posterior direction, wherein the medical procedure is adjusted to treat ischemic mitral regurgitation.

Certain embodiments of medical procedures comprise using a single pair of artificial chords 150 attached to bridge 130, and further comprise performing the connecting by zig-zagging the artificial chords between the bridge and the leaflet tissue, to equalize tension along the cords (see FIGS. 6C and 6D below).

Figure 3G:
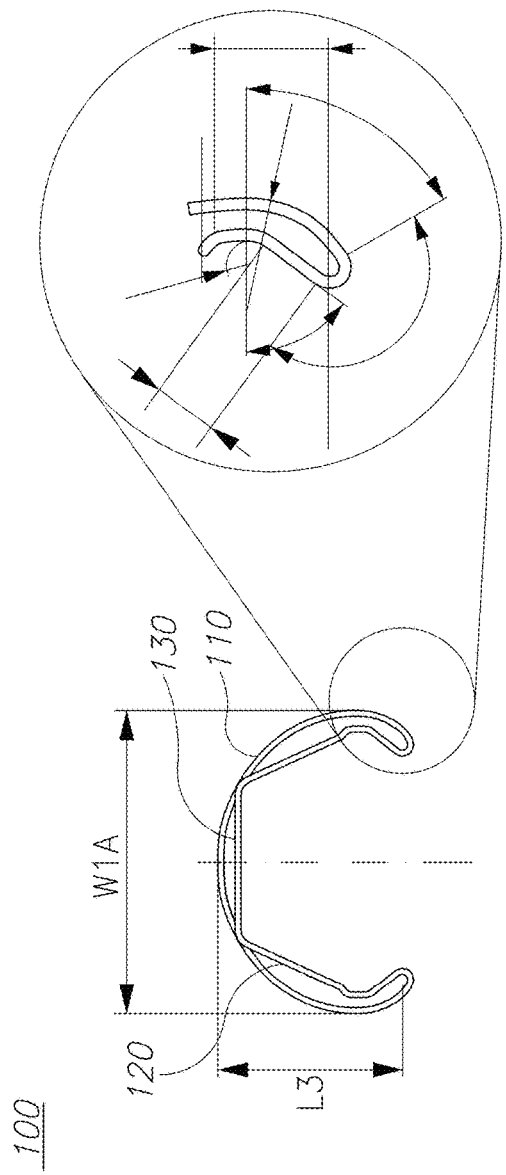
Figure 3I:
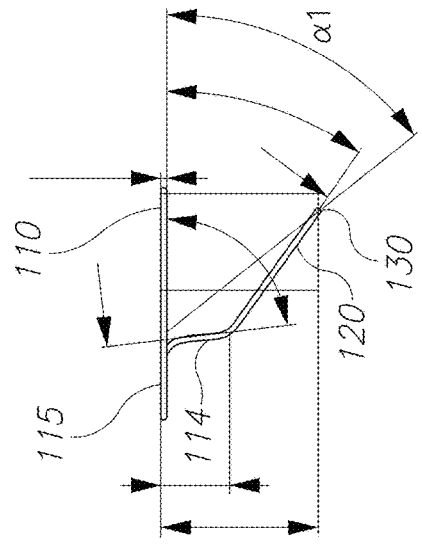
Figure 3H:
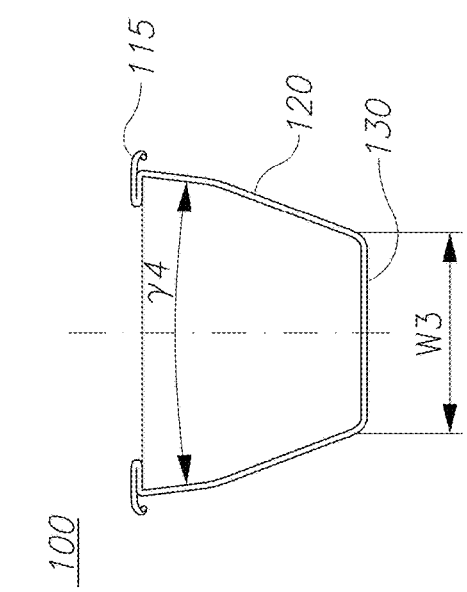
Figure 3L:
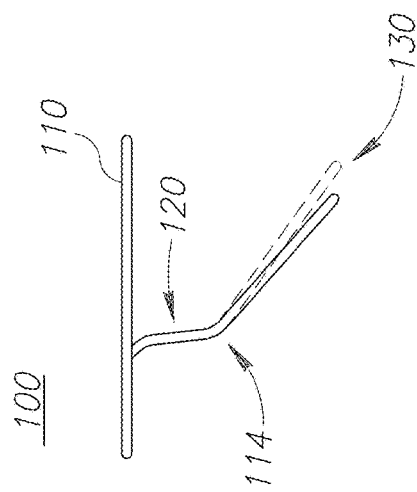
Figure 3M:
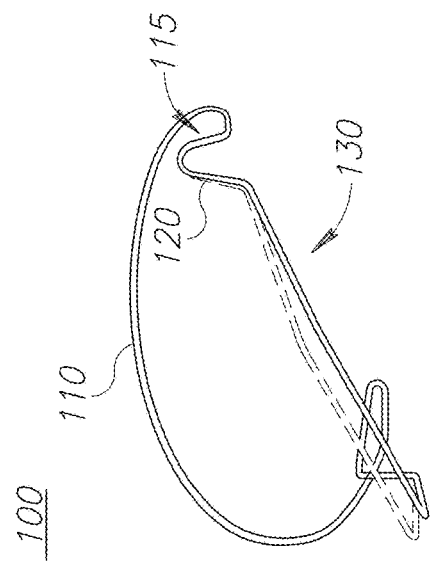
Figure 3J:
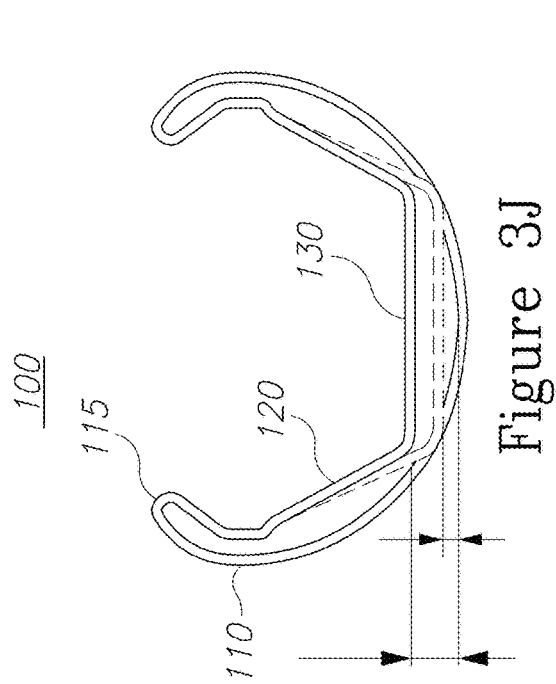
Figure 3K:
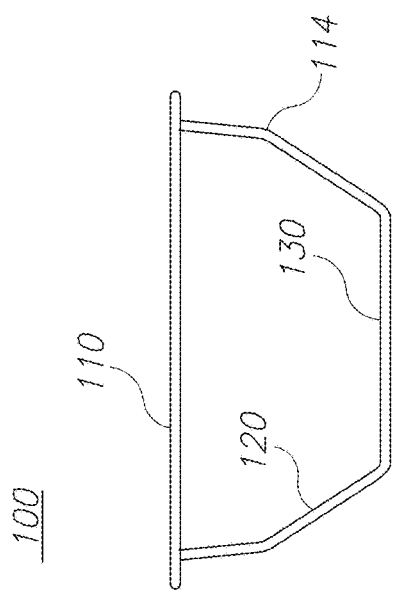
Figure 3N:
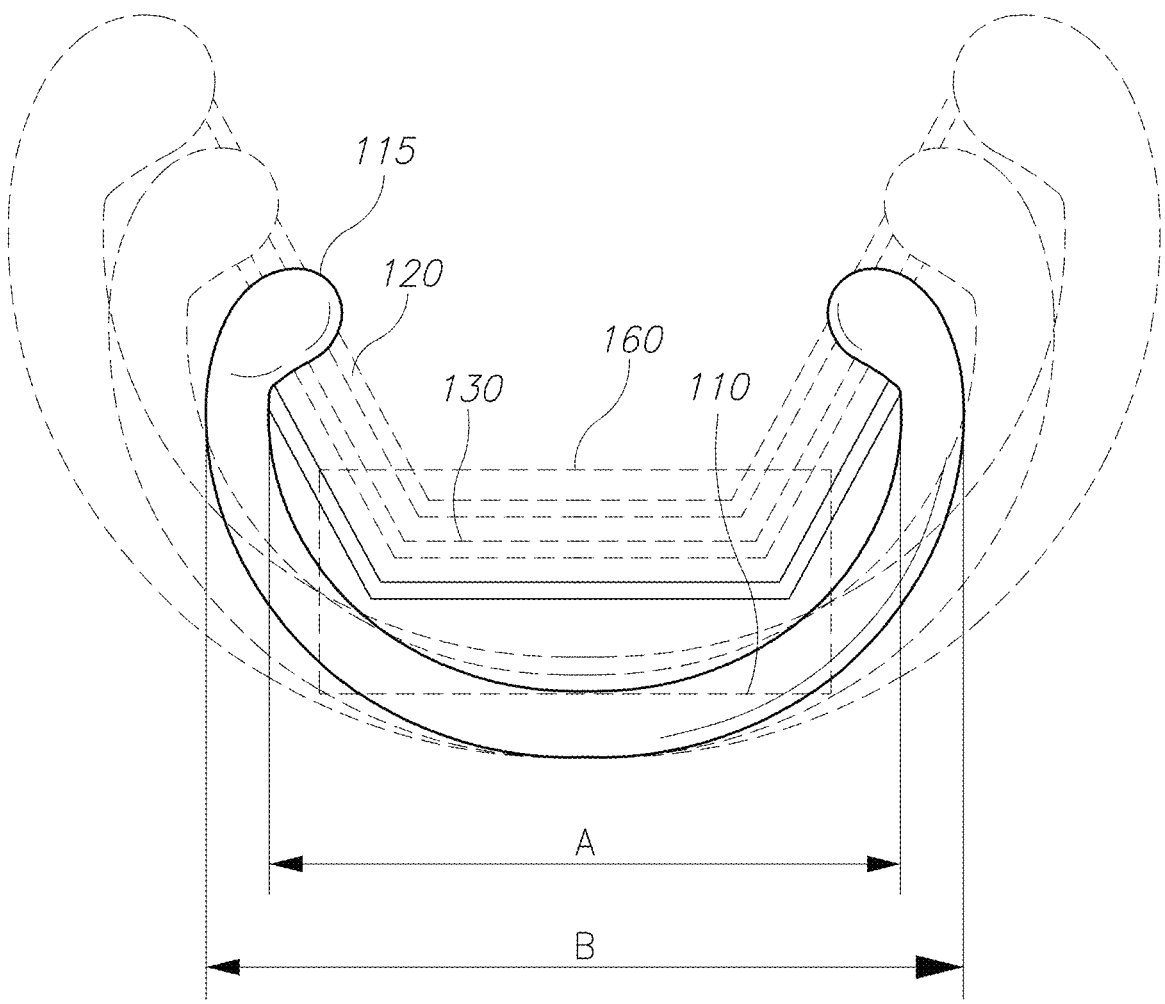
FIG. 3N is a highly schematic illustration of device bodies, which may be designed similar to prior art mitral devices configured to be anchored onto the annulus, and corresponding kits with multiple sizes of devices, according to some embodiments of the invention.

FIGS. 3A-3N are schematic illustrations of devices 100, adjusted to different body diameter sizes and to LV morphology, according to some embodiments of the invention. FIGS. 3A, 3D, 3G and 3J are top views, FIGS. 3B, 3E, 3H and 3K are front views, and FIGS. 3C, 3F, 3I and 3L are side views, and FIG. 3M is a perspective view, with FIGS. 3J-3M illustrating two superimposed devices 100, to illustrate the configurational adjustments applicable with respect to patient anatomy and/or different device sizes, e.g., as in kit 180. FIGS. 3J-3M illustrate comparisons of devices 100 indicating a part of the configuration range defined by the specified space (VRS 160, see also FIGS. 2A-2D and 8C). In certain embodiments, multiple devices 100 as illustrated in FIGS. 3A-3N, with the dimensions of legs 120 and bridge 130 adjusted according to the size (e.g., diameter) of body 110, may be included in kit 180, to be fitted to corresponding patients. In certain embodiments, the range of the inter-commissural diameter of device bodies 110 in kits 180 may be between 26 and 40 mm (indicated schematically as inner diameter A and/or outer diameter B). For example, in certain embodiments, kits 180 may comprise sets of devices with stepped diameters of device bodies 110, e.g., from 26 or 26 mm at steps of 2 or 3 mm increasing diameters. As illustrated schematically in FIG. 3N, the corresponding dimensions of legs 120 and bridge 130 as well as their angles and bends, may be modified to correspond to the device body diameter, to maintain the bridge within specified space 160.

Examples of produced devices 100 used for experimental studies include ranges of inward angles α4 of 0°, 10°, 15°, 20° and 30°, ranges of leg length between 15 and 25 mm (leg length may reach 35 mm in some embodiments), with bends 114 at ¼-⅓ of leg length, ranges of backward angles α1 of 52°, 56°, 60°, 70° and 80°, and posterior displacement of eyelets from the commissural entry points to LV of 0, 5 and 8 mm (±2-3 mm). Device thickness was any of 0.5 mm, 0.7 mm and 1 mm with optional silicone coating of ca. 1 mm and/or Dacron coating of ca. 1 mm, e.g., as cuffs 140 (e.g., cuffs 142, 144).

As noted above, kit(s) 180 may comprise multiple devices 100 with different sizes of device body 110 and corresponding modifications in the parameters of legs 120 and bridge 130 that maintain bridge 130 within the predefined specific space that prevents contact of bridge 130 with any of LV walls 45, papillary muscles 50 and natural chordae 50 during operation of the heart.

FIG. 3N is a highly schematic illustration of device body 110, which may be designed similar to prior art mitral devices configured to be anchored onto annulus 65, and corresponding kits 180 with multiple sizes of devices 100, according to some embodiments of the invention. Kits 180 may comprise multiple devices 100 (indicated schematically in broken lines, with corresponding device bodies 110, legs 120, bridges 130 and optionally artificial chords 150), having different sizes that correspond to different dimensions of patients' mitral valves 60 and annuli 65. Internal and external diameters of body 110 may vary, as well as leg lengths, angles and bends and bridge length and position. All devices 100 within kit(s) 180 may have the resulting position of bridge 130 with respect to LV geometry in common, avoiding contact of bridge 130 and legs 130 with LV walls 45, papillary muscles 50 and chordae 40. Device body may have a 3:4 ratio of width to length.

Figure 4D:
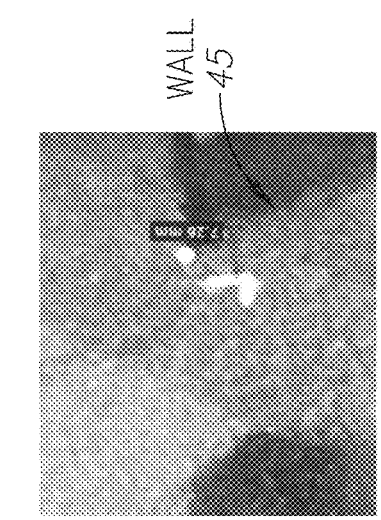
FIGS. 4A-4E present examples for CT images of devices implanted in bovine hearts, according to some embodiments of the invention.
Figure 4E:
Figure 4B:
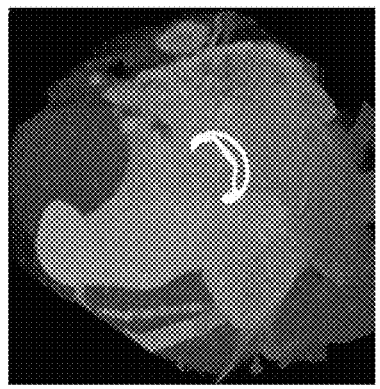
Figure 4C:
Figure 4A:
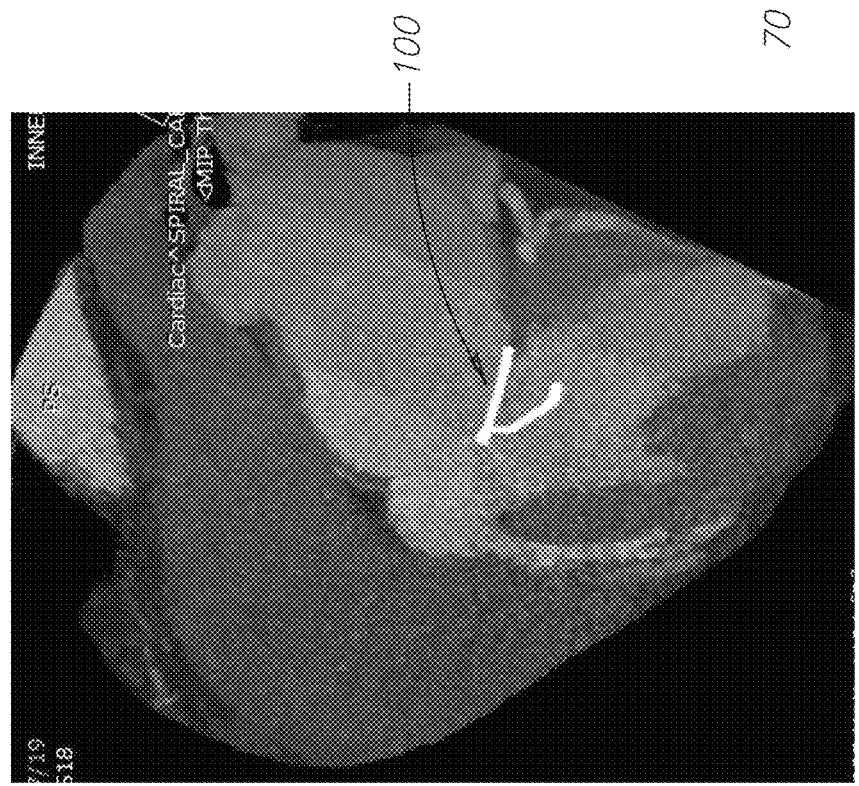

FIGS. 4A-4E present examples for CT images of devices 100 implanted in bovine hearts, according to some embodiments of the invention. FIG. 4A illustrates device 100 in situ in side view, FIG. 4B illustrates device 100 in situ in top view, FIG. 4C illustrates device 100 in situ in top perspective view, and FIGS. 4D and 4E illustrate detailed views of device 100, with annotated implantation conditions. It is noted that device 100 is implanted in a way that positions bridge 130 (and legs 120) outside of contact range with LV structures, such as LV wall 45, papillary muscles 50 and chordae 40 in LV 70. For example, FIG. 4D indicates a distance of 7.26 mm between bridge 130 and LV wall 45 in systolic state.

Figure 5:
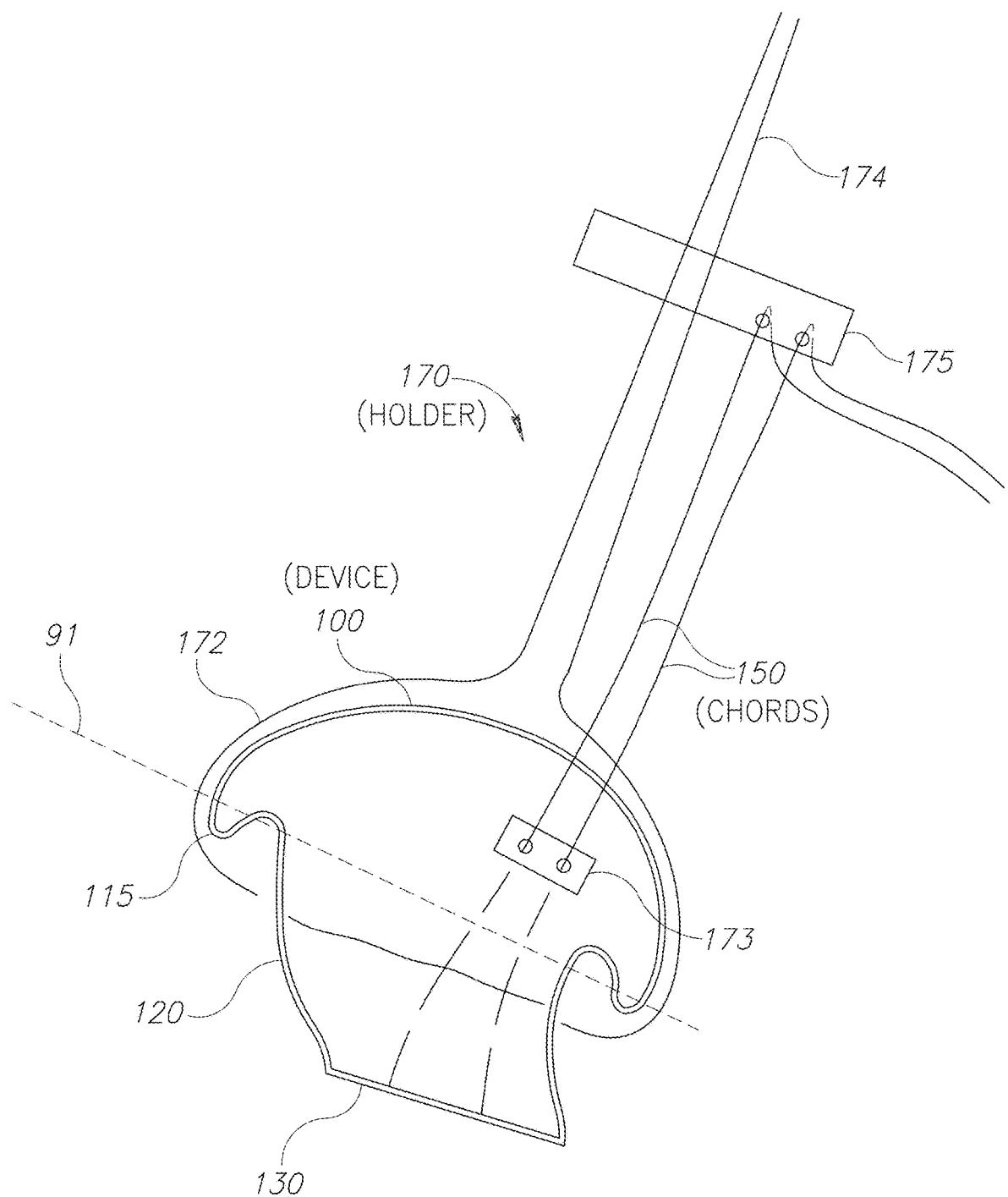
FIG. 5 is a high-level schematic illustration of a device holder, according to some embodiments of the invention.

FIG. 5 is a high-level schematic illustration of device holder 170, according to some embodiments of the invention. Holder body 172 is configured to hold and release in a controllable manner device 100 once attached to annulus 65. Holder body 172 may comprise slit 173 through which artificial chords 150 are passed to support 175 on handle 174 for temporarily holding them through the medical procedure, to simplify handling artificial chords 150. In certain embodiments, support 175 may be detachable from handle 174 and/or movable along handle 174 to simplify chord handling. Support 175 may be attached on one, two or multiple sides of handle 174 to allow the physician to temporarily support chords 150 according to convenience, possibly changing the location of the temporary hold if needed. Artificial chords 150 (and/or pairs thereof) may be color-coded and/or supported on support 175 and specified places and/or with respective marks which specify and help distinguish among chords 150 during operation, and/or prevent entanglement of chords 150 during the implantation of device body 110.

Figure 6A:
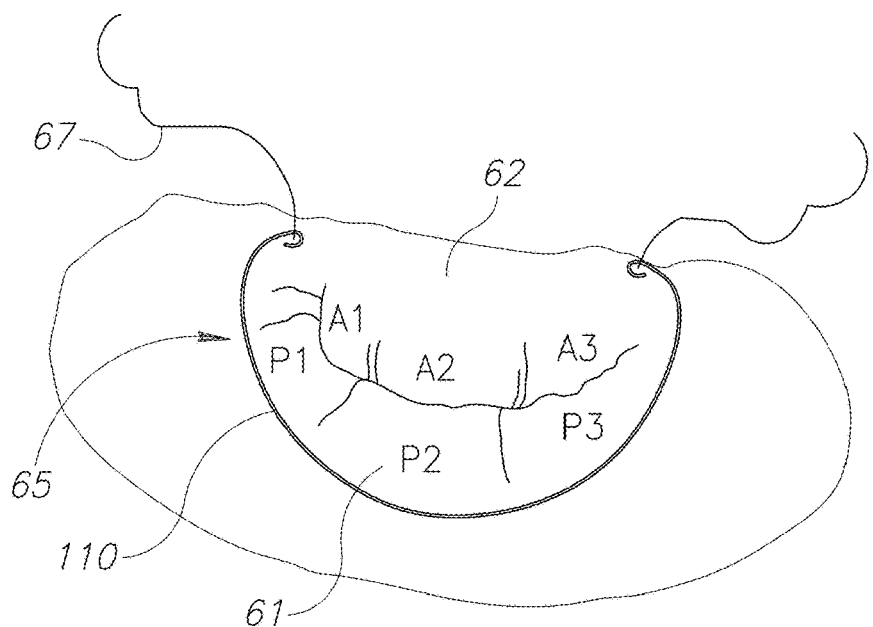
FIGS. 6A and 6B are highly schematic illustrations of the attachment of the device body to the annulus, according to some embodiments of the invention.
Figure 6B:
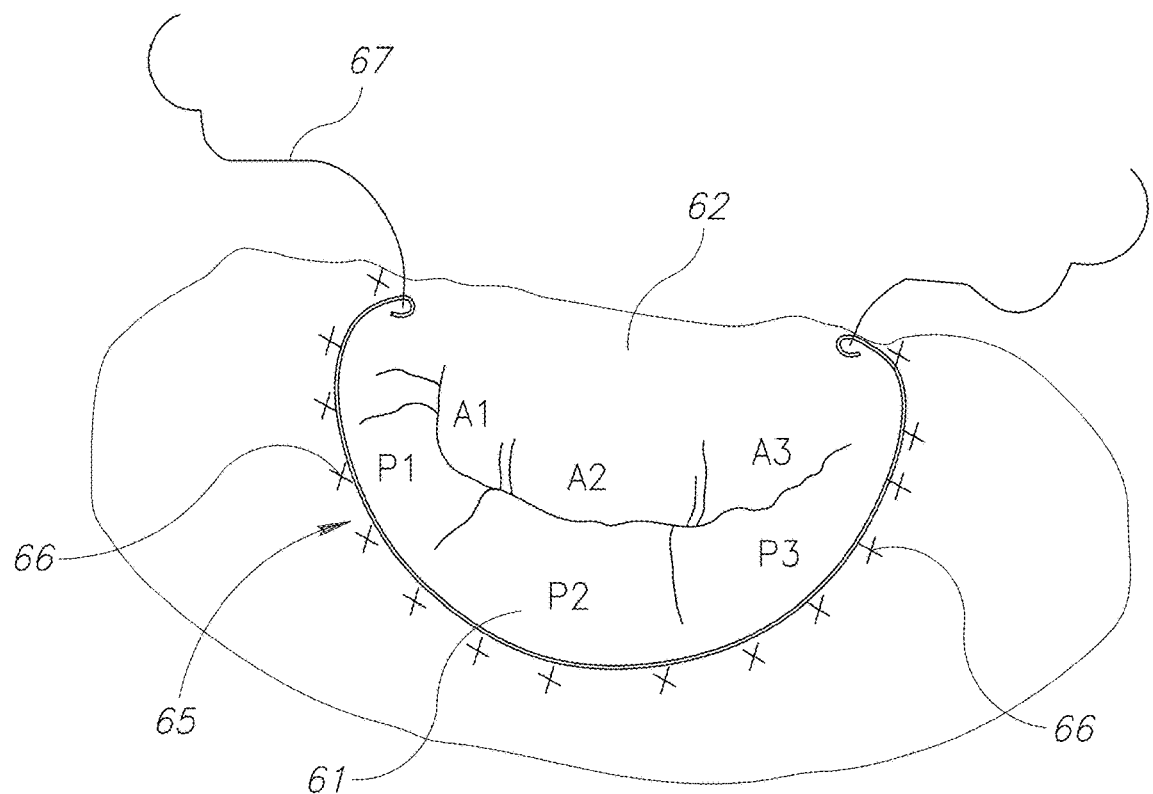

FIGS. 6A and 6B are highly schematic illustrations of the attachment of device body 110 to annulus 65, according to some embodiments of the invention. Device body 110 may be placed onto annulus 65 and secured thereto, e.g., using a surgical thread 67, providing stable support to legs 120 and bridge 130 (not shown) which protrude into LV 75. Device body 110 may be first be attached to annulus 65 (e.g., as shown in FIG. 6A) and then affixed thereto, e.g., by sutures 66. Tissue may grow over body 110 and may cover the ring-like device body 110 with time and stabilize the connection during operation of the heart. In case device body 110 is covered by biocompatible material 140, it may encourage tissue growth over device body 110, which may further stabilize the connection between body 110 and annulus 65 and reduce the risk of thrombi formation as well as reduce the risk of infection.

FIGS. 6C and 6D are highly schematic illustrations of using a single pair of artificial chords 150, attached to bridge 130, to anchor leaflet region(s), according to some embodiments of the invention. In certain embodiments, instead of prior art using of multiple pairs of artificial chords to anchor leaflet region(s), e.g., to papillary muscles 50, disclosed embodiments comprise using a single pair of artificial chords 150 to zig-zag between bridge 130 and leaflet region(s) to affix the latter to the former. Advantageously, tension may be regulated better in the disclosed embodiments and may be equalized during the operation of heart. Moreover, disclosed embodiments enable compensatory changes in the tension and length of the parts of artificial chords 150 during the adaptation of heart tissue to the formed connections, which stabilize bridge 130 and the leaflets, rather than creating tensions which are too high or chords which become too long or too short in the prior art, as result of heart tissue reforming as a consequence of the implantation. FIGS. 6C and 6D illustrate schematically in two bottom perspective views the position of bridge 130 within LV 75 with single pair of artificial chords 150 multiple attaching leaflet regions to bridge 130.

Figure 6E:
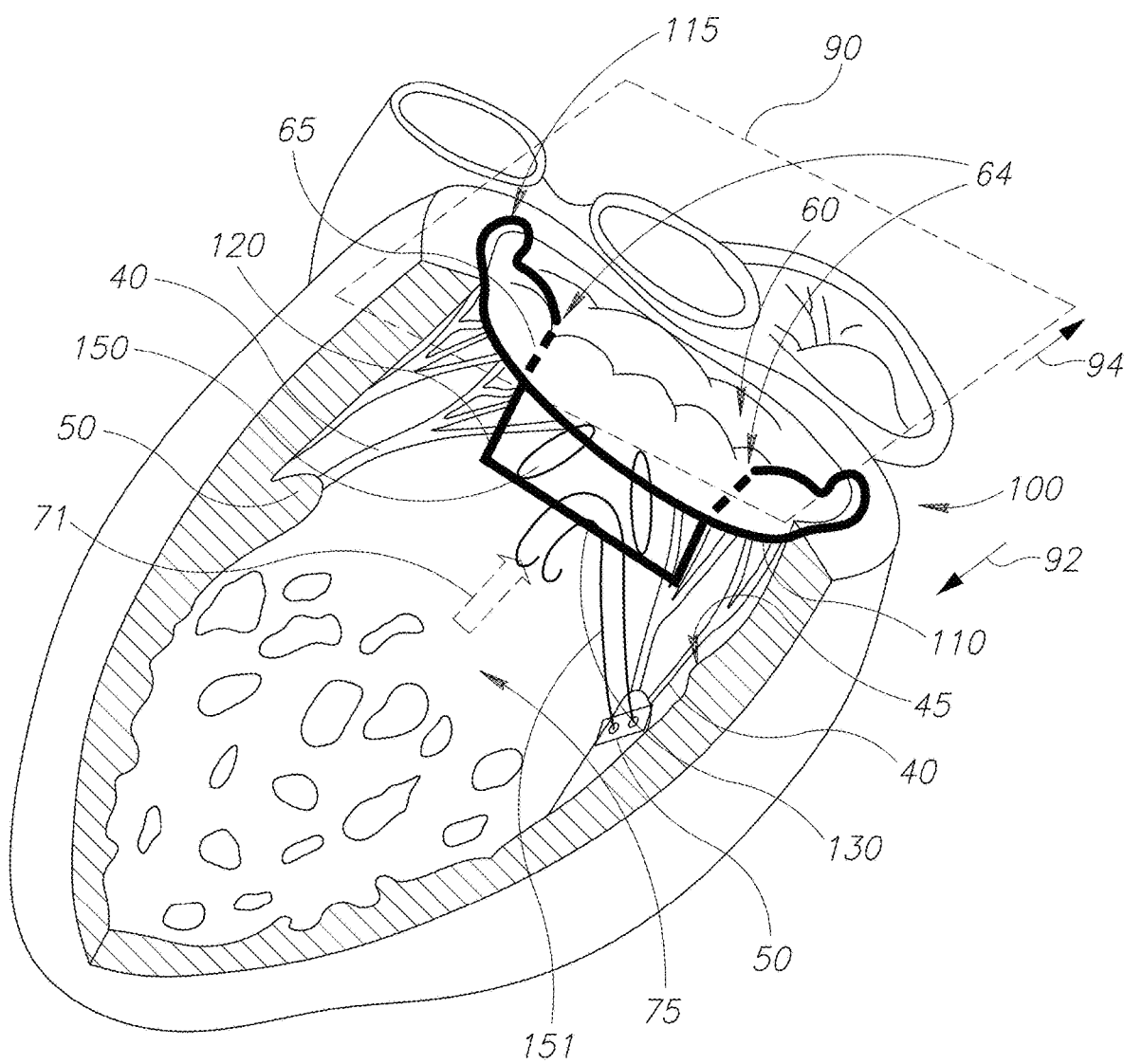
FIGS. 6E and 6F are highly schematic illustrations of using artificial chords, to attach the posterior papillary muscle and/or the posterior left ventricular wall to bridge, respectively, to anchor leaflet region(s), according to some embodiments of the invention.
Figure 6F:
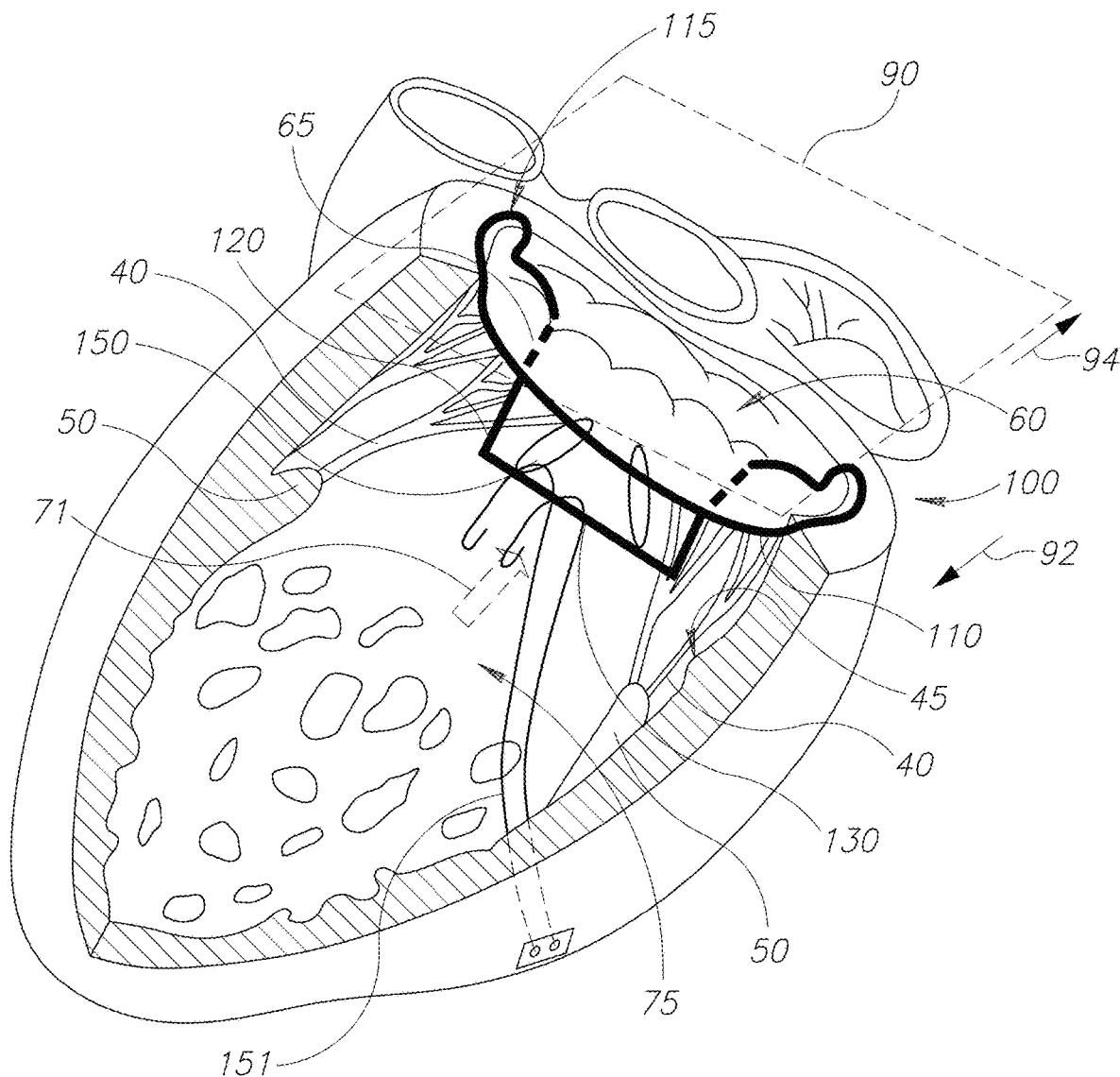

FIGS. 6E and 6F are highly schematic illustrations of using artificial chords 151, to attach the posterior papillary muscle and/or the posterior left ventricular wall to bridge 130, respectively, to anchor leaflet region(s), according to some embodiments of the invention. Either chords 150 and/or chords 151 may be used to anchor the required heart tissue to bridge (or bar) 130, e.g., using appropriate sutures, to prevent or reduce the functional mitral valve regurgitation. In certain embodiments, a single pair of sutures may be attached on one end to the bridge, and on the other end to the posterior wall (FIG. 6F) and/or to the posterior papillary muscle (FIG. 6E) to pool upwards the posterior left ventricular wall. Entry points 64 are indicated schematically in FIG. 6E, and may be modified in their position with respect to the commissures as indicated, e.g., in FIG. 1B by the non-limiting examples 64A, 64B for entry points 64.

Figure 7A:
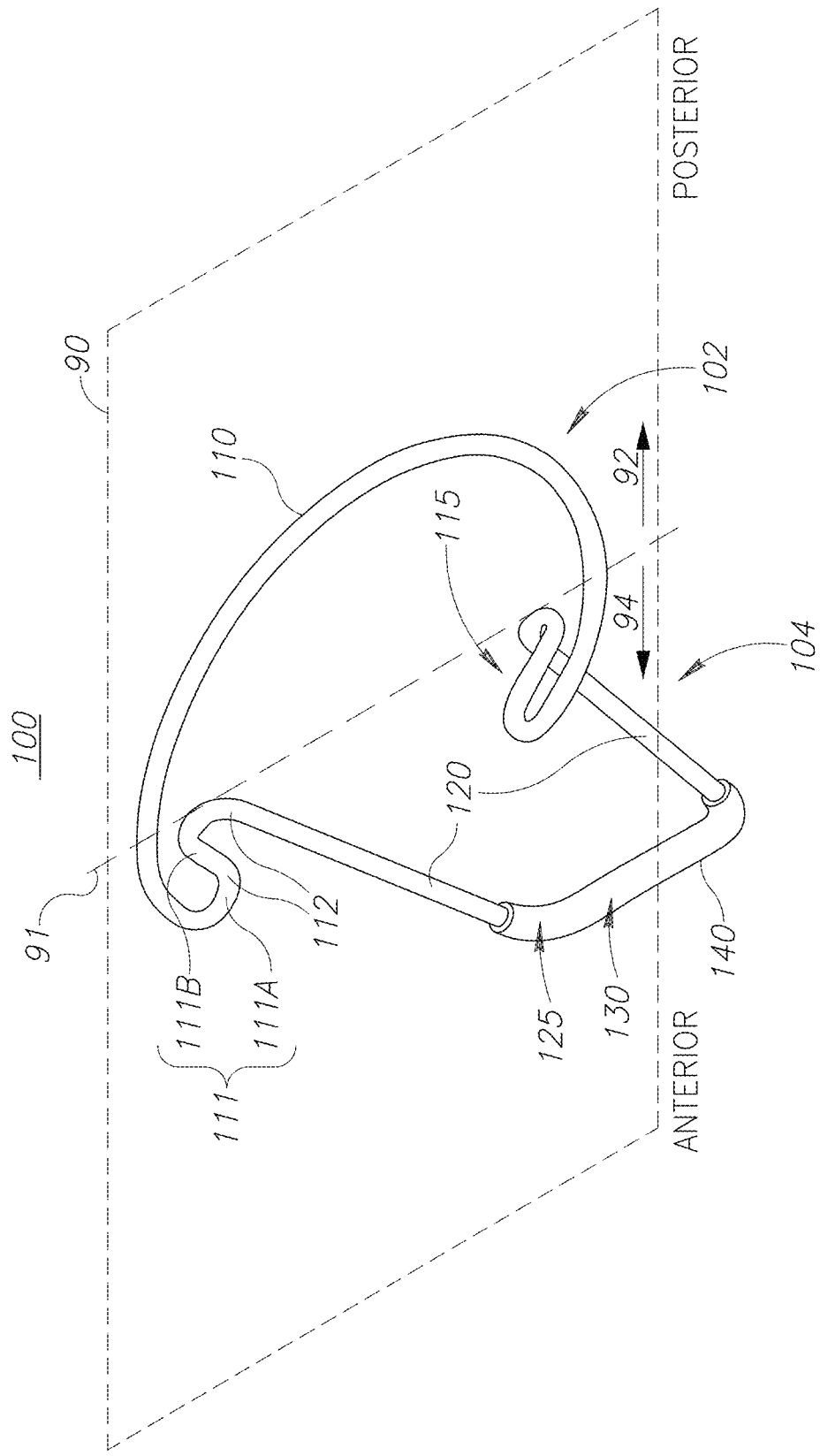
FIG. 7A is a high-level schematic illustration of a device for implantation on the mitral valve, in perspective view, according to some embodiments of the invention.

FIG. 7A is a high-level schematic illustration of a device 100 for implantation on the mitral valve, in perspective view, according to some embodiments of the invention. Device 100 includes a posterior portion 102 and an anterior portion 104 which are shown separated by dashed line 91 which separates a posterior direction 92 from an anterior direction 94 and approximately indicates the direction of the mitral valve opening. In certain embodiments, posterior portion 102 and anterior portion 104 may be co-planar, e.g., located at a plane 90 corresponding (e.g., parallel) to a plane of the mitral annulus. Posterior portion 102 and the co-planar region of anterior portion 104 may form a ring-like body 110. In certain embodiments, body may comprise bends and/or exhibit deviations from plane 90 (not shown), e.g., designed to accommodate to certain patient's anatomical features and/or functional characteristics of the patient's heart.

Posterior portion 102 may be a substantially "C-shaped" flat ring (e.g., as shown in FIG. 3N) which may be configured to be anchored to a posterior aspect of the mitral valve annulus. The radius of curvature of posterior portion 102 may be 10-20 mm (corresponding e.g., to device body diameters of 20-24 mm to 40 mm, and see indications of inner and outer diameters A and B, respectively, in FIG. 3N).

Anterior portion 104 may be contiguous with posterior portion 102 and includes a series of inward and downward bends 111 (e.g., 111A, 111B etc.) and 112, respectively, to a pair of opposing legs 120; legs 120 may be adjoined by a bridge 130 at distal ends thereof. It is noted that leg(s) 120 may be straight or bent, once or multiple times. In certain embodiments, the design of one or both leg(s) 120 may be determined with respect to specific anatomic details of the patient. Adaptation of leg form may be carried out by adding and/or removing bends in one or both leg(s) 120. Certain embodiments comprise supporting bridge 130 by additional elements, possibly by additional leg(s) 120 (not shown). It is noted that bridge 130 may be straight or bent, once or multiple times. In certain embodiments, the design of bridge 130 may be determined with respect to specific anatomic details of the patient. Adaptation of bridge form may be carried out by adding and/or removing bends and possibly bifurcation(s) or junction(s) in bridge 130. In certain embodiments, bridge 130 may be multiple (composed of more than one line) or branched, possibly including one or more loop or broadening(s) (not shown).

The radii of curvature of inward bend 111 and downward bend 112 may be selected in order to enable legs 120 to cross through the postero-medial and antero-lateral commissure regions of the valve. These curvatures may be selected along with the length of legs 120 and bridge 130 in order to position legs 120 and bridge 130 in the ventricle away from chordae, while allowing suturing of artificial chords (e.g., Gore-Tex®, polytetrafluoroethylene (ePTFE) or polypropylene] from bridge 130 to the valve leaflets. In the functional disease, the bridge 130 may be used to suspend the papillary muscle. Inward bend(s) 111 (e.g., 111A and/or 111B) may have a radius of curvature of 0.5-2 mm, while downward bend(s) 112 has a radius of curvature of 1-3 mm Inward bend(s) 111 may also have the added function of forming an open eyelet 115. Legs 120, correlated to ring size, may be 15-35 mm long while bridge 130 may have a length of 15-35 mm. When device 100 may be positioned at the mitral valve, inward bends 111 may be situated at opposite trigones (left and right fibrous trigones), enabling anchoring of eyelets 115 to these fibrous regions.

Device 100 may be fabricated from stainless steel, cobalt chromium or Nitinol wire having a diameter of 0.5-1.5 mm.

The device may be fabricated by cold forming a wire over a machined mandrel and welding and/or crimping the ends of the wire to form bridge 130. The formed device may be heat treated and electropolished. Bridge 130 may also be a polymeric or alloy tube glued over the bent end portions of legs 120.

Alternatively, device 100 may be fabricated by laser cutting a sheet or tube or by 3D printing a polymer or an alloy/metal.

The transition region between legs 120 and bridge 130 (indicated by 125 in FIG. 7A) may have a radius of curvature of 0.5-2 mm.

Legs 120 may tilt backward (towards posterior portion 102) and inward (towards device 100 symmetric centerline) at various angles controlled by inward bend(s) 111 and downward bend(s) 112 and one or more additional bend(s) 114 in each leg 120 at their connection to bridge 130 and/or along one or both leg(s) 120. Device 100 may be constructed such that the forces on ring-like body 110 during the heart cycle may be in the range of 0.02-3 N).

Figure 7B:
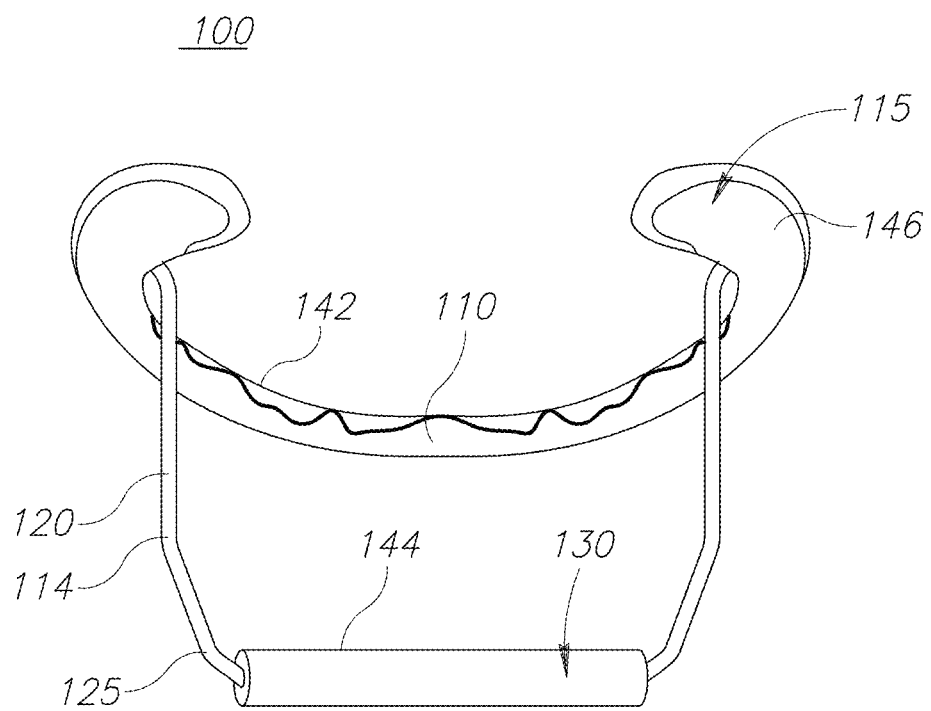
FIG. 7B is a high-level schematic illustration of a device with fabric cuffs used in in-vivo porcine experiment, according to some embodiments of the invention.

FIG. 7B is a high-level schematic illustration of device 100 with fabric cuffs 140 used in in-vitro porcine experiments, according to some embodiments of the invention. The prototype of device 100 illustrated in FIG. 5B was further used in an in-vivo pig testing. The prototype had an asymmetric backward bend in the legs, with different angles for the legs, e.g., $\alpha 2$-$\alpha 1$ of ca. 10°, and an inward bend to the legs at the annular plane and midway down the legs (similar to that shown in FIG. 7H) was constructed and tested in pigs. The prototype (shown in FIG. 7B) included fabric cuff 144 on bridge 130 and fabric cuff 142 on ring-like body 110. A 100 kg porcine was sedated and the chest cavity was opened via a midline sternotomy approach. Pre-operative ultrasound was performed to assess MR. Heparin was administered and following right atrium cannulation for vein return and ascending aorta cannulation for antegrade perfusion, a cardiopulmonary bypass was established. Ascending aorta was X-clamped to exclude the heart from the systemic blood circulation and a cardioplegia was administered to achieve heart arrest. The mitral valve was exposed via the Left Atrium and sutures were placed at the circumference of the posterior side of the annulus. The valve size was measured using a sizer and an intra-commissural approach. The appropriate device size was selected, and the sutures which were placed in the annulus passed through the outer side of the polyester cuff of the device. The device was positioned against the valve annulus and the sutures were knotted to anchor the device firmly to the native annulus. At end of surgery and after winning the extracorporeal circulation, ultrasound was performed following the implantation procedure to assess valve function. In the second phase of the procedure, two chordates were cut at P2 to induce MR. Following MR inducement, two artificial chords were attached from the bridge of the device to the leaflets.

FIGS. 7C-7F are high-level schematic illustrations of a device 100 for implantation on the mitral valve, with non-limiting examples for dimensions and angles of various device portions, according to some embodiments of the invention. FIGS. 7C and 7E are side views from two sides of device 100 (see the indications of anterior and posterior directions 94, 92, respectively), FIG. 7D is a front view and FIG. 7F is a top view (device 100 as viewed from the left atrium when in situ).

FIGS. 7C-7F illustrate schematically dimensions and configurations of device 100 which may be configured to optimize the design of device 100 and/or be adjusted to correspond to specific patient anatomy and heart dynamics. The following parameters of device geometry are shown: device width W1, bridge 130 width W3 and legs 120 intermediate width (at intermediate bends 114) W2; device posterior part length L1 and device anterior part length L2; device height H2 and legs 120 intermediate height (at intermediate bends 114) H1, posterior angles to legs 120 $\alpha 1$ and $\alpha 2$, inward angle between legs $\alpha 3$, eyelet angles $\beta 1$ and $\beta 2$ and inwards-facing leg bend angles $\gamma 1$ and $\gamma 2$ (see below); as well as the radii of curvature R1 and R2 of bends 111 and eyelet 115. Legs 120 may be bent in posterior direction 92, e.g., by 35-60°, and be bent at different angles to accommodate to asymmetries in the structures of the mitral valve and/or the left ventricle. For example, angular difference $\alpha 3$ may be between 5-15°, e.g., 10°, and all angles (and leg lengths) may be configured to accommodate bridge 130 within specified space 160.

Leg and bridge lengths and heights (W1, W2, H1, H2) as well as their angles and bending points (e.g., bend 114 and angles $\gamma 1$ and $\gamma 2$ may be interdependent, and further depended on the device dimensions, to provide appropriate positioning of device 100 and avoidance of contact between legs 120 and the mitral valve leaflets (e.g., H1 may be defined accordingly to avoid contact with the leaflets) as well as contact between legs 120 and bridge 130 and LV wall 45, papillary muscles 50 and chordae 40. For example, bend 114 may be configured to avoid contact of legs 120 with the top of the front leaflet (anterior leaflet 62).

It is noted that bridge 130 may be configured to be diagonal within specified space 160 to enable required adaptation of leaflet orientation and dynamic movements within the operating LV. For example, FIG. 7F illustrates a non-limiting example of unequal legs 120 which position bridge 130 diagonally with respect to the direction of the mitral valve opening (approximated by dashed line 91). Device 100 may be configured to be asymmetric (asymmetry indicated schematically by angle $\beta 2$), to reflect and to accommodate asymmetries in the patient's mitral valve and LV.

Non-limiting examples for dimensions comprise a bridge length of up to 30 mm, e.g., between 2-15 mm less than the device diameter (see, e.g., FIG. 3N), e.g., between 6-16 mm for device diameters of 20 mm, and up to between 25-36 mm for device diameters of 40 mm, to indicate the two extremes.

In certain embodiments, the geometry of device 100 may be configured to place bridge 130 within LV in a position that avoids contact of bridge 130 (and legs 120) with the LV wall, papillary muscles and chordae—for example leg lengths and angles may be designed and/or adjusted accordingly. For example, the length of legs 120 may range between 15-35 mm, e.g., according to the following relation between the inner diameter of device body 110 (indicated by "A" in FIG. 3N, referring to the body diameter at the entry points to the commissures) and the leg length between its entry point to the left ventricle and its connection to bridge 130 (diagonal length in case of bends in legs 120, as illustrated schematically and indicated by "C" in FIGS. 7C, 7D and 7J)—C=15+½·(A−24), in mm. In various embodiments, certain variation may be allowed in the parameters of the equation, as long bridge 130 is kept within specified space 160 and legs do not contact the leaflets, ventricle wall, papillary muscles and chordae, e.g., C=15±5+½·(A−24±10), in mm. The exact parameters may be adjusted according to device dimensions, e.g., within kits 180. Typically, the minimal length of leg 120 is 15 mm, and leg length is between 15-35 mm, which may be used to constrain the formulas presented above.

The following is a non-limiting example for device dimensions. The backward bend α1 of legs 120 shown in FIG. 7C may be e.g., between 30° and 70°, while additional backward bends of legs 120 defined by bends 111 and bend(s) 114 (e.g., at the mid-portion of each leg 120), illustrated in FIGS. 7C and 7E as 180° but possibly having different values. The inward bends γ1 and γ2 of legs 120 defined by bends 111 and bend(s) 114 (e.g., at the mid-portion of each leg 120), illustrated in FIG. 7D may be 5-20° degrees and bends 114 may be at the same distance (e.g., H1 as in FIG. 7D, e.g., 14.9 mm) from ring-like body 110 in each leg 120 or at different distances. Additional illustrated, non-limiting dimensions are W1=33.8 mm, W2=25.9 mm, W3=18.3 mm, H2=22.9 mm, L1=15.7 mm, L2=5 mm, R1=8 mm, R2=1.2 mm, β1=59° and β2=38°.

As illustrated in FIGS. 7C, 7E and 7F, certain embodiments of device 100 may be asymmetric along the posterior-anterior axis, with respect to the extent each leg 120 tilts backward (α1 and α2). For example, the difference between leg tilts α1 and α2 may be e.g., between 5-20° (in the illustrated example the difference is 10° between α1=70° and α2=80°).

FIGS. 7G-7J are high-level schematic illustrations of device 100 used in experiments, according to some embodiments of the invention. FIGS. 7G-7I are perspective views of various embodiments and FIG. 7J is a side view. These experiments were designed to further evaluate back angle α1 of legs 120 (as 70° or 80°), use of a backward bend α4 in legs 120 (at bend 114 at mid portion of legs 120) use of inward bend in legs (at mid portion). In various embodiments, devices 100 were further covered with fabric cuffs 140 as is shown in FIG. 7B above. Certain embodiments comprise additional inward bends of legs 120 (e.g., at bends 114) which may be configured to prevent contact between legs 120 and bridge 130 and papillary muscles 50 and/or chords 40.

In certain embodiments of device 100, legs 120 may be angled at one, two or more points 114 along their length (see, for example, FIGS. 7D, 7I and 8B). Such bending points 114 may provide both medial and posterior tilting (angulation) of the legs (not illustrated in FIGS. 7C and 7E, yet evident in FIGS. 7I and 8B). A first angle may tilt the legs medially (inward) at an angle less than 90° (e.g., 70-85°). A second angle of 60-85° may be introduced mid leg, e.g., about 2-10 mm from the first angle point. To avoid interference between legs 120 and the valve leaflets, posterior angulation may be achieved with one or more angle points 114. The posterior (backward) angle between legs 120 and ring-like body 100 (and annular plane 90) may be between 30° and 70° and may be derived from the leg height and length. The length of legs 120 may be related to the deepest point of ring 110 (the nadir) where the distance from that point may range between 5 mm posterior to the nadir and 7 mm anterior (see, e.g., the equations provided above). When the present device is implanted at the annulus, bridge 130 interconnecting legs 120 may be positioned between 0 and 10 mm from the deepest point of the posterior annulus. Devices 100 may be configured in ways that cause the native annulus and the differences of planes of the trigones in comparison to the posterior annulus to tilt/bend devices 100 anteriorly.

The portion of device 100 which resides in the left atrium (posterior portion 102 and anterior portion 104 co-planar with the valve annulus) may be anchored to the valve annulus using sutures staples U-anchors and the like, as in common surgical procedure. In order to facilitate such anchoring, portions of device 100 may be covered with a tubular cuff (sleeve) 140 in order to stabilize the anchoring device (e.g., by suture(s)) with respect to device 100.

Figure 7L:
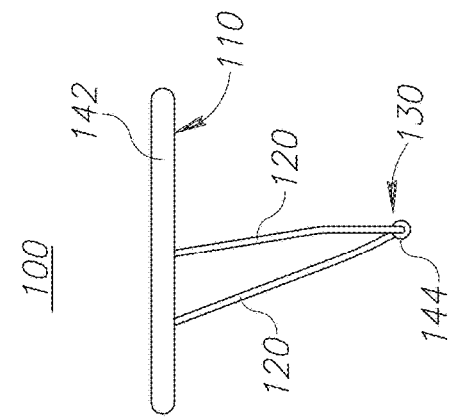
Figure 7M:
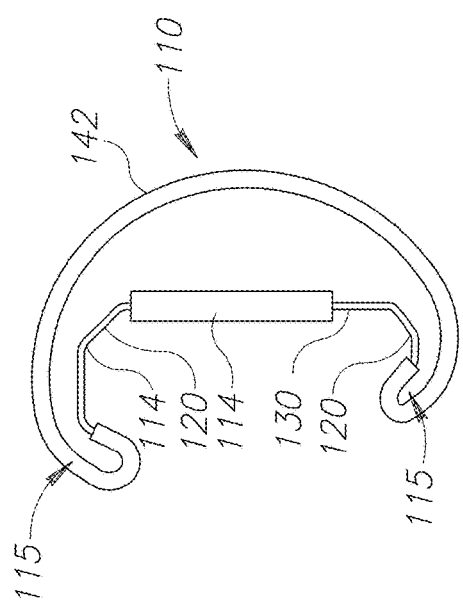
Figure 7K:
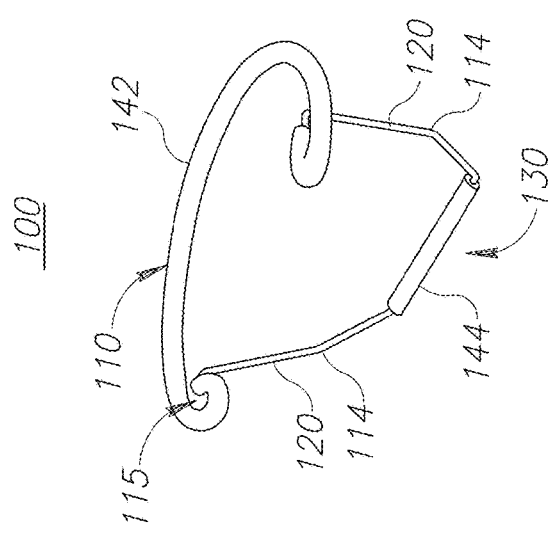
Figure 7Q:
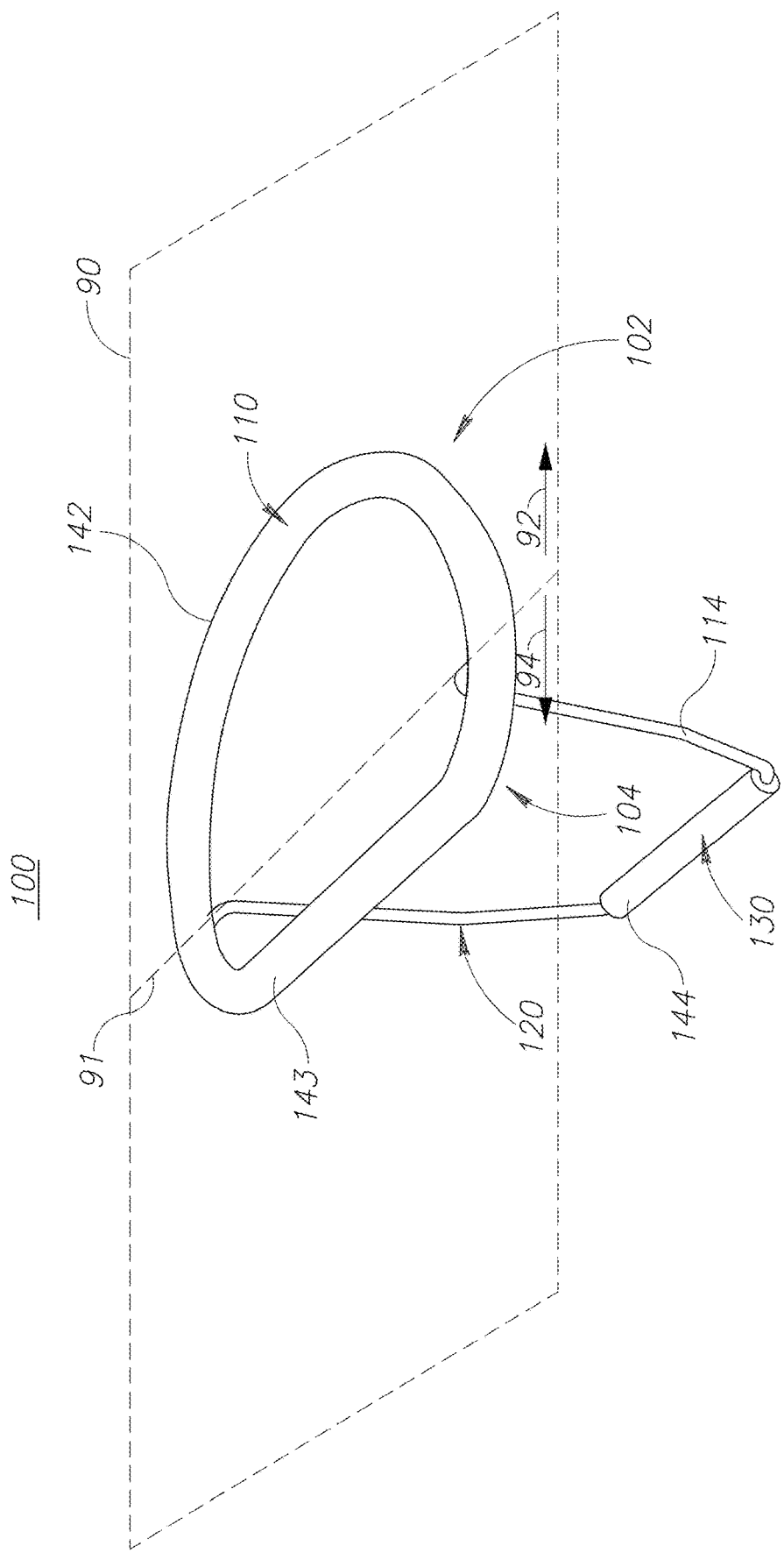

FIGS. 7K-7Q are high-level schematic illustrations of device 100 for implantation on the mitral valve, having covers 140 over at least some of its elements, according to some embodiments of the invention. FIGS. 7K, 7O and 7Q are perspective views from two different angles, FIG. 7L is a side view, FIGS. 7M and 7P are top views of different spatial relations between device body 110, eyelets 115 and bridge 130 (positioning the latter in the specified space, as disclosed below) and FIG. 7N is a front view. For example, device 100 may comprise a tubular cuff 142 covering ring-like body 110 and/or a tubular cuff 144 covering bridge 130.

Tubular cuffs 142 and 144 may be fabricated from a polymer or a fabric or a combination thereof (intermixed or at different layers). Such a polymer or fabric may be selected suitable for promoting tissue ingrowth. Examples of polymers include silicone and polyurethane which may be over-molded or coated to a final diameter of 1.2-2 mm while examples of suitable fabrics include knitted, braided or woven PET, polyethylene, terephthalate polyester with a thickness of 0.2-0.6 mm. In various embodiments, leaflet tissue 61 and/or artificial tissue 80 (see FIG. 11B) may be attached to any of the device parts, e.g., bridge 130 and/or leg(s) 120, and possibly be attached to cuffs 140. In some embodiments, cuffs 142 and 144 may be configured to enable fixating such tissue thereupon.

The legs 120 may be also be partially or fully covered with any of the above polymers or fabrics as independent parts of sleeve(s) 140 or as part of one continuous sleeve 140 covering a portion or all of device 100.

FIG. 7Q illustrates device 100 with body 110 configured as a closed ring, with roughly D-shaped ring-like body 110 having posterior and anterior portions (102 and 104 respectively). In certain embodiments, legs 120 may be attached directly to the ring-like body 110 and descend to form bridge 130 as described above. The manner in which legs 120 may be attached to ring-like body 110 may also be implemented with an open ring such as that shown in FIGS. 7K-7P and elements of FIGS. 7K-7P may be implemented in FIG. 7Q.

FIGS. 8A-8C are high-level schematic illustrations of device 100 with eyelets 115 raised above body 110 and plane 90, according to some embodiments of the invention. FIG. 8A is a side view and FIG. 8B is a frontal view from the posterior direction. Certain embodiments of device 100 may comprise raised eyelets, forming an angle of β3 (e.g., 5-15°, e.g., 10°) above plane 90 and ring-like body 110. The inventors note that, based on the literature and confirmed in the experiments, annulus 65 of mitral valve 60 does not necessarily lie within a single plane (to which plane 90 or body 110 may correspond) but rather may angle upwards at the regions of t commissures 63A, 63B. In order to make sure that ring-like body 110 and contiguous open eyelets 115 contact annulus 65 and do not distort it when sutured thereto, the open eyelet region of device 100 may be raised (angled up) from plane 90 of ring-like body 110. Angle β3 may be selected with respect to the posterior end of ring-like body 110, an in certain embodiments may be vary between 3-15° (10° shown in FIG. 8A). FIG. 8C illustrates schematically the positioning of device 100 within LV 75 in to avoid contact of legs 120 and bridge 130 with LV wall 45, by spacing specified space 160 (e.g., the VRS) from LV wall and possibly from papillary muscles 50 and/or chords 40, e.g., by at least a distance of D1 (e.g., 2, 3 or even 5 mm in some cases). It is noted that distance D1 is a dynamic parameter, which differs between the diastolic and systolic states of the heart. For example, in diastolic (relaxed) states, D1 may reach 1-3 cm, possibly in pathological states even more, while in systolic (contracted) states D1 may be less than 1 cm, e.g., between 5-10 mm (see e.g., FIG. 4D with D1 equaling ca. 7 mm in an experiment).

Implantation of device 100 may be carried out by exposing the mitral valve face from the atrial side and interrupted sutures may be placed through the posterior mitral annulus to the region of the trigones securing device body 110 to the circumference of annulus 65 and usually then securing device 100 to annulus 65 using sutures placed along its circumference (see schematic illustrations in FIGS. 6A and 6B). The leaflets and sub-valvular apparatus may be evaluated by the surgeon and ruptured chords may be resected if necessary. The location of artificial chord suturing at the leaflets is determined and marked. The annulus or the anterior leaflet is then sized (distance between trigones) using a dedicated sizer, or alternatively, anterior leaflet may be measured to fit the appropriate device. An appropriately sized device is selected and device 100 is attached to a handle. The device may be oriented with respect to the trigones using the handle such that inward bend(s) 111 may be aligned with the trigones and posterior portion 102 abuts the posterior aspect of the annulus. While maintaining device 100 in position, the surgeon may determine the required length of artificial chords by measuring the distance between the tip of the prolapsed leaflet to bridge 130 using notches on the holder (chord length may also be predetermined by means of transesophageal echocardiogram before proceeding with surgery). Prior to suturing device 100 to the annuls a selected number of artificial chords may be sutured at the desired location on bridge 130 via a double suture. The artificial chords may be then passed through holes in the holder to prevent loss of free suture ends in the left ventricle (see, e.g., FIG. 5). The anchoring sutures stitched through the annulus may be threaded through the antero-lateral portion (near eyelets 115) of cuff 142 (covering ring-like body 110) and ring-like body 110 of device 100 is secured against the valve. The holder may be detached from device 100 and the artificial chords may be retrieved via the handle. The sutures may be tightened and knotted around the ring, starting with the sutures placed at the commissures. The artificial chords may be sutured to the leaflets. Excess of the sutures may be resected after anchoring the valve. When the chordae causing leaflets tethering, such as in ischemic disease, the culprit chordae may be re-dissected and replaced by artificial chords. Alternatively, to restore leaflet coaptation the papillary muscle may be pulled and anchored to bridge 130, such that the native chordae do not tether the leaflets.

Another way of chordate implantation can be done in a continuous running fashion passing through the bridge and leaflet for part or all length of the treated free margin leaflet. The entire posterior leaflet may be sutured to bridge 130 to disable movement. Under such conditions, coaptation will be between the anterior leaflet and a "wall" formed by the posterior leaflet. Alternatively, a suture may be threaded through bridge 130 and the free margin of the diseased leaflet. Regardless of approach, once the leaflets are sutured to bridge 130 the valve is tested for competency. Valvular competency is tested by injecting saline into the left ventricle through the mitral; orifice and observing coaptation of the leaflet. If needed, the length of the artificial chords is revised by moving the knot. Once the procedure is completed, transesophageal ultrasound is performed to evaluate valve performance.

The above general approach can be varied/modified based on mitral valve pathology—degenerative or functional.

In correction of degenerative disease, prior to ring fixation to the native annulus valve, one or both leaflets may be fixed directly to the bridge, using a surgical suture. Such a procedure may be done especially when excessive leaflet tissue is noted like in Barlow disease.

Alternatively, when artificial chordae are indicated for use, the chordae may first be attached to the bridge and then anchored at the right position in the leaflet. Such a procedure is indicated when chordae are torn or elongated. The bridge may be used to anchor one or both leaflets.

When more than one pair of chordae are required, the artificial chordae may be passed in a running fashion between the bridge and free margin of the leaflet and finally fixed at the two extremities. In such a procedure less knots are required, and equal tension on the chordae and leaflet can be achieved.

In functional disease typically, the valve apparatus is intact and the valve dysfunction is related to left ventricle geometry changes which result in changes in papillary muscles position. Following ischemia or myocardial infarction or when the left ventricle is dilated, papillary and native mitral chordae pull the leaflets into the left ventricle cavity, resulting in mitral regurgitation. The tethering most frequently can be noted in the postero-medial papillary muscle affecting both anterior and posterior leaflets corresponding to the P3 and A3 leaflet regions. To repair such pathology, the fibrotic end of the culprit papillary muscle can be detached completely or partially and reattached to the bridge. Another surgical technique to eliminate tethering is to pull, via suture, the whole papillary muscle (papillary muscle suspension) and attach it to the bridge. To treat functional mitral regurgitation, the dilated/infarcted left ventricular wall can be suspended via trans-wall suture anchoring to the bridge. The entire myocardium wall is pulled toward the mitral annulus, thus eliminating the tethering of the mitral valve apparatus.

It will be appreciated that in approaches in which the muscle is directly attached to the bridge, movement of the leaflets is still enabled. Alternatively, one or more chordae can be detached, and new artificial chordae can be attached between the bridge and free leaflet margin.

Various embodiments comprise medical devices 100 that may be applied to patients affected by valvular heart diseases, e.g., by decompensation of the mitral valve causing stenosis and/or insufficiency, adapted to allow the fixing of the prolapsing valve leaflet directly or by means of artificial cords, to the prosthetic structure itself. Advantageously, disclosed devices allow simplifying and facilitating the entire operation, rendering the repair of the mitral valve entirely independent of the changes of the ventricular geometry both in the post-operative period and of the modifications due to the remodeling of the left ventricle itself. In the chronic pathology of the mitral valve, the geometry of the left ventricle is modified over time, pathologically adapting itself over time to the valvular defect. Such modifications commonly lead to hypertrophy and left ventricular dilation, but these pathological modifications are mainly reversible and partially or completely regress following the restoration of the correct valvular operation. Therefore, at the current state of the art, if artificial cords are used anchored on one side on the valve leaflet and on the other side on the papillary muscles, the length of the cords is defined based on the size and on the ventricular geometry which will very probably be modified in the post-operative period. Moreover, prior art reduction of the volume of the left ventricle could cause an excessive prolapse of the cords applied since the distance between the repaired mitral leaflet and the subvalvular apparatus decreases considerably and unpredictably after the operation. Advantageously, disclosed devices overcome such prior art critical states, allowing the fixing of the mitral leaflet, directly or by means of the cords, on the device itself; such device, given that it is substantially stable and independent, and avoids all the critical states correlated with the modification of the volume of the left ventricle in the post-operative phase. Certain embodiments of the device for the plastic surgery of the mitral valve are configured to be capable of restoring, when implanted in the dysfunctional mitral apparatus, a more physiological cardiac activity, also in the cases in which the operation is risky, e.g., in the presence of calcification phenomena involving most of the mitral annulus. Certain embodiments of the disclosed devices comprise a curved body made of a material that is solid though ductile and malleable and which is of course biocompatible with the human organism. The material must also have a sufficiently high "semi-rigidity" to allow the curved body to maintain its conformation unchanged following the stresses imparted by the heartbeats. The curved body is also to be applied on the plane where the native mitral annulus lies.

In certain embodiments, devices 100 may be distinguished from conventional devices in their high versatility, which allows being able to use the device in question in various pathological situations, exploiting its structural variants which correspond to its preferred embodiments. Medical device 100 may be configured in a versatile manner by configuring at least two descending portions present on the curved body, which may be inserted, when the surgery treatment is executed, inside the mitral orifice. Descending portions 120 (e.g., legs 120 described above) of device 100 may be shaped and sized in a manner such that, when inserted in the mitral orifice, they do not interfere with the correct ventricular activity of the heart and of the motility of the mitral cusps. Descending portions 120, e.g., legs 120, are thus to be implanted inside the mitral orifice and substantially act as an actual grip for the anchoring of broken or damaged tissues, or for the application of new biological tissues, e.g., bovine pericardium, to be extended on the dysfunctional valvular portion. Descending portions 120, e.g., legs 120, may extend into and inside the orifice, being directed parallel to the direction of the blood flow, which is assumed to be perpendicular to the plane delimited by the circular crown where the mitral annulus lies; and/or descending portions 120, e.g., legs 120, may be moved away from the direction parallel to the blood flow, upward towards the left atrium, remaining however within the mitral orifice. Devices 100 may be configured to enable to vary the conformation of the device, depending on the verifiable cases, e.g., be configuring the malleability of the material constituting disclosed devices. In certain embodiments, the curved body may comprise an annular portion having a profile similar to that of the common currently used rings for annuloplasty, from which two descending portions depart that are perpendicular to the plane where the annular portion lies, like shoe vamps. In certain embodiments, the annular portion, when applied via suture, surrounds the mitral orifice and may be configured to allow restricting the mitral orifice, e.g., in cases of insufficiency, involving all of the advantages that the conventional rings already provide. In addition, due to the presence of the at least two descending portions, the annual portion may be configured to enable repair of the dysfunctional tissue by anchoring, for example, a prolapsed cusp to the descending portions, thus restoring a more physiological cardiac activity, without having to necessarily intervene on the tendinous cords and/or on the valve apparatus. The possible breakage of the tendinous cords is indeed one of the possible causes of prolapse of the mitral leaflets.

In certain device embodiments, if the mitral leaflet is excessively retracted or damaged, it is possible to use the descending portions as grip for the implant of a new biological tissue, adapted to cover the natural mitral leaflet as an extension. For example, the extension of biological tissue, such as bovine pericardium, can be applied to the mitral apparatus by joining via suture, on one side, the tissue to the perivalvular portion, and on the other hand to the at least two descending portions, in a manner such that the tissue represents an extension of the damaged natural leaflet. The disclosed devices may be configured to be versatile, e.g., be applicable to cases in which, for example, the mitral annulus is excessively damaged, as occurs in the case of fibro-calcification, and the leaflets are excessively retracted. In the prior art, the calcified annulus indeed makes it difficult if not possible, or in any case of high risk, to implant conventional annular systems, since a soft substrate is missing on which it is possible to execute the suture of the annular device.

Certain embodiments of the disclosed devices are configured to overcome this limitation by their configuration as having the curved body comprising at least two curved independent portions, each comprising a descending portion directed perpendicular with respect to the plane where the curved portion integrated therewith lies. The curved portions, each provided with a descending portion, may be implanted on the mitral valve, at the height of the commissures, thus overcoming the need of an annular implant along the entire circular crown where the calcified native mitral annulus lies. Once the two curved portions are applied to the damaged apparatus, it is possible to apply the extension of tissue biocompatible, exploiting the possibility of "anchorage" of the tissue to the two descending portions. In certain embodiments, in order to facilitate the anchorage of a prolapsed leaflet, or of a biological tissue to be implanted, the descending portions may be inserted at the height of the commissures, and may be bound to each other. For example, the descending portions may be bound by a binding element (e.g., a bridge) represented by a section of material, and/or by joining the ends of the descending portions that are directed towards the ventricle. This material section may be oriented orthogonal with respect to the descending portions and possibly facilitate the "anchorage" of a prolapsed leaflet, or the implant of a biological tissue or another biocompatible tissue, to be fixed, by means of suture, at least in part on the disclosed device, and in part on the perivalvular tissues of the damaged mitral apparatus. The versatility of disclosed devices is further demonstrated in cases in which the curved body has a curved portion that may be applied on the plane where the mitral annulus lies. The curved portion may have the ends descending from the plane and inserted inside the mitral orifice, in a manner so as to superimpose the entire device on the damaged mitral leaflet. Advantageously, such embodiments have been proven to be particularly useful when a prolapse is verified of a mitral leaflet following a breakage of the tendinous cords. The implantation of disclosed device embodiments may allow arranging the prolapsed mitral leaflet in its native configuration, e.g., directed inside the mitral orifice and no longer towards the left atrium of the heart. This configuration may be maintained due to a direct suture of the prolapsed leaflet with the two descending portions, or due to an indirect suture by means of tendinous elements, such as artificial tendinous cords, which on one hand bind the leaflet, and on the other the descending portions of the device in question. If it is necessary to substitute the native leaflet, it is possible to model the device described in the preceding embodiment, by varying the conformation of the descending portions, by way of a non-limiting example, by profiling the descending portions as a U, with the concavity turned upward, or as an L, or by providing one descending portion as a U and the other as an L. This particular induced profile allows supplying the descending portions on which it is possible to obtain multiple suture points with a possible biological tissue, to be implanted as an extension on the device.

Certain embodiments comprise devices 100 for plastic surgery of a mitral valve, which may be implanted in subjects affected by valvular heart diseases causing stenosis and/or insufficiency, the device may comprise: at least one curved body, to be implanted coplanar with the native mitral annulus, wherein the curved body has at least two portions extended in different planes with respect to that in which the curved body lies, adapted to assist a surgeon in the operations of repair of a mitral apparatus of a patient affected by stenosis and/or insufficiency, the curved body having at least two descending portions to be inserted inside the mitral orifice, adapted to provide a grip for anchoring a prolapsed leaflet and/or of a biological tissue biocompatible with a human organism and/or of tendinous elements when the device is applied to the damaged mitral apparatus of a patient.

Certain embodiments comprise devices 100, wherein the curved body has an oval profile, the curved body being represented by an annular portion having profile similar to that of the common rings for annuloplasty currently used for restoring a functional and correct mitral valvular activity, and in that the at least two portions depart from the annular portion, being extended inside the valvular orifice when the device is implanted in the mitral apparatus of the patient, the annular portion having the descending portions directed, at the height of the commissures, like shoe vamps in a manner so as to form, with the plane in which the body lies, an angle comprised between 80° and 100°, the at least two descending portions departing from the center of the minor arcs of the oval profile.

Certain embodiments comprise devices 100, wherein the curved body is represented by at least two curved portions to be arranged coplanar with the native annulus at the height of the commissures, the device comprising at least one curved portion to be arranged at the height of one valvular commissure and at least another curved portion to be arranged at the height of the commissure opposite to the first, and in that each curved portion has at least one descending portion to be inserted inside the valvular orifice, and extended in a manner so as to form an angle comprised between 80° and 100° with respect to the plane in which the curved portion lies, the portion departing from the center of such curved portion.

Certain embodiments comprise devices 100, wherein the ends of the descending portions, turned towards the valvular orifice, are shaped as an L or they are shaped as two converging Ls, the ends defining, in the latter case, a section of material joining the descending portions and inserted inside the orifice, the device having the section extended inside the valvular orifice.

Certain embodiments comprise devices 100, wherein the curved body is represented by a body defining an open curve to be implanted in part coplanar with the native mitral annulus and in part inside the valvular orifice, the curved body being represented by the curved portion, to be extended coplanar with the native annulus, and having the ends descending inside the orifice when the device is implanted, the ends of the curved portion representing the descending portions.

Certain embodiments comprise devices 100, wherein the curved body is represented by a body defining an open curve to be implanted in part coplanar with the native mitral annulus and in part inside the valvular orifice, the curved body being represented by the curved portion, to be extended coplanar with the native annulus, and having the ends descending inside the orifice when the device is implanted, the ends of the curved portion representing the descending portions of the device and in that the descending portions are substantially U-shaped with the concavity turned upward, or they are shaped as an L, or they are shaped with one U-shaped and the other L-shaped.

Certain embodiments comprise devices 100, wherein the portions descending towards the left ventricle have an overturned "L" shaped progression, being connected on the upper part to the annular portion or to the curved body, being centrally extended by two to eight millimeters, preferably four millimeters, towards the valvular lumen inside the mitral orifice, hence giving rise to the descending portion with respect to the plane identified by the annular portion or by the curved body, the descending portion having an angle comprised between 80° and 100°, preferably an angle of about 90°.

Certain embodiments comprise devices 100, which may comprise non-biological tissue biocompatible with the human organism, adapted to be assembled, by means of suture, to the descending portions of the device.

Certain embodiments comprise devices 100, wherein the tissue is made of bovine pericardium or of any other tissue, available on the market, that is biocompatible with the human organism.

Certain embodiments comprise devices 100, which are made of a material biocompatible with the human organism. Certain embodiments comprise devices 100, which are made of a solid material that is sufficiently malleable so as to be manually modeled by the surgeon as required, and sufficiently rigid to maintain the conformation thereof unchanged following the stresses imparted by the heartbeat. Certain embodiments comprise devices 100, which are made of a material having a thickness comprised between 0.1 cm and 0.5 cm, with regard to the portion representing the curved body, and a thickness comprised between 0.05 cm and 0.5 cm with regard to the portions representing the descending portions. Certain embodiments comprise devices 100, which are made of a material having a thickness of 2 mm with regard to the portion representing the curved body, and a thickness of 1 mm with regard to the portions representing the descending portions.

In certain embodiments, devices 100 have the descending portions of a length between 0.5 and 3.5 centimeters, e.g., between 1 and 2 centimeters.

Certain embodiments comprise methods of using plastic surgery of the mitral valve to be implanted in subjects affected by valvular heart diseases causing stenosis and/or insufficiency, the methods may comprise the following steps: implanting a mitral apparatus in a patient affected by stenosis and/or insufficiency, the apparatus having at least one curved body coplanar with the native mitral annulus, and having at least two portions extended in different planes with respect to that in which the curved body lies, and inserting the at least two descending portions inside the mitral orifice, adapted to provide a grip for the anchoring of a prolapsed leaflet and/or of a biological tissue biocompatible with the human organism and/or of tendinous elements when the device is applied to the damaged mitral apparatus of a patient.

FIGS. 9A-9H are high-level schematic illustrations of devices 100, according to some embodiments of the invention. Various aspects of devices 100 illustrated in FIGS. 9A-9H may be combined to form other device embodiments and may be combined with aspects of devices 100 disclosed above, e.g., in FIGS. 1-8 presented above.

FIG. 9A illustrates schematically embodiments of devices 100 for plastic surgery of the mitral valve having upper curved body 110 from which two descending portions 120 depart (e.g., occupying a partially central portion of the valvular lumen) and arranged perpendicular to plane 90 in which curved portion 110 lies. Curved body 110 may comprise an annular portion similar to the common annular devices currently used for the annuloplasty of the mitral valve. Annular portion 110 may have an oval profile, and may have, at the center of the two minor arcs defined by the oval profile, at least one descending portion 120, for each minor arc, to be inserted inside the mitral orifice at the height of the commissures. Annular portion 110 may be implanted, analogous to the conventional annular systems, on the mitral annulus of the damaged valve apparatus. In certain embodiments, bends 111 and/or 112 and/or loops/eyelets 115 may be introduced at the connection region between annular portion 110 and one or more descending portion(s) 120, as illustrated e.g., in FIGS. 9E-9H presented below. Descending portion(s) 120 may have an overturned "L" shape, initially arranged parallel and then perpendicular to plane 90 in which curved body 110 lies.

FIG. 9B illustrates schematically embodiments of devices 100 in which curved portion 110 comprises at least two independent curved portions 110A to be arranged, in proximity to the commissures, on the native mitral annulus. Each curved portion 110A may have descending portion 120, to be inserted into the valvular orifice when device 100 is implanted in the mitral apparatus of the patient affected by valvular heart disease. Descending portions 120 may be extended orthogonally or at an angle (see e.g., devices described above) to plane 90 holding curved portions 110A. In certain embodiments, on or more curved portions 110A may deviate from plane 90, corresponding to specific morphological features of the mitral valve in certain patients and/or enabling some relative movement of parts 110A with associated legs 120. FIGS. 9C and 9D illustrate schematically embodiments of devices 100 in which the profile of descending portions 120 (e.g., legs 120) varies, e.g., "L"-shaped in FIG. 9C and converging "L"-shaped, defining a section of material orthogonal to descending portions 120, indicated herein as section 130 (e.g., bridge 130), in FIG. 9D. The latter may be useful, for example, for providing a support on which biological tissue 80 may be sutured, such biological tissue 80 to be implanted in the damaged mitral apparatus of a patient, or for restoring, by means of suture, the correct spatial configuration and conformation of a leaflet, possibly prolapsed following the breakage of the tendinous cords.

In certain embodiments, biological tissue 80 may comprise an artificial leaflet, e.g., for treating ischemic and/or rheumatic mitral leaf regurgitation, e.g., as extension of existing leaflets or regions thereof, and/or as replacement for existing leaflets or regions thereof. Biological tissue 80 as artificial leaflet 80 may be made of, e.g., ePDFE or bovine pericardium tissue and may be used to partly or fully replace leaflet regions.

In certain embodiments, artificial chords 150, possibly in cooperation with artificial leaflet 80, may be configured to move papillary muscles 50 within LV, either backwards or forwards, to reach a more regular operation of the heart.

FIGS. 9E-9H illustrate schematically embodiments of devices 100 in which descending portions 120 first project towards the center of the lumen, then extend to the interior thereof with an angle of about 90°, giving rise to a substantially overturned L-shaped structure with bend(s) 112 and/or loops 115 interconnecting body 110 (and/or body parts 110A) and legs 120, with descending portions 120 possibly converging (as in FIG. 9F), until section 130 of the device material is defined orthogonally or at an angle with respect to descending portions 120. While FIGS. 9E and 9F illustrate schematically embodiments with separate body parts 110A, FIGS. 9G and 9H illustrate schematically embodiments with single body part 110, which may be formed as a ring, a loop, be "C"-shaped or generally any form of curve, possibly within plane 90. FIGS. 9G and 9H illustrate schematically embodiments of devices 100 in which curved body 110 has a semi-elliptical form and from this at least two descending portions 120 with overturned "L" shape depart, coinciding with the commissures. Descending portions 120 may tend in the lower part thereof to move closer together without however being connected (FIG. 9G) or descending portions 120 may be connected on the lower part by section 130 (FIG. 9H). Section 130 may be configured, for example, to provide greater support, on which a biological tissue 80 can be sutured which is to be implanted on the damaged mitral apparatus of a patient; or section 130 is useful for restoring, by means of suture, the correct spatial conformation and configuration of a leaflet, possibly prolapsed following the breakage of the tendinous cords.

Figure 10A:
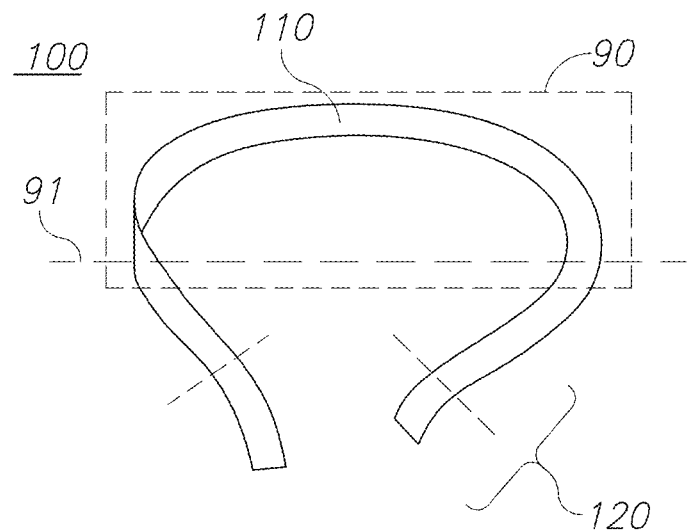
FIGS. 10A and 10B illustrate schematically embodiments of devices comprising a curved body having a curved portion which extends in part on the native annulus, and in part extends inside the valvular orifice to form descending portions, according to some embodiments of the invention.
Figure 10B:
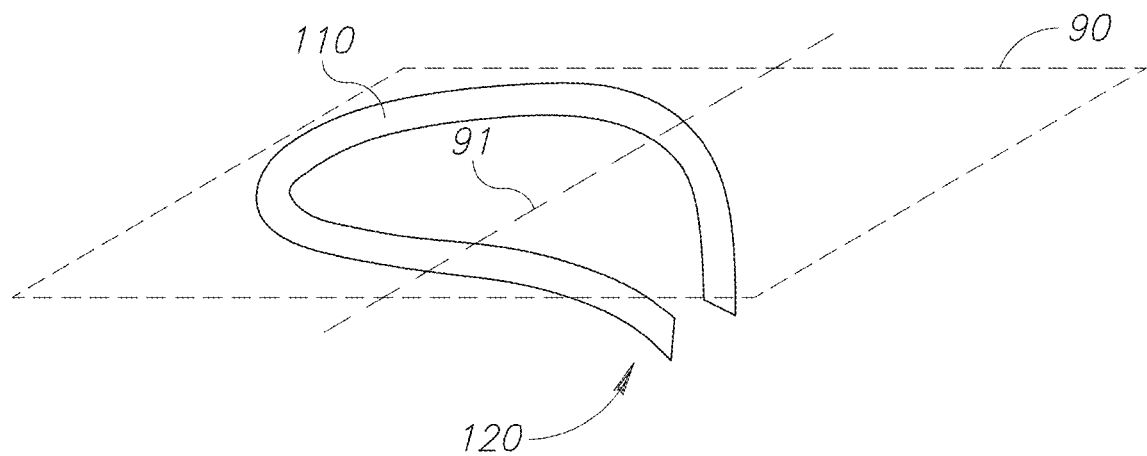

FIGS. 10A and 10B illustrate schematically embodiments of devices comprising a curved body having curved portion 110 which extends in part on the native annulus, and in part extends inside the valvular orifice to form descending portions 120, according to some embodiments of the invention. FIG. 10A provides a frontal perspective view and FIG. 10B provides a lateral perspective view. Curved portion 110 may be implanted on the mitral annulus with its ends, descending portions 120, extended into the ventricular lumen, moving away from and below plane 90 (which may be coplanar with the native annulus) into the mitral orifice. Descending portions 120 may be to some extent plastically deformable, and certain embodiments of device 100 may be configured to enable the heart surgeon to vary the configuration and the conformation of descending portions 120, profiling them in accordance with the verifiable needs. Descending portions 120 may have a variable angle with respect to plane 90 coplanar with the portion 110, and the material constituting device 100 may be solid material that is sufficiently malleable to allow shaping device 100, in accordance with the needs verifiable in patients affected by valvular heart diseases.

Figure 11A:
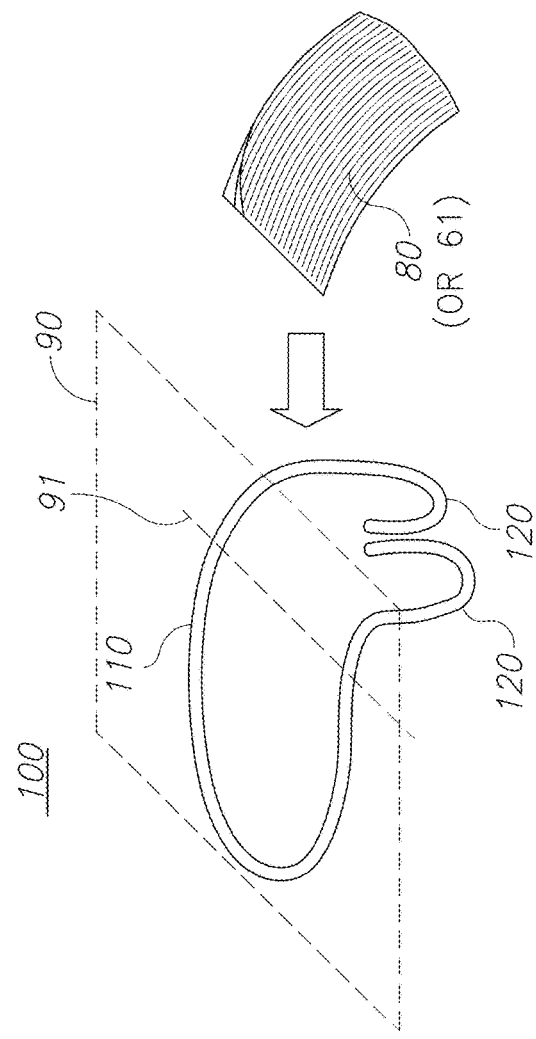
FIGS. 11A-11D illustrate schematically embodiments of devices comprising a curved body having curved portion which extends in part on the native annulus, and in part extends inside the valvular orifice to form "U"-shaped and/or "L"-shaped descending portions, e.g., to provide leaflet-like biocompatible material anchoring, according to some embodiments of the invention.
Figure 11B:
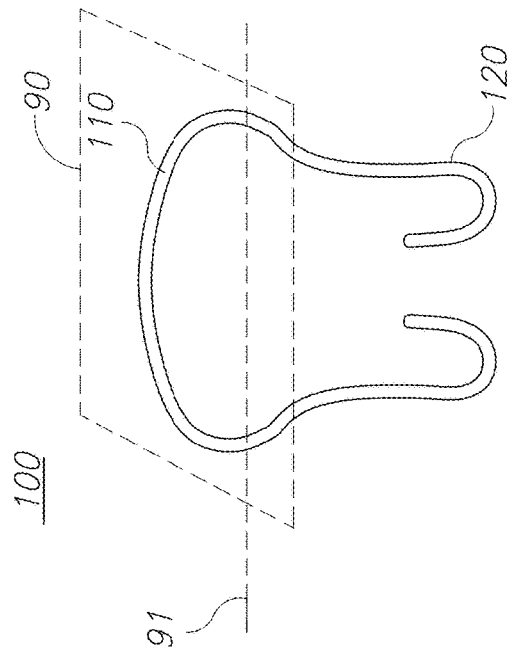
Figure 11C:
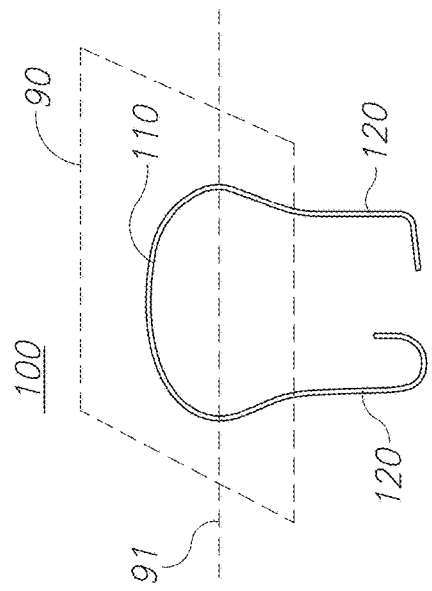
Figure 11D:
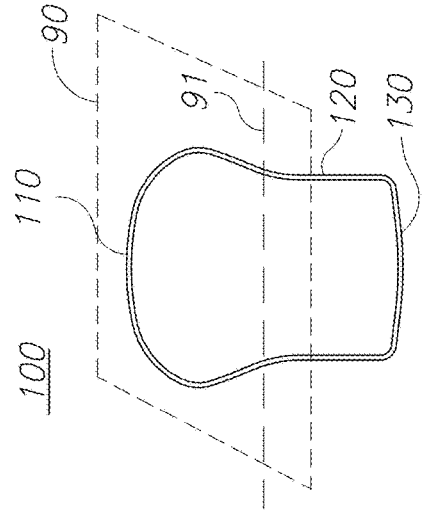

FIGS. 11A-E illustrate schematically embodiments of devices comprising a curved body having curved portion 110 which extends in part on the native annulus, and in part extends inside the valvular orifice to form "U"-shaped and/or "L"-shaped descending portions 120, e.g., to provide leaflet-like biocompatible material anchoring, according to some embodiments of the invention. FIGS. 11A, 11C and 11D provide frontal views, FIG. 11B provides a lateral perspective view with schematically illustrated biological tissue 80 that is attachable to device 100 by means of a suture line to legs 120 and/or to bridge 130 illustrated schematically in FIG. 11C, as explained above. The other end of the sutured chord(s) may be sutured directly to any level of the native posterior leaflet and/or to the native annulus. Descending portions 120 may be U-shaped with the concavity turned upward, or L-shaped with the ends converging, or L-shaped with the ends spaced, or due to the fact that different descending portions 120 may are profiled with different shapes, such as one U-shaped and the other L-shaped as illustrated schematically, in a non-limiting manner, in FIG. 11D. Specified profiles of the ends of descending portions 120 (legs 120) may be configured to facilitate the implant of biological tissue 80 (e.g., using one or more sutures) to device 100, onto a substrate that maintains the conformation and spatial extension of tissue 80 stable over time, in a manner such that tissue 80 represents an extension of the dysfunctional mitral leaflet, when device 100 is applied to the mitral apparatus of the patient. Legs 120 may be shaped to provide such support, possibly customizable with respect to specified patients. In certain embodiments, legs 120 may be connected by bridge 130, which may also support tissue 80.

Figure 11E:
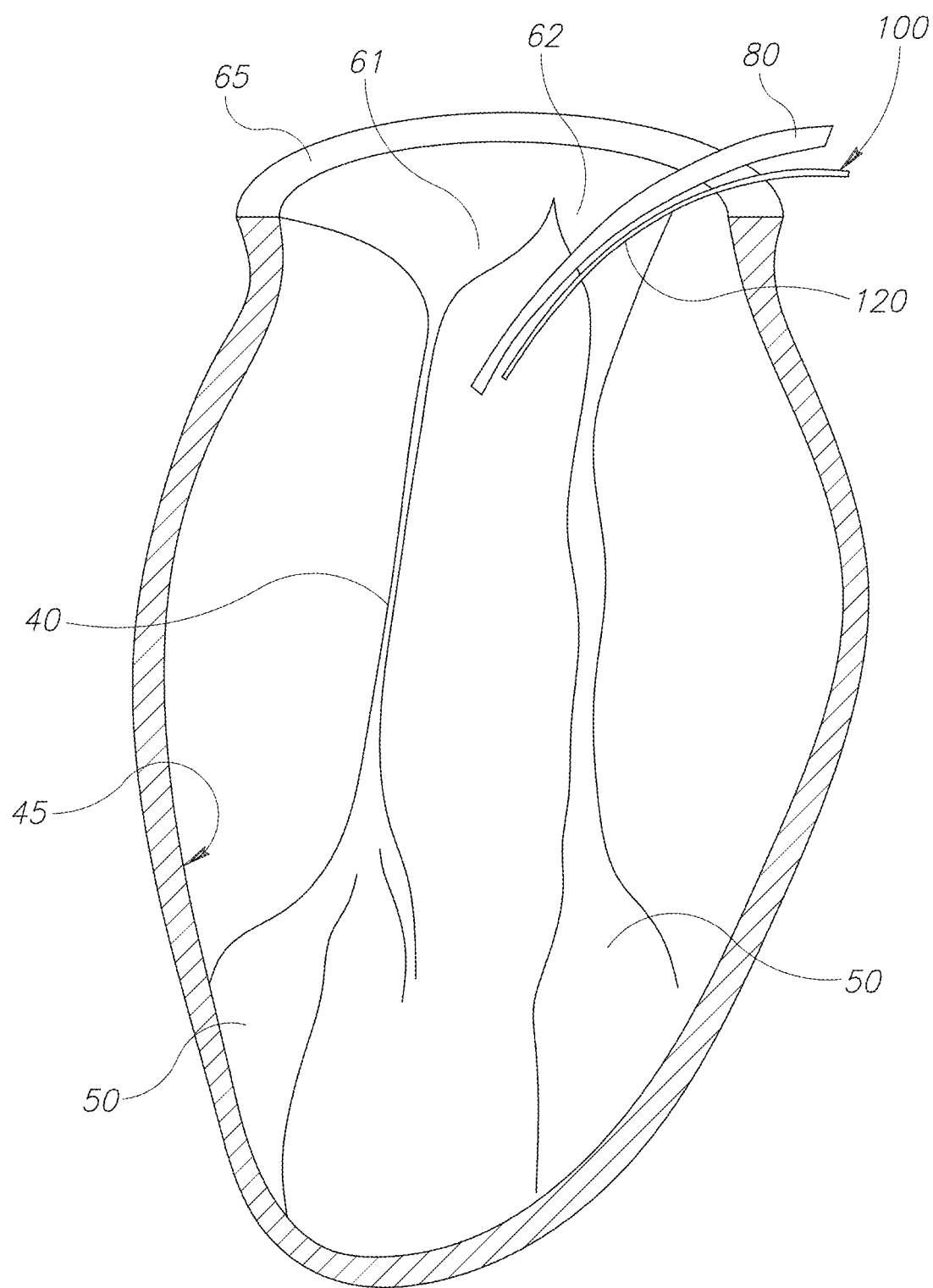
FIG. 11E illustrates schematically implantation procedures of devices on a longitudinal section of the left ventricle of a human heart, according to some embodiments of the invention.

FIG. 11E illustrates schematically implantation procedures of devices 100 on a longitudinal section of the left ventricle of a human heart, according to some embodiments of the invention. The correct closure of the mitral valve in the systolic phase be restored by the application of an extension represented by biological tissue 80 supported by leg(s) 120 of device 100, which comprises curved portion 110 as curved body 110 to be arranged coplanar with the native annulus, and descending portions 120 which may be U-shaped, and/or L-shaped, or one L-shaped and the other U-shaped, and adapted to fix tissue 80 to device 100 via suture, in a manner such that tissue 80 represents an extension of the damaged native leaflet causing insufficiency.

In certain embodiments, device 100 may comprise at least one curved body 110 to be implanted, during the execution of the heart surgery treatment, e.g., on plane 90 where the native mitral annulus lies (conventionally, but not limitingly, assumed to be orthogonal with respect to the direction of the blood flow), and at least two descending portions 120 which are inserted, during the surgical treatment, inside the orifice of the damaged mitral apparatus. Descending portions 120 may be configured to move away from plane 90 in which curved body 110 lies, to which descending portions 120 are joined, in a manner so as be directed inside the mitral orifice.

In certain embodiments, curved body 110 of device 100 for plastic surgery of the mitral valve may comprise an annular portion 110 having a profile similar to that of the common rings for annuloplasty currently used for facilitating the restoration of a functional and correct valve activity. Device 100 may be characterized by the presence of at least two descending portions 120, like shoe vamps, which depart from annular portion 110, generally having oval profile, in proximity to the center of the minor arcs of the oval form; in such a manner, when the device is implanted in the mitral apparatus of the patient affected by valvular heart disease, descending portions 120 may be inserted in the mitral orifice at the height of the commissures, and may be shaped and sized in a manner such that they do not interfere on the physiological ventricular activity of the human heart and of the normal function of the mitral leaflets. Device 100 may be configured to allow using descending portions 120 as an actual grip, e.g., as a grip for a possibly prolapsed leaflet, or for anchoring a biological tissue, such as bovine pericardium, to be extended on the dysfunctional valve portion, with all the advantages obtainable with the already-known annular devices, and substantially involving the approaching of the mitral leaflets.

In certain embodiments, device 100 may comprise curved body 110 configured to be coplanar with the native annulus and at least two independent curved portions 110A configured to be implanted on the native annulus at the height of the commissures. Some or each of curved portions 110A further comprises at least one descending portion 120 configured to be inserted inside the orifice departs, orthogonal or possibly at a specified angle with respect to each curved portion 110A. Advantageously, independent curved portions 110A may be useful when it is not possible to execute the stable implant of curved body 110, e.g., of annular portion 110, on the native annulus. This condition is widely diffused and usually corresponds to the case in which the mitral annulus is widely calcified, to the point where it is difficult and risky to apply the conventional rings, by means of suture, to the perivalvular tissues. In some cases, the calcification encountered is so formidable as to make any operation impossible, thus, in the prior art, giving up the possibility to restore a correct cardiac activity, and leaving the pathology untreated. For such purpose, devices 100 may allow operation on the damaged mitral apparatus even when the implant of the conventional devices is made impossible, thus restoring a decidedly functional valvular activity. Moreover, two descending portions 120 may be configured to act as a support system and as a source of grip for a possibly prolapsed leaflet, or for the fixing of a biological tissue adapted to simulate the activity of the dysfunctional native leaflet, or for another application.

In certain embodiments, in order to assist the surgeon in the operation of implanting a biological tissue biocompatible with the human organism, device 100 may comprise at least two descending portions 120, having the ends L-shaped. L-shaped portions 120 may converge to a specified extent until material section 130 is defined, adapted to represent a stable support on which the biocompatible tissue 80 can be sutured. Section 130 may extend inside the mitral orifice, orthogonal or at an angle to descending portions 120, without interfering on the physiological ventricular activity. Device 100 may comprise curved portion 110 extending and being implanted coplanar with the native annulus, and descending portions 120 at the ends of curved portion 110. The ends, e.g., descending portions 120, may be configured to move away from plane 90 of the native annulus, being extended inside the mitral orifice. Descending portions 120 may be configured to have specified angles with respect to plane 90 and specified distances from anatomical structures in the left ventricle to ensure unhindered operation of the heart. The angle of descending portions 120, with respect to the plane of the mitral annulus (e.g., possibly but not necessarily plane 90 of body 110), can be manually varied by providing appropriate material properties of device 100 and possibly physician manipulation before or during implantation. As mentioned above, the device material may be selected as being sufficiently malleable to be variously shaped under the action of a mechanical stress impressed manually, and at the same time sufficiently rigid to resist the mechanical stressed impressed by the heartbeat cycle.

In certain embodiments, device 100 may be configured, when used for plastic surgery of the mitral valve, to restore the operation of a prolapsed valve leaflet. This outcome can be obtained by assembling the prolapsed leaflet to the lower portion of device 100, which comes to be implanted on the leaflet. The assembly can occur in a direct manner, e.g., via suture(s) of the leaflet onto descending portions 120 of curved portion 110, or via indirect suture, e.g., by means of tendinous elements, such as artificial tendinous cords 150, which may be used indirectly to bind device 100, e.g., its descending portions 120, to the respective valve cusp.

In certain embodiments, curved body 110 of device 100 may be configured to have specified conformation and profile of its ends, e.g., of descending portions 120. Descending portions 120 may be U-shaped with the concavity turned upward, or L-shaped and/or a combination thereof. The conformation and profile of curved body 110 and/or descending portions 120 may be selected to enable and/or simplify the implantation of biological tissue 80 that is biocompatible with the human organism and adapted to simulate the activity of a dysfunctional cusp, which, for example due to an excessive retraction, is unable to ensure a correct superimposition of the leaflets during the systolic phase of the ventricle. By way of a non-limiting example, U-shaped descending portions 120 may be configured to facilitate the stable assembly, via suture, of biological tissue 80 to legs 120 (e.g., to the ends thereof), to have biological tissue 80 implanted like an extension of the damaged native leaflet, once device 100 has been implanted in the dysfunctional mitral apparatus of the patient.

In certain embodiments, device 100 may be configured to have a material thickness between 0.1 cm and 0.5 cm, e.g., 2 mm, with regard to curved body 110, and a thickness between 0.05 cm and 0.5 cm with regard to descending portions 120, e.g., descending portions 120 may have a thickness of 1 mm. In certain embodiments, descending portions 120 may have a length, intended as a depth extension inside the mitral valve, which is between 0.5 and 3.5 centimeters, e.g., between 1 and 2 centimeters.

In certain embodiments, device 100 may be configured to have descending portions 120 connected to curved body 110 or to annular portion 110, in a manner that initially extends for about two to eight millimeters (e.g., three millimeters), towards the center of the annulus itself, before then completing a specified angle (e.g., about 90°) to descend into the left ventricle, towards the floor of the left ventricle. In certain embodiments, descending portions 120 may be maintained separated from the heart wall, occupying the most central portion of the valvular lumen. The absence or the reduced presence of contact between descending portions 120 and the heart walls may be configured to ensure the reduction of undesired friction and rubbing, often a cause of future problems that can cause undesired side effects. The overturned "L" shaped progression of descending portions 120 may be configured to eliminate the possibility that the critical states can be established, and possibly to eliminate the possibility of the onset of side effects due to the physical contact between the descending portions and the heart commissures. Two descending portions 120 therefore may have a substantially overturned "L"-shaped structure, having an initial portion connected to annular portion 110 or to curved body 110, substantially placed on the same plane as annular portion 110 or curved body 110, and descending portion 120 may be adapted to be inserted inside the mitral orifice at the height of the commissure. Descending portion 120 may have, with respect to plane 90 defined by annular portion 110 or by curved body 110, a specified angle, e.g., between 80° and 100° (e.g., about 90°). In certain embodiments, curved body 110 may have a semi-elliptical form with an open portion. In certain embodiments, body 110 may be substantially arranged on a plane from which, at the commissure, at least two descending portions 120 departing having overturned "L" shape. Descending portions 120 may be free or connected together to form section 130 (e.g., bridge 130), arranged on a plane parallel with respect to the plane on which body 110 lies.

Figure 12:
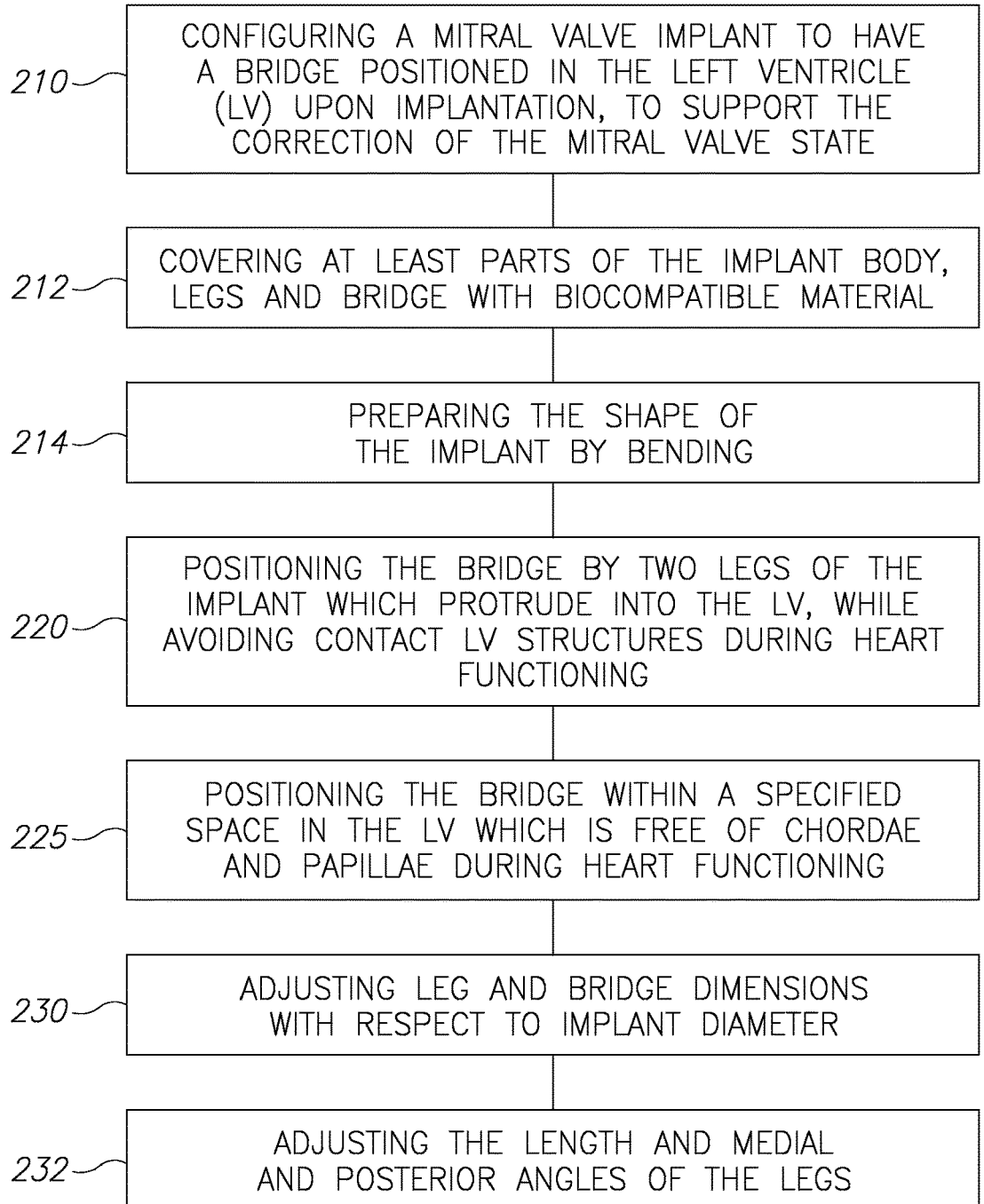
FIG. 12 is a high-level flowchart illustrating methods, according to some embodiments of the invention.

FIG. 12 is a high-level flowchart illustrating a method 200, according to some embodiments of the invention. The method stages may be carried out with respect to devices 100 described above as the corresponding implants, which may optionally be configured to implement method 200. Method 200 may comprise the following stages, irrespective of their order.

Method 200 comprises configuring a mitral valve implant to have a bridge positioned in the left ventricle (LV) upon implantation, to support the correction of the mitral valve state (stage 210). Method 200 may comprise covering at least parts of the implant body, legs and bridge with biocompatible material (stage 212) and possibly preparing the shape of the implant by bending (stage 214). Method 200 may comprise positioning the bridge by two legs of the implant which protrude into the LV, while avoiding contact LV structures during heart functioning (stage 220), e.g., positioning the bridge within a specified space in the LV which is free of chordae and papillae during heart functioning (stage 225). Method 200 may further comprise adjusting leg and bridge dimensions with respect to implant diameter (stage 230), e.g., to provide a kit with multiple implants having different sizes and corresponding bridge positions. Method 200 may further comprise and adjusting the length and medial and posterior angles of the legs (stage 232).

In certain embodiments, method 200 may comprise configuring the implant to have eyelets that define the entry points of the legs into the LV (stage 240) and possibly adjusting the position of the entry points of the legs into the LV with respect to the anterolateral and the posteromedial commissures, according to the mitral valve condition (stage 242). In certain embodiments, method 200 may comprise raising the eyelets above the plane of the device body to accommodate for specified annulus conditions (stage 244).

Method 200 may comprise providing a set of implants in different sizes, with the adjusted leg and bridge dimensions (stage 250).

In certain embodiments, method 200 may comprise attaching at least one pair of artificial chords to the bridge, to be connected upon implantation to the valve leaflets and/or to the papillary muscle(s) (stage 260). Method 200 may comprise configuring the implant to enable connection of tissue thereto (stage 270).

In some embodiments, method 200 may comprise offsetting the entry points of the legs with respect to the anterolateral and the posteromedial commissures in case of ischemic mitral regurgitation (stage 280).

Method 200 may further comprise attaching tissue to the implant, to augment at least one of the valve leaflets (stage 290) and/or attaching a valve leaflet to the implant (stage 295).

In certain embodiments, method 200 may comprise implanting the implant body onto the annulus and connecting leaflet tissue to the bridge by the at least one pair of artificial chords (stage 300). Method 200 may comprise treating the Barlow syndrome by implanting the implant body onto the annulus and fixating leaflet tissue to the bridge (stage 310) and/or treating ischemic mitral regurgitation by the offsetting of the legs and corresponding adjustments of the implant geometry (stage 320).

In some embodiments, method 200 may comprise using a single pair of artificial cords and connecting tissue to the bridge by zig-zagging the artificial chords between the bridge and the leaflet tissue, to equalize tension along the cords (stage 330).

Method 200 may further comprise positioning the implant onto the annulus using a holder configured to release the implant while supporting the cords (stage 340).

It is emphasized that elements from different embodiments may be combined in any operable combination, and the illustration of certain elements in certain figures and not in others merely serves an explanatory purpose and is non-limiting. In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A mitral valve implant consisting of:
    an implant body configured to be attached and implanted onto an annulus of a patient's mitral valve, the implant body having an anterior portion in an anterior direction and a posterior portion in a posterior direction, wherein the posterior portion is configured to be anchored to a posterior aspect of the annulus of the mitral valve,
    a bridge connected to the implant body by two legs which are configured to support and position the bridge within a left ventricle (LV) of the patient when the implant body is implanted, wherein the bridge is configured to enable attachment of leaflet tissue thereto, and
    at least one pair of artificial chords attached to the bridge, and configured to fixate the leaflet tissue to the bridge;
    wherein the legs are mechanically configured to position the bridge below a coaptation line of leaflets of the mitral valve within a specified space, the specified space defined by a depth between 10 mm and 30 mm below the implant body, a width between 15 mm and 30 mm with respect to a median plane of the implant body, and a length between −5 mm and +15 mm with respect to a posterior edge of the implant body, so that, once the implant is in place, the legs and the bridge do not contact any of the LV walls, papillary muscles and chordae during operation of the heart,
    wherein the legs comprise at least one bend in the posterior direction, the legs are angled to the posterior direction with respect to a longitudinal plane going through connection points of the legs to the implant body, and the legs are configured to divert the bridge at a posterior angle of 30°-80° with respect to an annular plane,
    wherein the legs are connected to the implant body by two eyelets configured to be attached to the annulus, and at entry points configured to introduce the legs into the LV through anterolateral and posteromedial commissures, and
    wherein at least one of the implant body, the legs and the bridge are covered by at least one of ePTFE, Dacron and pericardial tissue.

2. The mitral valve implant of claim 1, wherein the anterior portion of the implant body is contiguous with the posterior portion of the implant body and comprises a series of inward and downward bends to the two legs.

3. The mitral valve implant of claim 1, wherein the bridge is covered with a bridge cuff comprising at least one of ePTFE, Dacron and pericardial tissue, and wherein the least one pair of artificial chords attached to the bridge cuff.

4. The mitral valve implant of claim 1, wherein the artificial chords attached to the bridge are configured as a single pair of the artificial chords that zig-zag between the bridge and the leaflet tissue, allowing at least one of: correction of a required length of the single pair of the artificial chords, guarantying a correct length of chord portion at each point of a leaflet-bridge distance, equalizing and balancing tension along the artificial chords and valve leaflet/s by providing the single pair of the artificial chords as a continuous suture line.

5. The mitral valve implant of claim 1, wherein the eyelets are open posteriorly, and wherein the eyelets and the implant body are in the same plane.

6. The mitral valve implant of claim 1, wherein the eyelets are raised above the plane of the implant body to tilt the mitral valve implant by a specified angle between 5-20° with respect to the annulus.

7. A device consisting of:
    a device body configured to be attached and implanted onto an annulus of a patient's mitral valve, the device body having an anterior portion in an anterior direction and a posterior portion in a posterior direction, wherein the posterior portion is configured to be anchored to a posterior aspect of the annulus of the mitral valve,
    a bridge connected to the device body by two legs which are configured to support and position the bridge within a left ventricle (LV) of the patient when the device body is implanted, wherein the bridge is covered with a bridge cuff, and wherein the legs are uncovered; and
    wherein the legs are mechanically configured to position the bridge within a specified space, the specified space defined by a depth between 10 mm and 30 mm below the device body, a width between 15 mm and 30 mm with respect to a median plane of the device, and a length between −5 mm and +15 mm with respect to a posterior edge of the device body, so that, once the device is in place, the legs and the bridge do not contact any of the LV walls, papillary muscles and chordae during operation of the heart.

8. The device of claim 7, wherein at least one of the device body and the bridge are covered by at least one of ePTFE, Dacron and pericardial tissue.

9. The device of claim 7, wherein the legs are angled to the posterior direction with respect to a longitudinal plane going through connection points of the legs to the device body.

10. The device of claim 7, wherein the device body, the legs and the bridge are made of one bended material loop comprising the at least one bend.

11. The device of claim 7, wherein the legs are configured to divert the bridge at a posterior angle of 30°-80° with respect to an annular plane of the annulus of the patient's mitral valve.

12. The device of claim 11, wherein the legs are configured to divert the bridge at the posterior angle of 40°-60° with respect to the annulus.

13. The device of claim 11, wherein the legs comprise at least one bend in the posterior direction.

14. The device of claim 7, wherein the legs are connected to the device body at points configured to introduce the legs into the LV through anterolateral and posteromedial commissures.

15. The device of claim 7, wherein the legs are connected to the device body at points configured to offset at least one of entry points of the legs into the LV with respect to anterolateral and posteromedial commissures of the patient's mitral valve by 2-8 mm in the posterior direction.

16. The device of claim 7, wherein the legs are connected to the device body by two eyelets configured to be attached to the annulus.

17. The device of claim 16, wherein the eyelets are open posteriorly, and wherein the eyelets and the device body are in the same plane.

18. The device of claim 16, wherein the eyelets are raised above the plane of the device body to tilt the device by a specified angle between 5-20° with respect to the annulus.

19. The device of claim 16, further comprising at least one pair of artificial chords attached to the bridge and/or to the eyelets, and configured to fixate leaflet tissue to the bridge.

20. The device of claim 19, wherein the artificial chords attached to the bridge are configured as a single pair of the artificial chords that zig-zag between the bridge and the leaflet tissue, allowing at least one of: correction of a required length of the single pair of the artificial chords, guaranteeing a correct length of chord portion at each point of a leaflet-bridge distance, equalizing and balancing tension along the artificial chords and valve leaflet/s by providing the single pair of the artificial chords as a continuous suture line.

21. The device of claim 7, wherein the bridge is configured to enable attachment of leaflet tissue thereto.

22. The device of claim 7, wherein the anterior portion is contiguous with the posterior portion and comprises a series of inward and downward bends to the two legs.

23. The device of claim 7, wherein the bridge cuff comprises at least one of ePTFE, Dacron and pericardial tissue, and wherein the at least one pair of artificial chords is attached to the bridge cuff.

24. A mitral valve implant consisting of:
an implant body comprising and covered with a body cuff, the implant body is configured to be attached and implanted onto an annulus of a patient's mitral valve, wherein the implant body has an anterior portion in an anterior direction and a posterior portion in a posterior direction, wherein the posterior portion of the implant body is configured to be anchored to a posterior aspect of the annulus of the mitral valve;
a bridge comprising and covered with a bridge cuff, the bridge is connected to the implant body by two legs which are configured to support and position the bridge within a left ventricle (LV) of the patient when the implant body is implanted, wherein the bridge is configured to enable attachment of leaflet tissue thereto, and
at least one pair of artificial chords is attached to the bridge cuff, and configured to fixate the leaflet tissue to the bridge;
wherein the anterior portion of the implant body is contiguous with the posterior portion of the implant body and comprises a series of inward and downward bends to the two legs;
wherein the legs are mechanically configured to position the bridge below a coaptation line of leaflets of the mitral valve within a specified space, the specified space defined by a depth between 10 mm and 30 mm below the implant body, a width between 15 mm and 30 mm with respect to a median plane of the implant body, and a length between −5 mm and +15 mm with respect to a posterior edge of the implant body, so that, once the implant is in place, the legs and the bridge do not contact any of the LV walls, papillary muscles and chordae during operation of the heart,
wherein the legs comprise at least one bend in the posterior direction, the legs are angled to the posterior direction with respect to a longitudinal plane going through connection points of the legs to the implant body, and the legs are configured to divert the bridge at a posterior angle of 30°-80° with respect to an annular plane,
wherein the legs are connected to the implant body by two eyelets configured to be attached to the annulus, and at entry points configured to introduce the legs into the LV through anterolateral and posteromedial commissures,
wherein the legs are uncovered, and
wherein the implant body cuff and the bridge cuff comprise at least one of ePTFE, Dacron and pericardial tissue.

25. The mitral valve implant of claim 24, wherein the at least one pair of artificial chords attached to the bridge is configured as a single pair of the artificial chords that zig-zag between the bridge and the leaflet tissue, allowing at least one of: correction of a required length of the single pair of the artificial chords, guaranteeing a correct length of chord portion at each point of a leaflet-bridge distance, equalizing and balancing tension along the artificial chords and valve leaflet/s by providing the single pair of the artificial chords as a continuous suture line.

26. The mitral valve implant of claim 24, wherein the eyelets are open posteriorly, and wherein the eyelets and the implant body are in the same plane.

27. The mitral valve implant of claim 24, wherein the eyelets are raised above the plane of the implant body to tilt the mitral valve implant by a specified angle between 5-20° with respect to the annulus.

* * * * *